US009938263B2

(12) United States Patent
Tanzi et al.

(10) Patent No.: US 9,938,263 B2
(45) Date of Patent: Apr. 10, 2018

(54) GAMMA-SECRETASE MODULATORS

(71) Applicants: The Regents of the University of California, A California Corporation, Oakland, CA (US); The General Hospital Corporation, Boston, MA (US)

(72) Inventors: Rudolph E. Tanzi, Charlestown, MA (US); Steven L. Wagner, San Diego, CA (US); Soan Cheng, San Diego, CA (US); William C. Mobley, La Jolla, CA (US)

(73) Assignees: The General Hospital Corporation, Boston, MA (US); The Regents of the University of California, Oakland, CA (US)

( * ) Notice: Subject to any disclaimer, the term of this patent is extended or adjusted under 35 U.S.C. 154(b) by 0 days.

(21) Appl. No.: 14/775,483

(22) PCT Filed: Mar. 12, 2014

(86) PCT No.: PCT/US2014/025016
§ 371 (c)(1),
(2) Date: Sep. 11, 2015

(87) PCT Pub. No.: WO2014/165263
PCT Pub. Date: Oct. 9, 2014

(65) Prior Publication Data
US 2016/0024073 A1 Jan. 28, 2016

Related U.S. Application Data

(60) Provisional application No. 61/777,941, filed on Mar. 12, 2013.

(51) Int. Cl.
*C07D 417/14* (2006.01)
*C07D 487/04* (2006.01)

(52) U.S. Cl.
CPC ......... *C07D 417/14* (2013.01); *C07D 487/04* (2013.01)

(58) Field of Classification Search
USPC ................... 514/220, 234.5, 253.1
See application file for complete search history.

(56) References Cited

U.S. PATENT DOCUMENTS

| RE28,819 E | 5/1976 | Thompson |
| 4,044,126 A | 8/1977 | Cook et al. |
| 4,328,245 A | 5/1982 | Yu et al. |
| 4,358,603 A | 11/1982 | Yu |
| 4,364,923 A | 12/1982 | Cook et al. |
| 4,409,239 A | 10/1983 | Yu |
| 4,410,545 A | 10/1983 | Yu et al. |
| 4,414,209 A | 11/1983 | Cook et al. |
| 4,522,811 A | 6/1985 | Eppstein et al. |
| 5,033,252 A | 7/1991 | Carter |
| 5,052,558 A | 10/1991 | Carter |
| 5,323,907 A | 6/1994 | Kalvelage |
| 5,709,874 A | 1/1998 | Hanson et al. |
| 5,860,957 A | 1/1999 | Jacobsen et al. |
| 6,267,983 B1 | 7/2001 | Fujii et al. |
| 6,316,652 B1 | 11/2001 | Steliou |
| 7,244,739 B2 | 7/2007 | Cheng et al. |
| 7,781,442 B2 | 8/2010 | Cheng et al. |
| 7,799,808 B2 | 9/2010 | Cheng et al. |
| 8,017,629 B2 | 9/2011 | Cheng et al. |
| 8,119,680 B2 | 2/2012 | Cheng et al. |
| 9,403,815 B2 * | 8/2016 | Wagner ............... C07D 417/14 |
| 2005/0070538 A1 | 3/2005 | Cheng et al. |
| 2006/0128712 A1 | 6/2006 | Jolidon et al. |
| 2009/0028787 A1 | 1/2009 | Gravenfors et al. |
| 2010/0063056 A1 | 3/2010 | Coleman et al. |
| 2011/0118236 A1 | 5/2011 | Mochizuki et al. |
| 2013/0023534 A1 | 1/2013 | Casillas et al. |
| 2013/0143862 A1 | 6/2013 | Ashcraft et al. |
| 2013/0165416 A1 * | 6/2013 | Wagner ............... C07F 9/65583 514/94 |

(Continued)

FOREIGN PATENT DOCUMENTS

| EP | 2585455 | 5/2013 |
| EP | 2968296 | 1/2016 |
| JP | 2013530987 | 8/2013 |

(Continued)

OTHER PUBLICATIONS

Abramoswki et al., "Dynamics of Aβ Turnover and Deposition in Different β-Amyloid Precursor Protein Transgenic Mouse Models Following γ-Secretase Inhibition," J. Pharmacol. Exp. Ther., 2008, 327:411-424.
Anderson et al., "Reductions in beta-amyloid inhibitors BMS-289948 and BMS-299897," concentrations in vivo by the gamma-secretase Biochem. Pharmacol., 2005, 69: 689-698.
Bonnelli et. al., Expert Opinion in Pharmacotherapy, 2007, Informa UK Ltd, vol. 8, No. 2, pp. 141-153.
Burbach et al., "Vessel ultrastructure in APP23 transgenic mice after passive anti-Abeta immunotherapy and subsequent intracerebral hemorrhage," Neurobiol Aging, 2007, 28: 202-212.
Coric et al., "Safety and Tolerability of the γ-Secretase Inhibitor Avagacestat in a Phase 2 Study of Mild to Moderate Alzheimer Disease," Arch. Neurol., Nov. 2012, 69:1430-1440.
Fleisher et al., "Phase II safety trial targeting amyloid beta production with a gamma-secretase inhibitor in Alzheimer's disease," Arch. Neurol., Aug. 2008, 65:1031-1038.
Gilman et al., "Clinical effects of Abeta immunization (AN1792) in patients with AD in an interrupted trial," Neurology, 2005, 64:1553-1562.

(Continued)

*Primary Examiner* — Pancham Bakshi
(74) *Attorney, Agent, or Firm* — Fish & Richardson P.C.

(57) ABSTRACT

There are provided, inner alia, compounds and methods for lowering total AB peptide production by inhibiting the catalytic activity of gamma-secretase. Since all of the major AB peptide variants, including the pathogenic AB42 as known in the art, are ultimately generated by gamma-secretase-mediated proteolysis of APP-C99 (i.e., the beta-secretase-mediated cleavage product of the amyloid protein precursor IAPPI), one approach to therapeutic intervention (e.g., intervention in Alzheimer's Disease, AD) relates to lowering total AB peptide production by inhibiting the catalytic activity of gamma-secretase.

23 Claims, No Drawings

(56) References Cited

U.S. PATENT DOCUMENTS

2014/0213570 A1    7/2014  Cheung et al.

FOREIGN PATENT DOCUMENTS

| WO | WO 2004/018997 | | 3/2004 | |
|---|---|---|---|---|
| WO | WO 2004/110350 | | 12/2004 | |
| WO | WO 2007/111904 | | 10/2007 | |
| WO | WO 2008/088881 | | 7/2008 | |
| WO | WO 2009/050227 | | 4/2009 | |
| WO | WO 2010/098487 | | 9/2010 | |
| WO | WO 2010/098488 | | 9/2010 | |
| WO | WO 2011/059048 | | 5/2011 | |
| WO | WO 2011/133882 | | 10/2011 | |
| WO | WO 2011/163636 | | 12/2011 | |
| WO | WO 2011/163636 | A2 * | 12/2011 | ........... C07D 417/14 |
| WO | WO2011/163636 | A3 * | 12/2011 | ......... A61K 31/4439 |
| WO | WO 2014/028459 | | 2/2014 | |
| WO | WO 2014/165263 | | 10/2014 | |

OTHER PUBLICATIONS

Graziano et. al., Current Neurology and Neuroscience Reports, 2009, Current Medicine Group LLC, vol. 9, pp. 423-429.

Green et al., "Effect of Tarenflurbil on Cognitive Decline and Activities of Daily Living in Patients With Mild Alzheimer Disease," J. Amer. Med. Asso., 2009, 302:2557-2564.

Hardy and Higgins, "Alzheimer's Disease: The Amyloid Cascade Hypothesis," Science, Apr. 1992, 256:184-185.

Hardy and Selkoe, "The Amyloid Hypothesis of Alzheimer's Disease: Progress and Problems on the Road to Therapeutics," Science, Jul. 2002, 297:353-356.

Imbimbo, Bruno P., "Therapeutic Potential of g-Secretase Inhibitors and Modulators," Current Topics in Medicinal Chemistry, 2008, 8:54-61.

Imbimbo, Journal of Alzheimer's Disease, 2009, IOS Press, vol. 17, pp. 757-760.

International Preliminary Report on Patentability in International Application No. PCT/US2011/041905, dated Dec. 28, 2012, 5 pages.

International Preliminary Report on Patentability in International Application No. PCT/US2014/025016, dated Sep. 15, 2015, 6 pages.

International Search Report and Written Opinion in International Application No. PCT/US2011/041905, dated Feb. 17, 2012, 8 pages.

International Search Report and Written Opinion in International Application No. PCT/US2014/025016, dated Aug. 27, 2014, 10 pages.

International Search Report and Written Opinion in International Application No. PCT/US2015/058429, dated Jan. 19, 2016, 8 pages.

Iwatsubo et al., "Visualization of A beta 42(43) and A beta 40 in senile plaques with end-specific A beta monoclonals: evidence that an initially deposited species is A beta 42(43)," Neuron., Jul. 1994 13:45-53.

Japanese Office Action in Japanese Application No. 2013/516839, dated May 20, 2015, 10 pages.

Kopan and Ilagan, "γ-Secretase: proteasome of the membrane?" Nat. Rev. Mol. Cell. Biol., 2004, 5:486-488.

Kounnas et al., "Modulation of γ-Secretase Reduces β-Amyloid Deposition in a Transgenic Mouse Model of Alzheimer's Disease," Neuron, Sep. 2010, 67:769-780.

Kukar et al., "Substrate-targeting γ-secretase modulators," Nature, Jun. 2008, 453:925-929.

Kumar-Singh et al., "Mean age-of-onset of familial Alzheimer disease caused by presenilin mutations correlates with both increased Aβ42 and decreased Aβ40," Hum. Mutat., Jul. 2006, 27:686-695.

Lanz et al., "Concentration-Dependent Modulation of Amyloid-β in Vivo and in Vitro Using the γ-Secretase Inhibitor, LY-450139," J. Pharmacol. Exp. Ther., 2006, 319:924-933.

Miles et al., "Bapineuzumab captures the N-terminus of the Alzheimer's disease amyloid-beta peptide in a helical conformation," Sci. Rep., Feb. 2013, 3:1302.

Netzer et al., "Gleevec inhibits β-amyloid production but not Notch cleavage," PNAS, Oct. 2003, 100(21):12444-12449.

Page et al., "Generation of Aβ38 and Aβ42 Is Independently and Differentially Affected by Familial Alzheimer Disease-associated Presenilin Mutations and γ-Secretase Modulation," J. Bio. Chem., Jan. 2008, 283(2):677-683.

Potter et al., "Increased in vivo amyloid-β42 production, exchange and loss in presenilin mutation carriers," Sci Trans! Med., Jun. 2013, 5:189ra77.

Qiu et al., "Epidemiology of Alzheimer's disease: occurrence, determinants, and strategies toward intervention," Dialogues Clin Neurosci., 2009, 11:111-28.

Sabbagh and Cummings, "Progressive cholinergic decline in Alzheimer's Disease: consideration for treatment with donepezil 23 mg in patients with moderate to severe symptomology," BMC Neurology, 2011, 11:21.

Salloway et al., "Two phase 3 trials of bapineuzimab in mild-to-moderate Alzheimer's disease," N. Engl. J. Med., Jan. 2014, 370:322-333.

Search Report dated Nov. 5, 2014, 26 pages.

Selkoe "Alzheimer's Disease: Genes, Proteins, and Therapy," Physiological Reviews, 2001, 81:741-66.

Smith et al., "The effect of plasma protein binding on in vivo efficacy: misconceptions in drug discovery," Nat. Rev. Drug Discov., 2010, 9:929-939.

Supplementary European Search Report in European Application No. EP 11799023, dated Oct. 24, 2013, 4 pages.

Tanzi and Bertram, "Twenty years of the Alzheimer's disease amyloid hypothesis: A genetic perspective," Cell, Feb. 2005, 120:545-555.

Taylor and Barton, "Synthesis of 2-Aminonicotinamides by Raney Nickel Cleavage of Pymzolo [3,4-b]-pyridines," J. Am. Chem. Soc., May 1959, 81:2448-52.

Uetrecht and Naisbitt, "Idiosyncratic adverse drug reactions: current concepts," Pharmacol. Rev., 2013, 65:779-808.

U.S. Non-Final Office Action in U.S. Appl. No. 13/806,692, dated Aug. 7, 2015, 26 pages.

U.S. Notice of Allowance in U.S. Appl. No. 13/806,692, dated Dec. 11, 2015, 10 pages.

U.S. Notice of Allowance in U.S. Appl. No. 13/806,692, dated Mar. 22, 2016, 10 pages.

U.S. Restriction Requirement in U.S. Appl. No. 13/806,692, dated Jan. 29, 2015, 14 pages.

Wagner et al., "Potential of gamma-secretase modulators in the treatment of Alzheimer's disease," Arch. Neurol., Oct. 2013, 69:1255-1258.

Wagner et al., "Soluble γ-Secretase Modulators Selectively Inhibit Production of the 42-Amino Acid Amyloid β Peptide Variant and Augment the Production of Multiple Carboxy-Truncated Amyloid β Species," Biochemistry, 2014, doi.org/10.1021/bi401537v (PMID 24401146).

Wakabayashi and De Strooper, "Presenilins: Members of the γ-Secretase Quartets, But Part-Time Soloists Too," Physiology, Aug. 2008, 23:194-204.

European Office Action in European Application No. 11799023.4, dated Oct. 14, 2016, 4 pages.

Extended European Search Report and European Search Opinion in Application No. 14779909.2, dated Sep. 7, 2016, 7 pages.

\* cited by examiner

GAMMA-SECRETASE MODULATORS

CROSS-REFERENCES TO RELATED APPLICATIONS

This application is a U.S. National Phase Application under 35 U.S.C. § 371 of International Patent Application No. PCT/US2014/025016, filed on Mar. 12, 2014, which claims the benefit of U.S. Provisional Application No. 61/777,941, filed on Mar. 12, 2013, the contents of which are incorporated herein by reference in their entirety and for all purposes.

STATEMENT AS TO RIGHTS TO INVENTIONS MADE UNDER FEDERALLY SPONSORED RESEARCH AND DEVELOPMENT

This invention was made with government support under Grant No. 1U01NS074501-1 awarded by NIH/NINDS. The government has certain rights in the invention.

BACKGROUND OF THE INVENTION

Since all of the major Aβ peptide variants, including the pathogenic $A\beta_{42}$ as known in the art, are ultimately generated by gamma-secretase-mediated proteolysis of APP-C99 (i.e., the beta-secretase-mediated cleavage product of the amyloid protein precursor |APP|), one approach to therapeutic intervention (e.g., intervention in Alzheimer's Disease, AD) relates to lowering total Aβ peptide production by inhibiting the catalytic activity of gamma-secretase. However, gamma-secretase catalyzes the proteolysis of a large number of membrane proteins including the Notch receptor which yields the Notch intracellular domain (NICD), a peptide necessary for proper cellular differentiation and development. Nonetheless, many inhibitors of gamma-secretase activity, generally referred to as gamma-secretase inhibitors (GSIs), have been discovered, and some are being developed clinically. See e.g., Coric, V. et al., 2012, *Arch Neurol.* 69:1430-1440.

Without wishing to be bound by theory, it is believed that GSIs have the liability of adverse events resulting from (at least in part) the inhibition of Notch proteolysis. See e.g., Wakabayashi T. & De Strooper, B., 2008, *Physiology* 23:194-204; Fleisher A. S., et al., 2008, *Arch Neurol.* 65:1031-1038. In addition, gamma-secretase is now known to hydrolyze a rather large number of type I membrane proteins (Wakabayashi & De Strooper, 2008, Id.), implying participation in critical membrane protein degradation and signaling pathway(s). Therefore, inhibiting this enzymatic complex, which has been described as the "proteosome of the membrane" (Kopan, R. & Ilagan, M. X., 2004, *Nat. Rev. Mal Cell. Biol.* 5:486-488), may in fact be detrimental to an aged AD population with an already compromised neuronal catabolism. Thus, as is the case for other age-related degenerative disorders (e.g., cardiovascular disease), successful disease modifying therapeutic approaches will require long term administration, beginning early in the disease process and with either very tolerable or without side effects.

Recently, an approach utilized NSAID-like substrate-targeted GSMs (i.e., tarenflurbil) which have been shown to selectively inhibit $A\beta_{42}$ (at least in vitro); however, their poor potency combined with their inability to cross the blood brain barrier resulted in a lack of efficacy in the clinic. See e.g., Kukar, T. L., et al., 2008, *Nature* 453:925-929; Green, R. C., et al. 2009, *J. Amer. Med. Asso.* 302:2557-2564; see also Cheng, S., et al., 2007, U.S. Pat. No. 7,244,939; Kounnas, M. Z. et al., 2010, *Neuron* 67:769-780. Assays useful in characterizing the GSMs and GSIs have been described previously. See e.g., Cheng, S., et al., 2007, Id.; Kounnas, M. Z. et al., 2010, Id.) Certain GSMs have been shown to be potent and efficacious in vivo for lowering the levels of $A\beta_{42}$ and $A\beta_{40}$ in both the plasma and brain of APP transgenic mice and chronic efficacy studies revealed dramatically attenuated AD-like pathology in the Tg2576 APP transgenic mouse model.

The poor aqueous solubilities of the earlier GSMs have hindered the necessary preclinical development required for an investigational new drug (IND) application. Thus, there remains a need in the art for safe and effective GSM's. The present application provides solutions to these problems.

BRIEF SUMMARY OF THE INVENTION

Provided herein, inter alia, are compounds (also referred to herein as soluble gamma-secretase modulators or SGSMs) that display a safer mechanistic approach since they do not actually inhibit gamma-secretase activity or prevent it from proteolyzing numerous other substrates. Also provided, inter alia, are SGSMs that offer an improved facility to achieve beneficial levels in the brain of a subject. In embodiments, the compounds disclosed herein display enhanced aqueous solubilities and contain improved pharmacokinetic and pharmacodynamic properties.

In a first aspect, there is provided a compound having the formula:

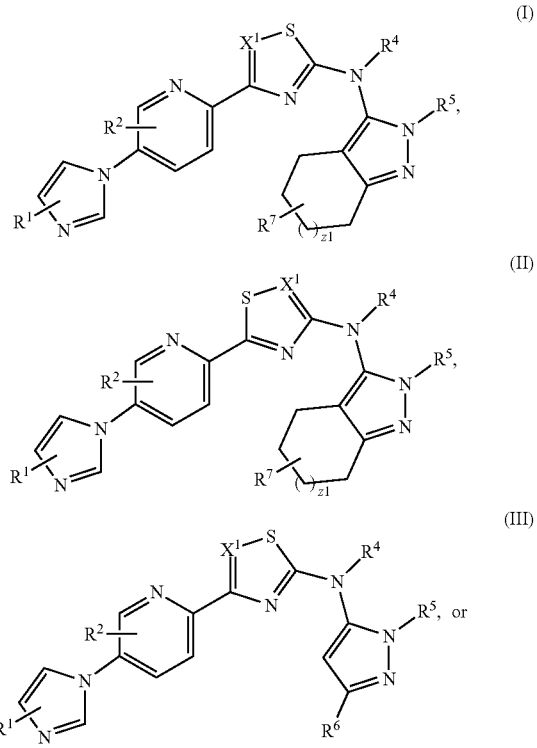

-continued

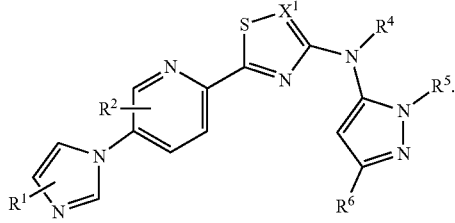
(IV)

For each of Formulae (I)-(IV), z1 is 0, 1 or 2. $X^1$ is $C(R^3)$ or N. $R^1$ is hydrogen, halogen, $-N_3$, $-CF_3$, $-CCl_3$, $-CBr_3$, $-CN$, $-CHO$, $-OR^{1A}$, $-NR^{1A}R^{1B}$, $-COOR^{1A}$, $-C(O)NR^{1A}R^{1B}$, $-NO_2$, $-SR^{1A}$, $-S(O)_{n1}R^{1A}$, $-S(O)_{n1}NR^{1A}R^{1B}$, $-NHNR^{1A}R^{1B}$, $-ONR^{1A}R^{1B}$, $-NHC(O)NHNR^{1A}R^{1B}$, substituted or unsubstituted alkyl, substituted or unsubstituted heteroalkyl, substituted or unsubstituted cycloalkyl, substituted or unsubstituted heterocycloalkyl, substituted or unsubstituted aryl, or substituted or unsubstituted heteroaryl. $R^2$ is hydrogen, halogen, $-N_3$, $-CF_3$, $-CCl_3$, $-CBr_3$, $-CI_3$, $-CN$, $-CHO$, $-OR^{2A}$, $-NR^{2A}R^{2B}$, $-COOR^{2A}$, $-C(O)NR^{2A}R^{2B}$, $-NO_2$, $-SR^{2A}$, $-S(O)_{n2}R^{2A}$, $-S(O)_{n2}OR^{2A}$, $-S(O)_{n2}NR^{2A}R^{2B}$, $-NHNR^{2A}R^{2B}$, $-ONR^{2A}R^{2B}$, $-NHC(O)NHNR^{2A}R^{2B}$, substituted or unsubstituted alkyl, substituted or unsubstituted heteroalkyl, substituted or unsubstituted cycloalkyl, substituted or unsubstituted heterocycloalkyl, substituted or unsubstituted aryl, or substituted or unsubstituted heteroaryl. $R^3$ is hydrogen, halogen, $-N_3$, $-CF_3$, $-CCl_3$, $-CBr_3$, $-CI_3$, $-CN$, $-CHO$, $-OR^{3A}$, $-NR^{3A}R^{3B}$, $-COOR^{3A}$, $-C(O)NR^{3A}R^{3B}$, $-NO_2$, $-SR^{3A}$, $-S(O)_{n3}R^{3A}$, $-S(O)_{n3}OR^{3A}$, $-S(O)_{n3}NR^{3A}R^{3B}$, $-NHNR^{3A}R^{3B}$, $-ONR^{3A}R^{3B}$, $-NHC(O)NHNR^{3A}R^{3B}$, substituted or unsubstituted alkyl, substituted or unsubstituted heteroalkyl, substituted or unsubstituted cycloalkyl, substituted or unsubstituted heterocycloalkyl, substituted or unsubstituted aryl, or substituted or unsubstituted heteroaryl. $R^4$ is hydrogen, halogen, $-N_3$, $-CF_3$, $-CCl_3$, $-CBr_3$, $-CI_3$, $-CN$, $-CHO$, $-OR^{4A}$, $-NR^{4A}R^{4B}$, $-COOR^{4A}$, $-C(O)NR^{4A}R^{4B}$, $-NO_2$, $-SR^{4A}$, $-S(O)_{n4}R^{4A}$, $-S(O)_{n4}OR^{4A}$, $-S(O)_{n4}NR^{4A}R^{4B}$, $-NHNR^{4A}R^{4B}$, $-ONR^{4A}R^{4B}$, $-NHC(O)NHNR^{4A}R^{4B}$, substituted or unsubstituted alkyl, substituted or unsubstituted heteroalkyl, substituted or unsubstituted cycloalkyl, substituted or unsubstituted heterocycloalkyl, substituted or unsubstituted aryl, or substituted or unsubstituted heteroaryl. $R^5$ is hydrogen, halogen, $-N_3$, $-CF_3$, $-CCl_3$, $-CBr_3$, $-CI_3$, $-CN$, $-CHO$, $-OR^{5A}$, $-NR^{5A}R^{5B}$, $-COOR^{5A}$, $-C(O)NR^{5A}R^{5B}$, $-NO_2$, $-SR^{5A}$, $-S(O)_{n5}R^{5A}$, $-S(O)_{n5}OR^{5A}$, $-S(O)_{n5}NR^{5A}R^{5B}$, $-NHNR^{5A}R^{5B}$, $-ONR^{5A}R^{5B}$, $-NHC(O)NHNR^{5A}R^{5B}$, substituted or unsubstituted alkyl, substituted or unsubstituted heteroalkyl, substituted or unsubstituted cycloalkyl, substituted or unsubstituted heterocycloalkyl, substituted or unsubstituted aryl, or substituted or unsubstituted heteroaryl, wherein $R^4$ and $R^5$ are optionally joined together to form a substituted or unsubstituted heterocycloalkyl, or substituted or unsubstituted heteroaryl. $R^6$ is $-CF_3$, substituted or unsubstituted cyclopropyl, or substituted or unsubstituted cyclobutyl. $R^7$ is independently hydrogen, halogen, $-N_3$, $-CF_3$, $-CCl_3$, $-CBr_3$, $-CI_3$, $-CN$, $-CHO$, $-OR^{7A}$, $-NR^{7A}R^{7B}$, $-COOR^{7A}$, $-C(O)NR^{7A}R^{7B}$, $-NO_2$, $-SR^{7A}$, $-S(O)_{n7}R^{7A}$, $-S(O)_{n7}OR^{7A}$, $-S(O)_{n7}NR^{7A}R^{7B}$, $-NHNR^{7A}R^{7B}$, $-ONR^{7A}R^{7B}$, $-NHC(O)NHNR^{7A}R^{7B}$, substituted or unsubstituted alkyl, substituted or unsubstituted heteroalkyl, substituted or unsubstituted cycloalkyl, substituted or unsubstituted heterocycloalkyl, substituted or unsubstituted aryl, or substituted or unsubstituted heteroaryl. $R^{1A}$, $R^{1B}$, $R^{2A}$, $R^{2B}$, $R^{3A}$, $R^{3B}$, $R^{4A}$, $R^{4B}$, $R^{5A}$, $R^{5B}$, $R^{7A}$ and $R^{7B}$ are independently hydrogen, substituted or unsubstituted alkyl, substituted or unsubstituted heteroalkyl, substituted or unsubstituted cycloalkyl, substituted or unsubstituted heterocycloalkyl, substituted or unsubstituted aryl, or substituted or unsubstituted heteroaryl. The variables n1, n2, n3, n4, n5 and n7 are independently 1 or 2.

In another aspect, there is provided a pharmaceutical composition including a compound disclosed herein and a pharmaceutically acceptable carrier.

In another aspect, there is provided a use of a compound disclosed herein for inhibiting production of $A\beta_{42}$ or $A\beta_{40}$ by a protease which proteolyzes an amyloid precursor protein (APP) or fragment thereof.

In another aspect, there is provided use of a compound disclosed herein for treating a disease or neurological disorder associated with elevated levels of specific fibrillogenic $A\beta$ peptides by inhibiting production of $A\beta_{42}$ or $A\beta_{40}$.

DETAILED DESCRIPTION OF THE INVENTION

I. Definitions

The abbreviations used herein have their conventional meaning within the chemical and biological arts. The chemical structures and formulae set forth herein are constructed according to the standard rules of chemical valency known in the chemical arts.

Where substituent groups are specified by their conventional chemical formulae, written from left to right, they equally encompass the chemically identical substituents that would result from writing the structure from right to left, e.g., $-CH_2O-$ is equivalent to $-OCH_2-$.

The term "alkyl," by itself or as part of another substituent, means, unless otherwise stated, a straight (i.e., unbranched) or branched chain, or combination thereof, which may be fully saturated, mono- or polyunsaturated and can include di- and multivalent radicals, having the number of carbon atoms designated (i.e., $C_1$-$C_{10}$ means one to ten carbons). Alkyl is an uncyclized chain. Examples of saturated hydrocarbon radicals include, but are not limited to, groups such as methyl, ethyl, n-propyl, isopropyl, n-butyl, t-butyl, isobutyl, sec-butyl, (cyclohexyl)methyl, homologs and isomers of, for example, n-pentyl, n-hexyl, n-heptyl, n-octyl, and the like. An unsaturated alkyl group is one having one or more double bonds or triple bonds. Examples of unsaturated alkyl groups include, but are not limited to, vinyl, 2-propenyl, crotyl, 2-isopentenyl, 2-(butadienyl), 2,4-pentadienyl, 3-(1,4-pentadienyl), ethynyl, 1- and 3-propynyl, 3-butynyl, and the higher homologs and isomers. An alkoxy is an alkyl attached to the remainder of the molecule via an oxygen linker ($-O-$).

The term "alkylene," by itself or as part of another substituent, means, unless otherwise stated, a divalent radical derived from an alkyl, as exemplified, but not limited by, $-CH_2CH_2CH_2CH_2-$. Typically, an alkyl (or alkylene) group will have from 1 to 24 carbon atoms, with those groups having 10 or fewer carbon atoms being preferred in the present invention. A "lower alkyl" or "lower alkylene" is a shorter chain alkyl or alkylene group, generally having eight or fewer carbon atoms.

The term "heteroalkyl," by itself or in combination with another term, means, unless otherwise stated, a stable straight or branched chain, or combinations thereof, consisting of at least one carbon atom and at least one heteroatom selected from the group consisting of O, N, P, Si, and S, and wherein the nitrogen and sulfur atoms may optionally be oxidized, and the nitrogen heteroatom may optionally be quaternized. The heteroatom(s) O, N, P, S, and Si may be placed at any interior position of the heteroalkyl group or at the position at which the alkyl group is attached to the remainder of the molecule. Heteroalkyl is an uncyclized chain. Examples include, but are not limited to: —CH$_2$—CH$_2$—O—CH$_3$, —CH$_2$—CH$_2$—NH—CH$_3$, —CH$_2$—CH$_2$—N(CH$_3$)—CH$_3$, —CH$_2$—S—CH$_2$—CH$_3$, —CH$_2$—CH$_2$, —S(O)—CH$_3$, —CH$_2$—CH$_2$—S(O)$_2$—CH$_3$, —Si(CH$_3$)$_3$, —CH$_2$—CH=N—OCH$_3$, —CH=CH—N(CH$_3$)—CH$_3$, —O—CH$_3$, —O—CH$_2$—CH$_3$, and —CN. Up to two heteroatoms may be consecutive, such as, for example, —CH$_2$—NH—OCH$_3$.

Similarly, the term "heteroalkylene," by itself or as part of another substituent, means, unless otherwise stated, a divalent radical derived from heteroalkyl, as exemplified, but not limited by, —CH$_2$—CH$_2$—S—CH$_2$—CH$_2$— and —CH$_2$—S—CH$_2$—CH$_2$—NH—CH$_2$—. For heteroalkylene groups, heteroatoms can also occupy either or both of the chain termini (e.g., alkyleneoxy, alkylenedioxy, alkyleneamino, alkylenediamino, and the like). Still further, for alkylene and heteroalkylene linking groups, no orientation of the linking group is implied by the direction in which the formula of the linking group is written. For example, the formula —C(O)$_2$R'— represents both —C(O)$_2$R'— and —R'C(O)$_2$—. As described above, heteroalkyl groups, as used herein, include those groups that are attached to the remainder of the molecule through a heteroatom, such as —C(O)R', —C(O)NR', —NR'R", —OR', —SR', and/or —SO$_2$R'. Where "heteroalkyl" is recited, followed by recitations of specific heteroalkyl groups, such as —NR'R" or the like, it will be understood that the terms heteroalkyl and —NR'R" are not redundant or mutually exclusive. Rather, the specific heteroalkyl groups are recited to add clarity. Thus, the term "heteroalkyl" should not be interpreted herein as excluding specific heteroalkyl groups, such as —NRR" or the like.

The terms "cycloalkyl" and "heterocycloalkyl," by themselves or in combination with other terms, mean, unless otherwise stated, cyclic versions of "alkyl" and "heteroalkyl," respectively. Cycloalkyl and heterocycloalkyl are not aromatic. Additionally, for heterocycloalkyl, a heteroatom can occupy the position at which the heterocycle is attached to the remainder of the molecule. Examples of cycloalkyl include, but are not limited to, cyclopropyl, cyclobutyl, cyclopentyl, cyclohexyl, 1-cyclohexenyl, 3-cyclohexenyl, cycloheptyl, and the like. Examples of heterocycloalkyl include, but are not limited to, 1-(1,2,5,6-tetrahydropyridyl), 1-piperidinyl, 2-piperidinyl, 3-piperidinyl, 4-morpholinyl, 3-morpholinyl, tetrahydrofuran-2-yl, tetrahydrofuran-3-yl, tetrahydrothien-2-yl, tetrahydrothien-3-yl, 1-piperazinyl, 2-piperazinyl, and the like. A "cycloalkylene" and a "heterocycloalkylene," alone or as part of another substituent, means a divalent radical derived from a cycloalkyl and heterocycloalkyl, respectively.

The terms "halo" or "halogen," by themselves or as part of another substituent, mean, unless otherwise stated, a fluorine, chlorine, bromine, or iodine atom. Additionally, terms such as "haloalkyl" are meant to include monohaloalkyl and polyhaloalkyl. For example, the term "halo(C$_1$-C$_4$)alkyl" includes, but is not limited to, fluoromethyl, difluoromethyl, trifluoromethyl, 2,2,2-trifluoroethyl, 4-chlorobutyl, 3-bromopropyl, and the like.

The term "acyl" means, unless otherwise stated, —C(O)R where R is a substituted or unsubstituted alkyl, substituted or unsubstituted cycloalkyl, substituted or unsubstituted heteroalkyl, substituted or unsubstituted heterocycloalkyl, substituted or unsubstituted aryl, or substituted or unsubstituted heteroaryl.

The term "aryl" means, unless otherwise stated, a polyunsaturated, aromatic, hydrocarbon substituent, which can be a single ring or multiple rings (preferably from 1 to 3 rings) that are fused together (i.e., a fused ring aryl) or linked covalently. A fused ring aryl refers to multiple rings fused together wherein at least one of the fused rings is an aryl ring. The term "heteroaryl" refers to aryl groups (or rings) that contain at least one heteroatom such as N, O, or S, wherein the nitrogen and sulfur atoms are optionally oxidized, and the nitrogen atom(s) are optionally quaternized. Thus, the term "heteroaryl" includes fused ring heteroaryl groups (i.e., multiple rings fused together wherein at least one of the fused rings is a heteroaromatic ring). A 5,6-fused ring heteroarylene refers to two rings fused together, wherein one ring has 5 members and the other ring has 6 members, and wherein at least one ring is a heteroaryl ring. Likewise, a 6,6-fused ring heteroarylene refers to two rings fused together, wherein one ring has 6 members and the other ring has 6 members, and wherein at least one ring is a heteroaryl ring. And a 6,5-fused ring heteroarylene refers to two rings fused together, wherein one ring has 6 members and the other ring has 5 members, and wherein at least one ring is a heteroaryl ring. A heteroaryl group can be attached to the remainder of the molecule through a carbon or heteroatom. Non-limiting examples of aryl and heteroaryl groups include phenyl, 1-naphthyl, 2-naphthyl, 4-biphenyl, 1-pyrrolyl, 2-pyrrolyl, 3-pyrrolyl, 3-pyrazolyl, 2-imidazolyl, 4-imidazolyl, pyrazinyl, 2-oxazolyl, 4-oxazolyl, 2-phenyl-4-oxazolyl, 5-oxazolyl, 3-isoxazolyl, 4-isoxazolyl, 5-isoxazolyl, 2-thiazolyl, 4-thiazolyl, 5-thiazolyl, 2-furyl, 3-furyl, 2-thienyl, 3-thienyl, 2-pyridyl, 3-pyridyl, 4-pyridyl, 2-pyrimidyl, 4-pyrimidyl, 5-benzothiazolyl, purinyl, 2-benzimidazolyl, 5-indolyl, 1-isoquinolyl, 5-isoquinolyl, 2-quinoxalinyl, 5-quinoxalinyl, 3-quinolyl, and 6-quinolyl. Substituents for each of the above noted aryl and heteroaryl ring systems are selected from the group of acceptable substituents described below. An "arylene" and a "heteroarylene," alone or as part of another substituent, mean a divalent radical derived from an aryl and heteroaryl, respectively. Non-limiting examples of aryl and heteroaryl groups include pyridinyl, pyrimidinyl, thiophenyl, thienyl, furanyl, indolyl, benzoxadiazolyl, benzodioxolyl, benzodioxanyl, thianaphthanyl, pyrrolopyridinyl, indazolyl, quinolinyl, quinoxalinyl, pyridopyrazinyl, quinazolinonyl, benzoisoxazolyl, imidazopyridinyl, benzofuranyl, benzothienyl, benzothiophenyl, phenyl, naphthyl, biphenyl, pyrrolyl, pyrazolyl, imidazolyl, pyrazinyl, oxazolyl, isoxazolyl, thiazolyl, furylthienyl, pyridyl, pyrimidyl, benzothiazolyl, purinyl, benzimidazolyl, isoquinolyl, thiadiazolyl, oxadiazolyl, pyrrolyl, diazolyl, triazolyl, tetrazolyl, benzothiadiazolyl, isothiazolyl, pyrazolopyrimidinyl, pyrrolopyrimidinyl, benzotriazolyl, benzoxazolyl, or quinolyl. The examples above may be substituted or unsubstituted and divalent radicals of each heteroaryl example above are non-limiting examples of heteroarylene.

A fused ring heterocyloalkyl-aryl is an aryl fused to a heterocycloalkyl. A fused ring heterocycloalkyl-heteroaryl is a heteroaryl fused to a heterocycloalkyl. A fused ring heterocycloalkyl-cycloalkyl is a heterocycloalkyl fused to a cycloalkyl. A fused ring heterocycloalkyl-heterocycloalkyl is a heterocycloalkyl fused to another heterocycloalkyl. Fused ring heterocycloalkyl-aryl, fused ring heterocycloalkyl-heteroaryl, fused ring heterocycloalkyl-cycloalkyl, or fused ring heterocycloalkyl-heterocycloalkyl may each independently be unsubstituted or substituted with one or more of the substituents described herein.

For brevity, the term "aryl" when used in combination with other terms (e.g., aryloxy, arylthioxy, arylalkyl) includes both aryl and heteroaryl rings as defined above. Thus, the term "arylalkyl" is meant to include those radicals in which an aryl group is attached to an alkyl group (e.g., benzyl, phenethyl, pyridylmethyl, and the like) including those alkyl groups in which a carbon atom (e.g., a methylene group) has been replaced by, for example, an oxygen atom (e.g., phenoxymethyl, 2-pyridyloxymethyl, 3-(1-naphthyloxy)propyl, and the like).

The term "oxo," as used herein, means an oxygen that is double bonded to a carbon atom.

The term "alkylsulfonyl," as used herein, means a moiety having the formula —S($O_2$)—R', where $R^1$ is an alkyl group as defined above. R' may have a specified number of carbons (e.g., "$C_1$-$C_4$ alkylsulfony.").

Each of the above terms (e.g., "alkyl," "heteroalkyl," "aryl," and "heteroaryl") includes both substituted and unsubstituted forms of the indicated radical. Preferred substituents for each type of radical are provided below.

Substituents for the alkyl and heteroalkyl radicals (including those groups often referred to as alkylene, alkenyl, heteroalkylene, heteroalkenyl, alkynyl, cycloalkyl, heterocycloalkyl, cycloalkenyl, and heterocycloalkenyl) can be one or more of a variety of groups selected from, but not limited to, —OR', =O, =NR', =N—OR', —NR'R", —SR', -halogen, —SiR'R"R'", —OC(O)R', —C(O)R', —$CO_2$R', —CONR'R", —OC(O)NR'R", —NR"C(O)R', —NR'—C(O)NR"R'", —NR"C(O)$_2$R', —NR—C(NR'R"R'")=NR"", —NR—C(NR'R")=NR'", —S(O)R', —S(O)$_2$R', —S(O)$_2$NR'R", —NRSO$_2$R', —NR'NR"R'", —ONR'R", —NR'C=(O)NR"NR'"R"", —CN, —$NO_2$, in a number ranging from zero to (2m'+1), where m' is the total number of carbon atoms in such radical. R, R', R", R'", and R"" each preferably independently refer to hydrogen, substituted or unsubstituted heteroalkyl, substituted or unsubstituted cycloalkyl, substituted or unsubstituted heterocycloalkyl, substituted or unsubstituted aryl (e.g., aryl substituted with 1-3 halogens), substituted or unsubstituted heteroaryl, substituted or unsubstituted alkyl, alkoxy, or thioalkoxy groups, or arylalkyl groups. When a compound of the invention includes more than one R group, for example, each of the R groups is independently selected as are each R', R", R'", and R"" group when more than one of these groups is present. When R' and R" are attached to the same nitrogen atom, they can be combined with the nitrogen atom to form a 4-, 5-, 6-, or 7-membered ring. For example, —NR'R" includes, but is not limited to, 1-pyrrolidinyl and 4-morpholinyl. From the above discussion of substituents, one of skill in the art will understand that the term "alkyl" is meant to include groups including carbon atoms bound to groups other than hydrogen groups, such as haloalkyl (e.g., —$CF_3$ and —$CH_2CF_3$) and acyl (e.g., —C(O)$CH_3$, —C(O)$CF_3$, —C(O)$CH_2OCH_3$, and the like).

Similar to the substituents described for the alkyl radical, substituents for the aryl and heteroaryl groups are varied and are selected from, for example: —OR', —NR'R", —SR', -halogen, —SiR'R"R'", —OC(O)R', —C(O)R', —$CO_2$R', —CONR'R", —OC(O)NR'R", —NR"C(O)R', —NR'—C(O)NR"R'", —NR"C(O)$_2$R', —NR—C(NR'R"R'")=NR"", —NR—C(NR'R")=NR'", —S(O)R', —S(O)$_2$R', —S(O)$_2$NR'R", —NRSO$_2$R', —CN, —$NO_2$, —R', —$N_3$, —CH(Ph)$_2$, fluoro($C_1$-$C_4$)alkoxy, and fluoro($C_1$-$C_4$)alkyl, in a number ranging from zero to the total number of open valences on the aromatic ring system; and where R', R", R'", and R"" are preferably independently selected from hydrogen, substituted or unsubstituted alkyl, substituted or unsubstituted heteroalkyl, substituted or unsubstituted cycloalkyl, substituted or unsubstituted heterocycloalkyl, substituted or unsubstituted aryl, and substituted or unsubstituted heteroaryl. When a compound of the invention includes more than one R group, for example, each of the R groups is independently selected as are each R', R", R'", and R"" groups when more than one of these groups is present.

Two or more substituents may optionally be joined to form aryl, heteroaryl, cycloalkyl, or heterocycloalkyl groups. Such so-called ring-forming substituents are typically, though not necessarily, found attached to a cyclic base structure. In embodiments, the ring-forming substituents are attached to adjacent members of the base structure. For example, two ring-forming substituents attached to adjacent members of a cyclic base structure create a fused ring structure. In another embodiment, the ring-forming substituents are attached to a single member of the base structure. For example, two ring-forming substituents attached to a single member of a cyclic base structure create a spirocyclic structure. In yet another embodiment, the ring-forming substituents are attached to non-adjacent members of the base structure.

Two of the substituents on adjacent atoms of the aryl or heteroaryl ring may optionally form a ring of the formula -T-C(O)—(CRR')$_q$—U—, wherein T and U are independently —NR—, —O—, —CRR'—, or a single bond, and q is an integer of from 0 to 3. Alternatively, two of the substituents on adjacent atoms of the aryl or heteroaryl ring may optionally be replaced with a substituent of the formula -A-($CH_2$)$_r$—B—, wherein A and B are independently —CRR'—, —O—, —NR—, —S—, —S(O)—, —S(O)$_2$—, —S(O)$_2$NR'—, or a single bond, and r is an integer of from 1 to 4. One of the single bands of the new ring so formed may optionally be replaced with a double bond. Alternatively, two of the substituents on adjacent atoms of the aryl or heteroaryl ring may optionally be replaced with a substituent of the formula —(CRR')$_s$—X'—(C"R'")$_d$—, where s and d are independently integers of from 0 to 3, and $X^1$ is —O—, —NR'—, —S—, —S(O)—, —S(O)$_2$—, or —S(O)$_2$NR'—. The substituents R, R', R", and R'" are preferably independently selected from hydrogen, substituted or unsubstituted alkyl, substituted or unsubstituted cycloalkyl, substituted or unsubstituted heterocycloalkyl, substituted or unsubstituted aryl, and substituted or unsubstituted heteroaryl.

As used herein, the terms "heteroatom" or "ring heteroatom" are meant to include oxygen (O), nitrogen (N), sulfur (S), phosphorus (P), and silicon (Si).

A "substituent group," as used herein, means a group selected from the following moieties:

(A) —OH, —SH, —CN, —$CF_3$, —$NO_2$, oxo, halogen, unsubstituted alkyl, unsubstituted heteroalkyl, unsubstituted cycloalkyl, unsubstituted heterocycloalkyl, unsubstituted aryl, unsubstituted heteroaryl, and (B) alkyl, heteroalkyl, cycloalkyl, heterocycloalkyl, aryl, and heteroaryl, substituted with at least one substituent selected from:

(i) oxo, —OH, —$NH_2$, —SH, —CN, —$CF_3$, —$NO_2$, halogen, unsubstituted alkyl, unsubstituted heteroalkyl, unsubstituted cycloalkyl, unsubstituted heterocycloalkyl, unsubstituted aryl, unsubstituted heteroaryl, and (ii) alkyl, heteroalkyl, cycloalkyl, heterocycloalkyl, aryl, and heteroaryl, substituted with at least one substituent selected from:
(a) oxo, —OH, —NH$_2$, —SH, —CN, —NO$_2$, halogen, unsubstituted alkyl, unsubstituted heteroalkyl, unsubstituted cycloalkyl, unsubstituted heterocycloalkyl, unsubstituted aryl, unsubstituted heteroaryl, and
(b) alkyl, heteroalkyl, cycloalkyl, heterocycloalkyl, aryl, or heteroaryl, substituted with at least one substituent selected from:
oxo, —OH, —NH$_2$, —SH, —CN, —CF$_3$, —NO$_2$, halogen, unsubstituted alkyl, unsubstituted heteroalkyl, unsubstituted cycloalkyl, unsubstituted heterocycloalkyl, unsubstituted aryl, and unsubstituted heteroaryl.

A "size-limited substituent" or "size-limited substituent group," as used herein, means a group selected from all of the substituents described above for a "substituent group," wherein each substituted or unsubstituted alkyl is a substituted or unsubstituted C$_1$-C$_{20}$ alkyl, each substituted or unsubstituted heteroalkyl is a substituted or unsubstituted 2 to 20 membered heteroalkyl, each substituted or unsubstituted cycloalkyl is a substituted or unsubstituted C$_4$-C$_8$ cycloalkyl, each substituted or unsubstituted heterocycloalkyl is a substituted or unsubstituted 3 to 8 membered heterocycloalkyl, each substituted or unsubstituted aryl is a substituted or unsubstituted C$_6$-C$_{10}$ aryl, and each substituted or unsubstituted heteroaryl is a substituted or unsubstituted 5 to 10 membered heteroaryl.

A "lower substituent" or "lower substituent group," as used herein, means a group selected from all of the substituents described above for a "substituent group," wherein each substituted or unsubstituted alkyl is a substituted or unsubstituted C$_1$-C$_8$ alkyl, each substituted or unsubstituted heteroalkyl is a substituted or unsubstituted 2 to 8 membered heteroalkyl, each substituted or unsubstituted cycloalkyl is a substituted or unsubstituted C$_3$-C$_7$ cycloalkyl, each substituted or unsubstituted heterocycloalkyl is a substituted or unsubstituted 3 to 8 membered heterocycloalkyl, each substituted or unsubstituted aryl is a substituted or unsubstituted C$_6$-C$_{10}$ aryl, and each substituted or unsubstituted heteroaryl is a substituted or unsubstituted 5 to 9 membered heteroaryl.

In embodiments, each substituted group described in the compounds herein is substituted with at least one substituent group. More specifically, in some embodiments, each substituted alkyl, substituted heteroalkyl, substituted cycloalkyl, substituted heterocycloalkyl, substituted aryl, substituted heteroaryl, substituted alkylene, substituted heteroalkylene, substituted cycloalkylene, substituted heterocycloalkylene, substituted arylene, and/or substituted heteroarylene described in the compounds herein are substituted with at least one substituent group. In embodiments, at least one or all of these groups are substituted with at least one size-limited substituent group. In embodiments, at least one or all of these groups are substituted with at least one lower substituent group.

In embodiments of the compounds herein, each substituted or unsubstituted alkyl is a substituted or unsubstituted C$_1$-C$_{20}$ alkyl, each substituted or unsubstituted heteroalkyl is a substituted or unsubstituted 2 to 20 membered heteroalkyl, each substituted or unsubstituted cycloalkyl is a substituted or unsubstituted C$_2$-C$_8$ cycloalkyl, each substituted or unsubstituted heterocycloalkyl is a substituted or unsubstituted 3 to 8 membered heterocycloalkyl, each substituted or unsubstituted aryl is a substituted or unsubstituted C$_6$-C$_{10}$ aryl, and/or each substituted or unsubstituted heteroaryl is a substituted or unsubstituted 5 to 10 membered heteroaryl. In embodiments of the compounds herein, each substituted or unsubstituted alkylene is a substituted or unsubstituted C$_1$-C$_{20}$ alkylene, each substituted or unsubstituted heteroalkylene is a substituted or unsubstituted 2 to 20 membered heteroalkylene, each substituted or unsubstituted cycloalkylene is a substituted or unsubstituted C$_3$-C$_8$ cycloalkylene, each substituted or unsubstituted heterocycloalkylene is a substituted or unsubstituted 3 to 8 membered heterocycloalkylene, each substituted or unsubstituted arylene is a substituted or unsubstituted C$_5$-C$_{10}$ arylene, and/or each substituted or unsubstituted heteroarylene is a substituted or unsubstituted 5 to 10 membered heteroarylene.

In embodiments, each substituted or unsubstituted alkyl is a substituted or unsubstituted C$_1$-C$_8$ alkyl, each substituted or unsubstituted heteroalkyl is a substituted or unsubstituted 2 to 8 membered heteroalkyl, each substituted or unsubstituted cycloalkyl is a substituted or unsubstituted C$_3$-C$_7$ cycloalkyl, each substituted or unsubstituted heterocycloalkyl is a substituted or unsubstituted 3 to 7 membered heterocycloalkyl, each substituted or unsubstituted aryl is a substituted or unsubstituted C$_6$-C$_{10}$ aryl, and/or each substituted or unsubstituted heteroaryl is a substituted or unsubstituted 5 to 9 membered heteroaryl. In embodiments, each substituted or unsubstituted alkylene is a substituted or unsubstituted C$_1$-C$_8$ alkylene, each substituted or unsubstituted heteroalkylene is a substituted or unsubstituted 2 to 8 membered heteroalkylene, each substituted or unsubstituted cycloalkylene is a substituted or unsubstituted C$_3$-C$_7$ cycloalkylene, each substituted or unsubstituted heterocycloalkylene is a substituted or unsubstituted 3 to 7 membered heterocycloalkylene, each substituted or unsubstituted arylene is a substituted or unsubstituted C$_6$-C$_{10}$ arylene, and/or each substituted or unsubstituted heteroarylene is a substituted or unsubstituted 5 to 9 membered heteroarylene. In embodiments, the compound is a chemical species set forth in the Examples section, figures, or tables below.

Provided herein are agents (e.g., compounds disclosed herein) in a prodrug form. Prodrugs of the compounds described herein are those compounds that readily undergo chemical changes under select physiological conditions to provide the final agents (e.g., compounds disclosed herein). Additionally, prodrugs can be converted to agents by chemical or biochemical methods in an ex vivo environment. Prodrugs described herein include compounds that readily undergo chemical changes under select physiological conditions to provide agents to a biological system (e.g. in a subject, in an infected cell, in a cancer cell, in the extracellular space near an infected cell, in the extracellular space near a cancer cell from the moieties attached to the prodrug moiety and included in the prodrug (e.g. compound disclosed herein).

The symbol  denotes the point of attachment of a chemical moiety to the remainder of a molecule or chemical formula.

The terms "a" or "an," as used in herein means one or more. In addition, the phrase "substituted with a[n]," as used herein, means the specified group may be substituted with one or more of any or all of the named substituents. For example, where a group, such as an alkyl or heteroaryl group, is "substituted with an unsubstituted C$_1$-C$_{20}$ alkyl, or unsubstituted 2 to 20 membered heteroalkyl," the group may contain one or more unsubstituted alkyls, and/or one or more unsubstituted 2 to 20 membered heteroalkyls. Moreover, where a moiety is substituted with an R substituent, the group may be referred to as "R-substituted." Where a moiety is R-substituted, the moiety is substituted with at least one R substituent and each R substituent is optionally different.

Descriptions of compounds of the present invention are limited by principles of chemical bonding known to those skilled in the art. Accordingly, where a group may be substituted by one or more of a number of substituents, such substitutions are selected so as to comply with principles of chemical bonding and to give compounds which are not inherently unstable and/or would be known to one of ordinary skill in the art as likely to be unstable under ambient conditions, such as aqueous, neutral, and several known physiological conditions. For example, a heterocycloalkyl or heteroaryl is attached to the remainder of the molecule via a ring heteroatom in compliance with principles of chemical bonding known to those skilled in the art thereby avoiding inherently unstable compounds.

The term "drug" is used in accordance with its common meaning and refers to a substance which has a physiological effect (e.g. beneficial effect, is useful for treating a subject) when introduced into or to a subject (e.g. in or on the body of a subject or patient). A drug moiety is a radical of a drug.

As used herein, the term "salt" refers to acid or base salts of the compounds used in the methods of the present invention. Illustrative examples of acceptable salts are mineral acid (hydrochloric acid, hydrobromic acid, phosphoric acid, and the like) salts, organic acid (acetic acid, propionic acid, glutamic acid, citric acid and the like) salts, quaternary ammonium (methyl iodide, ethyl iodide, and the like) salts.

As used herein, the term "isomers" refers to compounds having the same number and kind of atoms, and hence the same molecular weight, but differing in respect to the structural arrangement or configuration of the atoms.

The term "tautomer," as used herein, refers to one of two or more structural isomers which exist in equilibrium and which are readily converted from one isomeric form to another.

It will be apparent to one skilled in the art that certain compounds of this invention may exist in tautomeric forms, all such tautomeric forms of the compounds being within the scope of the invention.

Unless otherwise stated, structures depicted herein are also meant to include all stereochemical forms of the structure; i.e., the R and S configurations for each asymmetric center. Therefore, single stereochemical isomers as well as enantiomeric and diastereomeric mixtures of the present compounds are within the scope of the invention.

Unless otherwise stated, structures depicted herein are also meant to include compounds which differ only in the presence of one or more isotopically enriched atoms. For example, compounds having the present structures except for the replacement of a hydrogen by a deuterium or tritium, or the replacement of a carbon by $^{13}$C- or $^{14}$C-enriched carbon are within the scope of this invention.

The terms "fibrillogenic," "fibrillogenic Aβ peptide" and the like refer, in the usual and customary sense, to a change in conformation of normally circulating soluble Aβ peptides into amyloid fibrils in the form of senile plaques, as known in the art. Thus, there are provided compounds and methods for modulating (e.g., reducing) levels of fibrillogenic Aβ peptides, e.g., Aβ$_{40}$ and Aβ$_{42}$, and concomitantly modulating (e.g., increasing) the levels of shorter less fibrillogenic Aβ peptides (e.g. Aβ$_{38}$ and Aβ$_{37}$) from the APP-CTFs.

The term "modulate" or "modulating" with respect to Aβ level, refers to a detectable increase or decrease in the amount (or level) of at least one species of the Aβ peptide (such as Aβ$_{43}$, Aβ$_{42}$, Aβ$_{40}$, Aβ$_{39}$, Aβ$_{38}$, Aβ$_{37}$, Aβ$_{34}$, etc., as known in the art); a detectable increase or decrease in the relative amount (or level) of different species of Aβ peptides (such as the ratio of Aβ$_{42}$ to Aβ$_{40}$); a detectable increase or decrease in the amount, or relative amount, of Aβ in a particular form (such as monomeric, oligomeric, or fibrillar form; in solution or aggregated in a plaque; in a particular conformation; etc.); and/or a detectable increase or decrease in the amount, or relative amount, of a particular Aβ species in a particular location (such as an intracellular, membrane-associated or extracellular location, or in a particular tissue or body fluid). In preferred embodiments, modulation is detectable as a decrease in the level of Aβ$_{42}$ or Aβ$_{40}$, or an increase in the level of Aβ$_{37}$ or Aβ$_{38}$. Modulation of Aβ levels can be evidenced, for example, by an increase or decrease of at least 5%, such as at least 10%, 20%, 30%, 40%, 50%, 75%, 90% or more, of the amount, or relative amount, of an Aβ species, or of a particular form of Aβ, relative to a reference level. Modulation can be an increase or decrease that is a statistically significant difference relative to the reference level.

The term "contacting" refers to bringing into association, either directly or indirectly, two or more substances. Contacting may occur in vivo, ex vivo or in vitro. A source of APP, amyloid precursor fragment thereof and/or Aβ or source of gamma-secretase activity, that is a human or other animal can be contacted with a compound, for example, by therapeutic or prophylactic administration of the compound. A source of APP, amyloid precursor fragment thereof and/or Aβ that is a tissue, tissue extract or cell can be contacted with a compound, for example, by introduction of the compound into the culture medium. A source of APP, amyloid precursor fragment thereof and/or Aβ that is a fluid, such as extracellular medium, can be contacted with a compound, for example, by admixing the compound with the fluid.

The terms "pharmaceutically acceptable excipient" and "pharmaceutically acceptable carrier" refer, in the usual and customary sense, to a substance that aids the administration of an active agent to and absorption by a subject and can be included in the compositions of the present invention without causing a significant adverse toxicological effect on the patient. Non-limiting examples of pharmaceutically acceptable excipients include water, dimethyl sulfoxide (DMSO), NaCl, normal saline solutions, lactated Ringer's, normal sucrose, normal glucose, binders, fillers, disintegrants, lubricants, coatings, sweeteners, flavors, salt solutions (such as Ringer's solution), alcohols, oils, gelatins, carbohydrates such as lactose, amylose or starch, fatty acid esters, hydroxymethylcellulose, polyvinyl pyrrolidine, polyethylene glycol, and colors, and the like. Such preparations can be sterilized and, if desired, mixed with auxiliary agents such as lubricants, preservatives, stabilizers, wetting agents, emulsifiers, salts for influencing osmotic pressure, buffers, coloring, and/or aromatic substances and the like that do not deleteriously react with the compounds of the invention. One of skill in the art will recognize that other pharmaceutical excipients are useful in the present invention.

The term "pharmaceutically acceptable salts" is meant to include salts of the active compounds that are prepared with relatively nontoxic acids or bases, depending on the particular substituents found on the compounds described herein. When compounds of the present invention contain relatively acidic functionalities, base addition salts can be obtained by contacting the neutral form of such compounds with a sufficient amount of the desired base, either neat or in a suitable inert solvent. Examples of pharmaceutically acceptable base addition salts include sodium, potassium, calcium, ammonium, organic amino, or magnesium salt, or a similar salt. When compounds of the present invention contain relatively basic functionalities, acid addition salts can be obtained by contacting the neutral form of such compounds with a sufficient amount of the desired acid, either neat or in a suitable inert solvent. Examples of pharmaceutically acceptable acid addition salts include those derived from inorganic acids like hydrochloric, hydrobromic, nitric, carbonic, monohydrogencarbonic, phosphoric, monohydrogenphosphoric, dihydrogenphosphoric, sulfuric, monohydrogensulfuric, hydriodic, or phosphorous acids and the like, as well as the salts derived from relatively nontoxic organic acids like acetic, propionic, isobutyric, maleic, malonic, benzoic, succinic, suberic, fumaric, lactic, mandelic, phthalic, benzenesulfonic, p-tolylsulfonic, citric, tartaric, oxalic, methanesulfonic, and the like. Also included are salts of amino acids such as arginate and the like, and salts of organic acids like glucuronic or galactunoric acids and the like (see, for example, Berge et al., "Pharmaceutical Salts", *Journal of Pharmaceutical Science,* 1977, 66:1-19). Certain specific compounds of the present invention contain both basic and acidic functionalities that allow the compounds to be converted into either base or acid addition salts.

Thus, the compounds of the present invention may exist as salts, such as with pharmaceutically acceptable acids. The present invention includes such salts. Examples of such salts include hydrochlorides, hydrobromides, sulfates, methanesulfonates, nitrates, maleates, acetates, citrates, fumarates, tartrates (e.g., (+)-tartrates, (−)-tartrates, or mixtures thereof including racemic mixtures), succinates, benzoates, and salts with amino acids such as glutamic acid. These salts may be prepared by methods known to those skilled in the art.

The neutral forms of the compounds are preferably regenerated by contacting the salt with a base or acid and isolating the parent compound in the conventional manner. The parent form of the compound differs from the various salt forms in certain physical properties, such as solubility in polar solvents.

Certain compounds of the present invention can exist in unsolvated forms as well as solvated forms, including hydrated forms. In general, the solvated forms are equivalent to unsolvated forms and are encompassed within the scope of the present invention. Certain compounds of the present invention may exist in multiple crystalline or amorphous forms. In general, all physical forms are equivalent for the uses contemplated by the present invention and are intended to be within the scope of the present invention.

Certain compounds of the present invention possess asymmetric carbon atoms (optical or chiral centers) or double bonds; the enantiomers, racemates, diastereomers, tautomers, geometric isomers, stereoisomeric forms that may be defined, in terms of absolute stereochemistry, as (R)- or (S)- or, as (D)- or (L)- for amino acids, and individual isomers are encompassed within the scope of the present invention. Compounds disclosed herein do not include those which are known in art to be too unstable to synthesize and/or isolate. The present disclosure is meant to include compounds in racemic and optically pure forms. Optically active (R)- and (S)-, or (D)- and (L)-isomers may be prepared using chiral synthons or chiral reagents, or resolved using conventional techniques. When the compounds described herein contain olefinic bonds or other centers of geometric asymmetry, and unless specified otherwise, it is intended that the compounds include both E and Z geometric isomers.

The compounds of the present invention may also contain unnatural proportions of atomic isotopes at one or more of the atoms that constitute such compounds. For example, the compounds may be radiolabeled with radioactive isotopes, such as for example tritium ($^3$H), iodine-125 ($^{125}$I), or carbon-14 ($^{14}$C). All isotopic variations of the compounds of the present invention, whether radioactive or not, are encompassed within the scope of the present invention.

The terms "treating" or "treatment" refers to any indicia of success in the treatment or amelioration of an injury, disease, pathology or condition, including any objective or subjective parameter such as abatement; remission; diminishing of symptoms or making the injury, pathology or condition more tolerable to the patient; slowing in the rate of degeneration or decline; making the final point of degeneration less debilitating; improving a patient's physical or mental well-being. The treatment or amelioration of symptoms can be based on objective or subjective parameters; including the results of a physical examination, neuropsychiatric exams, and/or a psychiatric evaluation. The term "treating," and conjugations thereof, include prevention of an injury, pathology, condition, or disease.

An "effective amount" is an amount sufficient to accomplish a stated purpose (e.g. achieve the effect for which it is administered, treat a disease, reduce one or more symptoms of a disease or condition, and the like). An example of an "effective amount" is an amount sufficient to contribute to the treatment, prevention, or reduction of a symptom or symptoms of a disease, which could also be referred to as a "therapeutically effective amount." A "reduction" of a symptom or symptoms (and grammatical equivalents of this phrase) means decreasing of the severity or frequency of the symptom(s), or elimination of the symptom(s). A "prophylactically effective amount" of a drug is an amount of a drug that, when administered to a subject, will have the intended prophylactic effect, e.g., preventing or delaying the onset (or reoccurrence) of an injury, disease, pathology or condition, or reducing the likelihood of the onset (or reoccurrence) of an injury, disease, pathology, or condition, or their symptoms. The full prophylactic effect does not necessarily occur by administration of one dose, and may occur only after administration of a series of doses. Thus, a prophylactically effective amount may be administered in one or more administrations. The exact amounts will depend on the purpose of the treatment, and will be ascertainable by one skilled in the art using known techniques (see, e.g., Lieberman, *Pharmaceutical Dosage Forms* (vols. 1-3, 1992); Lloyd, *The Art, Science and Technology of Pharmaceutical Compounding* (1999); Pickar, *Dosage Calculations* (1999); and *Remington: The Science and Practice of Pharmacy,* 20th Edition, 2003, Gennaro, Ed., Lippincott, Williams & Wilkins).

"Subject," "patient," "subject in need thereof" and the like refer to a living organism suffering from or prone to a disease or condition that can be treated by administration of a compound or pharmaceutical composition as provided herein. Non-limiting examples include humans, other mammals, bovines, rats, mice, dogs, monkeys, goat, sheep, cows, deer, and other non-mammalian animals. In embodiments, a subject is human.

As used herein, the term "administering" means oral administration, administration as an inhaled aerosol or as an inhaled dry powder, suppository, topical contact, intravenous, parenteral, intraperitoneal, intramuscular, intralesional, intrathecal, intranasal or subcutaneous administration, or the implantation of a slow-release device, e.g., a mini-osmotic pump, to a subject. Administration is by any route, including parenteral and transmucosal (e.g., buccal, sublingual, palatal, gingival, nasal, vaginal, rectal, or transdermal). Parenteral administration includes, e.g., intravenous, intramuscular, intra-arteriole, intradermal, subcutaneous, intraperitoneal, intraventricular, and intracranial. Other modes of delivery include, but are not limited to, the use of liposomal formulations, intravenous infusion, transdermal patches, etc. By "co-administer" it is meant that a composition described herein is administered at the same time, just prior to, or just after the administration of one or more additional therapies, for example cancer therapies such as chemotherapy, hormonal therapy, radiotherapy, or immunotherapy. The compound of the invention can be administered alone or can be coadministered to the patient. Coadministration is meant to include simultaneous or sequential administration of the compound individually or in combination (more than one compound or agent). The compositions of the present invention can be delivered transdermally, by a topical route, formulated as applicator sticks, solutions, suspensions, emulsions, gels, creams, ointments, pastes, jellies, paints, powders, and aerosols. Oral preparations include tablets, pills, powder, dragees, capsules, liquids, lozenges, cachets, gels, syrups, slurries, suspensions, etc., suitable for ingestion by the patient. Solid form preparations include powders, tablets, pills, capsules, cachets, suppositories, and dispersible granules. Liquid form preparations include solutions, suspensions, and emulsions, for example, water or water/propylene glycol solutions. The compositions of the present invention may additionally include components to provide sustained release and/or comfort. Such components include high molecular weight, anionic mucomimetic polymers, gelling polysaccharides and finely-divided drug carrier substrates. These components are discussed in greater detail in U.S. Pat. Nos. 4,911,920; 5,403,841; 5,212,162; and 4,861,760. The entire contents of these patents are incorporated herein by reference in their entirety for all purposes. The compositions of the present invention can also be delivered as microspheres for slow release in the body. For example, microspheres can be administered via intradermal injection of drug-containing microspheres, which slowly release subcutaneously (see Rao, J. Biomater Sci. Polym. Ed. 7:623-645, 1995; as biodegradable and injectable gel formulations (see, e.g., Gao Pharm. Res. 12:857-863, 1995); or, as microspheres for oral administration (see, e.g., Eyles, J. Pharm. Pharmacol. 49:669-674, 1997). In another embodiment, the formulations of the compositions of the present invention can be delivered by the use of liposomes which fuse with the cellular membrane or are endocytosed, i.e., by employing receptor ligands attached to the liposome, that bind to surface membrane protein receptors of the cell resulting in endocytosis. By using liposomes, particularly where the liposome surface carries receptor ligands specific for target cells, or are otherwise preferentially directed to a specific organ, one can focus the delivery of the compositions of the present invention into the target cells in vivo. (See, e.g., Al-Muhammed, J. Microencapsul. 13:293-306, 1996; Chonn, Curr. Opin. Biotechnol. 6:698-708, 1995; Ostro, Am. J. Hosp. Pharm. 46:1576-1587, 1989).

The terms "disease associated with aberrant Aβ levels," "neurodegenerative proteinopathies" and the like refer, in the context of Aβ peptide, to any condition characterized by an abnormal amount of at least one species of Aβ peptide (such as $A\beta_{43}$, $A\beta_{42}$, $A\beta_{40}$, $A\beta_{39}$, $A\beta_{38}$, $A\beta_{37}$, $A\beta_{34}$, etc.); by an abnormal relative amount of different species of Aβ peptides (such as the ratio of $A\beta_{42}$ to $A\beta_{40}$); by an abnormal amount, or relative amount, of Aβ in a particular form (such as monomeric, oligomeric, or fibrillar form; in solution or aggregated in a plaque; in a particular conformation, etc.); and/or by an abnormal amount, or relative amount, of Aβ in a particular location (such as intracellular, membrane-associated or extracellular location, or in a particular tissue or body fluid). The abnormal amount of one or more Aβ peptides, Aβ forms and/or Aβ can be relative to a condition that is a normal, non-disease state. Diseases and disorders characterized by altered Aβ levels are known in the art and/or described herein, and include, for example, Down syndrome, Alzheimer's disease (AD), diffuse Lewy body disease, Hereditary Cerebral Hemorrhage with Amyloidosis-Dutch Type (HCHWA-D), cerebral amyloid angiopathy (CAA), and mild cognitive impairment (MCI). Embodiments of the invention include methods of treating any disease associated with aberrant Aβ levels, such as AD. Compounds of the present invention can be administered to a subject to treat (including to prevent or to ameliorate) conditions associated with altered Aβ production, fibril formation/deposition, degradation and/or clearance, or any altered isoform of Aβ.

The term "amyloid-beta" or "Aβ" refers to a peptide from a human or other species that (a) results from processing or cleavage of an APP-CTF that is amyloidogenic, (b) is one of the peptide constituents of β-amyloid plaques, (c) is the 42-amino acid sequence of Aβ (GenBank Accession No. P05067), (d) is a fragment of a peptide as set forth in (a), (b) or (c), and/or (e) contains one or more additions, deletions or substitutions relative to (a), (b), (c) or (d). Aβ is also referred to in the art as βAP, AβP, A4 or βA4. Aβ peptides derived from proteolysis of an APP-CTF, generally are about 4.2 kD proteins and are typically 39 to 43 amino acids in length, depending on the carboxy-terminal end-point, which exhibits heterogeneity. However, Aβ peptides containing less than 39 amino acids, e.g., $A\beta_{38}$, $A\beta_{37}$, and $A\beta_{34}$, also may occur.

Aβ peptides can be produced in an amyloidogenic APP processing pathway in which APP is cleaved by β-secretase (BACE) and one or more gamma-secretase activities. Aβ peptides include those but are not limited to those that begin at position 672 of APP770 and those that begin at position 682 of APP770 (see, for example, GenBank Accession No. P05067). Generally, as used herein, "Aβ" includes any and all Aβ peptides, unless the amino acid residues are specified, such as, for example, 1-43 ($A\beta_{43}$), 1-42 ($A\beta_{42}$), 1-40 ($A\beta_{40}$), 1-39 ($A\beta_{39}$), 1-38 ($A\beta_{38}$), 1-37 ($A\beta_{37}$), 1-34 ($A\beta_{34}$). Additionally amino-terminally-truncated Aβ peptides exists such as 11-43, 11-42, 11-40, 11-39, 11-38, 11-37, 11-34, and other. The various Aβ peptides of differing lengths are referred to herein as "species" of Aβ.

The term "amyloid precursor protein" or "APP" refers to a protein that can be proteolytically processed or cleaved by one or more processing or cleavage reactions to produce Aβ. APP includes all isoforms that are generated by alternative splicing, which can be typically distinguished by the number of amino acids in the particular isoform. For example, APP embraces APP695, APP751, and APP770. Other isoforms of APP include, for example, APP714, L-APP752, L-APP733, L-APP696, L-APP677, APP563, and APP365.

APP also includes all isoforms containing mutations found in families with AD and other amyloidosis conditions. For example, these mutations include the Swedish double mutation; the London mutation, the Indiana mutation, the Austrian mutation, the Iranian mutation, the French mutation, the German mutation, the Florida mutation, the Australian mutation, the Flemish mutation, the Dutch mutation, the Arctic mutation, the Italian mutation, and the Iowa mutation, and the amyloidsis-Dutch type mutation, all as known in the art.

The term "APP" further includes proteins containing one or more additions, deletions or substitutions relative to the isoforms described above, and APP proteins from humans and other species. Unless a specific isoform is specified, APP when used herein generally refers to any and all isoforms of APP, with or without mutations, from any species.

The term "amyloid precursor protein fragment" refers to any portion of an APP that can be processed or cleaved, by one or more processing or cleavage reactions, to produce Aβ. Amyloid precursor protein fragments of APP generally contain either a beta-secretase cleavage site which, when cleaved, generates the N-terminus of Aβ, a gamma-secretase cleavage site which, when cleaved, generates the C-terminus of Aβ or both a beta- and a gamma-secretase cleavage site. Exemplary amyloid precursor fragments include the APP C-terminal fragments designated C99 and C83, as well as portions thereof lacking some or all C-terminal residues that normally reside in the cytosol.

The term "source of amyloid precursor protein (APP), amyloid precursor fragment thereof and/or Aβ" refers to any in vivo, ex vivo or in vitro substance containing APP, amyloid precursor fragment thereof and/or AB. For example, a "source" can be a live organism (including a human patient, or a laboratory or veterinary animal, such as dog, pig, cow, horse, rat or mice), a sample therefrom (such as a tissue or body fluid, or extract thereof), a cell (such as a primary cell or cell line, or extract thereof), extracellular medium or matrix or milieu, or isolated protein.

II. Compounds

In a first aspect, there is provided a compound having the formula:

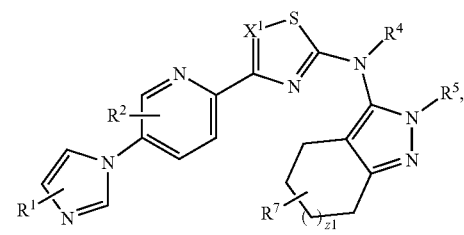

(I)

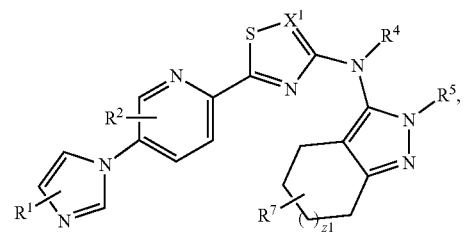

(II)

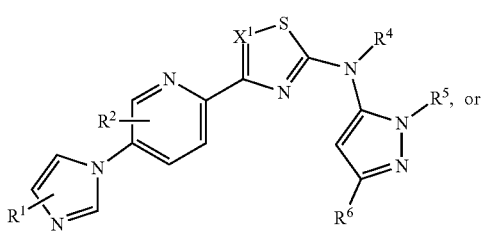

(III)

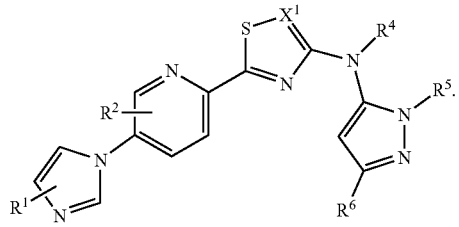

(IV)

For Formulae (I)-(IV), z1 is 0, 1 or 2.

$X^1$ is $C(R^3)$ or N.

$R^1$ is hydrogen, halogen, —$N_3$, —$CF_3$, —$CCl_3$, —$CBr_3$, —$CI_3$, —CN, —CHO, —$OR^{1A}$, —$NR^{1A}R^{1B}$, —$COOR^{1A}$, —$C(O)NR^{1A}R^{1B}$, —$NO_2$, —$SR^{1A}$, —$S(O)_{n1}OR^{1A}$, —$S(O)_{n1}NR^{1A}R^{1B}$, —$NHNR^{1A}R^{1B}$, —$ONR^{1A}R^{1B}$, —NHC(O)NHNR$^{1A}R^{1B}$, substituted or unsubstituted alkyl, substituted or unsubstituted heteroalkyl, substituted or unsubstituted cycloalkyl, substituted or unsubstituted heterocycloalkyl, substituted or unsubstituted aryl, or substituted or unsubstituted heteroaryl.

$R^2$ is hydrogen, halogen, —$N_3$, —$CF_3$, —$CCl_3$, —$CBr_3$, —$CI_3$, —CN, —CHO, —$OR^{2A}$, —$NR^{2A}R^{2B}$, —$COOR^{2A}$, —$C(O)NR^{2A}R^{2B}$, —$NO_2$, —$SR^{2A}$, —$S(O)_{n2}R^{2A}$, —$S(O)_{n2}OR^{2A}$, —$S(O)_{n2}NR^{2A}R^{2B}$, —$NHNR^{2A}R^{2B}$, —$ONR^{2A}R^{2B}$, —NHC(O)NHNR$^{2A}R^{2B}$, substituted or unsubstituted alkyl, substituted or unsubstituted heteroalkyl, substituted or unsubstituted cycloalkyl, substituted or unsubstituted heterocycloalkyl, substituted or unsubstituted aryl, or substituted or unsubstituted heteroaryl.

$R^3$ is hydrogen, halogen, —$N_3$, —$CF_3$, —$CCl_3$, —$CBr_3$, —$CI_3$, —CN, —CHO, —$OR^{3A}$, —$NR^{3A}R^{3B}$, —$COOR^{3A}$, —$C(O)NR^{3A}R^{3B}$, —$NO_2$, —$SR^{3A}$, —$S(O)_{n3}R^{3A}$, —$S(O)_{n3}OR^{3A}$, —$S(O)_{n3}ONR^{3A}R^{3B}$, —$NHNR^{3A}R^{3B}$, —$ONR^{3A}R^{3B}$, —NHC(O)NHNR$^{3A}R^{3B}$, substituted or unsubstituted alkyl, substituted or unsubstituted heteroalkyl, substituted or unsubstituted cycloalkyl, substituted or unsubstituted heterocycloalkyl, substituted or unsubstituted aryl, or substituted or unsubstituted heteroaryl.

$R^4$ is hydrogen, halogen, —$N_3$, —$CF_3$, —$CCl_3$, —$CBr_3$, —$CI_3$, —CN, —CHO, —$OR^{4A}$, —$NR^{4A}R^{4B}$, —$COOR^{4A}$, —$C(O)NR^{4A}R^{4B}$, —$NO_2$, —$SR^{4A}$, —$S(O)_{n4}R^{4A}$, —$S(O)_{n4}OR^{4A}$, —$S(O)_{n4}NR^{4A}R^{4B}$, —$NHNR^{4A}R^{4B}$, —$ONR^{4A}R^{4B}$, —NHC(O)NHNR$^{4A}R^{4B}$, substituted or unsubstituted alkyl, substituted or unsubstituted heteroalkyl, substituted or unsubstituted cycloalkyl, substituted or unsubstituted heterocycloalkyl, substituted or unsubstituted aryl, or substituted or unsubstituted heteroaryl.

$R^5$ is hydrogen, halogen, —$N_3$, —$CF_3$, —$CCl_3$, —$CBr_3$, —$CI_3$, —CN, —CHO, —$OR^{5A}$, —$NR^{5A}R^{5B}$, —$COOR^{5A}$, —$C(O)NR^{5A}R^{5B}$, —$NO_2$, —$SR^{5A}$, —$S(O)_{n5}R^{5A}$, —$S(O)_{n5}OR^{5A}$, —$S(O)_{n5}NR^{5A}R^{5B}$, —$NHNR^{5A}R^{5B}$, —$ONR^{5A}R^{5B}$, —NHC(O)NHNR$^{5A}R^{5B}$, substituted or unsubstituted alkyl, substituted or unsubstituted heteroalkyl, substituted or unsubstituted cycloalkyl, substituted or unsubstituted heterocycloalkyl, substituted or unsubstituted aryl, or substituted or unsubstituted heteroaryl, wherein $R^4$ and $R^5$ are optionally joined together to form a substituted or unsubstituted heterocycloalkyl, or substituted or unsubstituted heteroaryl.

$R^6$ is —$CF_3$, substituted or unsubstituted cyclopropyl, or substituted or unsubstituted cyclobutyl.

$R^7$ is independently hydrogen, halogen, —$N_3$, —$CF_3$, —$CCl_3$, —$CBr_3$, —$CI_3$, —CN, —CHO, —$OR^{7A}$, —$NR^{7A}R^{7B}$, —$COOR^{7A}$, —$C(O)NR^{7A}R^{7B}$, —$NO_2$, —SR$^{7A}$, —S(O)$_{n7}$R$^{7A}$, —S(O)$_{n7}$OR$^{7A}$, —S(O)$_{n7}$NR$^{7A}$R$^{7B}$, —NHNR$^{7A}$R$^{7B}$, —ONR$^{7A}$R$^{7B}$, —NHC(O)NHNR$^{7A}$R$^{7B}$, substituted or unsubstituted alkyl, substituted or unsubstituted heteroalkyl, substituted or unsubstituted cycloalkyl, substituted or unsubstituted heterocycloalkyl, substituted or unsubstituted aryl, or substituted or unsubstituted heteroaryl.

R$^{1A}$, R$^{1B}$, R$^{2A}$, R$^{2B}$, R$^{3A}$, R$^{3B}$, R$^{4A}$, R$^{4B}$, R$^{5A}$, R$^{5B}$, R$^{7A}$ and R$^{7B}$ are independently hydrogen, substituted or unsubstituted alkyl, substituted or unsubstituted heteroalkyl, substituted or unsubstituted cycloalkyl, substituted or unsubstituted heterocycloalkyl, substituted or unsubstituted aryl, or substituted or unsubstituted heteroaryl.

n1, n2, n3, n4, n5 and n7 are independently 1 or 2.

In embodiments, the compound having the structure of Formula (I) is not

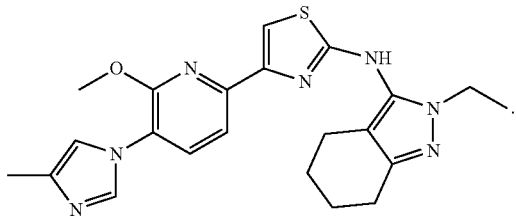 [SMILES: CCn1nc2c(c1Nc1nc(-c3ccc(-n4cnc(C)c4)c(OC)n3)cs1)CCCC2]

In embodiments of the compound with structure of Formula (I)-(IV), R$^1$ is hydrogen, halogen, —N$_3$, —CF$_3$, —CCl$_3$, —CBr$_3$, —CI$_3$, —CN, —CHO, —OR$^{1A}$, —NR$^{1A}$R$^{1B}$, —COOR$^{1A}$, —C(O)NR$^{1A}$R$^{1B}$, —NO$_2$, —SR$^{1A}$, —S(O)$_{n1}$R$^{1A}$, —S(O)$_{n1}$OR$^{1A}$, —S(O)$_{n1}$NR$^{1A}$R$^{1B}$, —NHNR$^{1A}$R$^{1B}$, —ONR$^{1A}$R$^{1B}$, —NHC(O)NHNR$^{1A}$R$^{1B}$, unsubstituted alkyl, unsubstituted heteroalkyl, unsubstituted cycloalkyl, unsubstituted heterocycloalkyl, unsubstituted aryl, or unsubstituted heteroaryl.

In embodiments, R$^2$ is hydrogen, halogen, —N$_3$, —CF$_3$, —CCl$_3$, —CBr$_3$, —CI$_3$, —CN, —CHO, —OR$^{2A}$, —NR$^{2A}$R$^{2B}$, —COOR$^{2A}$, —C(O)NR$^{2A}$R$^{2B}$, —NO$_2$, —SR$^{2A}$, —S(O)$_{n2}$R$^{2A}$, —S(O)$_{n2}$OR$^{2A}$, —S(O)$_{n2}$NR$^{2A}$R$^{2B}$, —NHNR$^{2A}$R$^{2B}$, —ONR$^{2A}$R$^{2B}$, —NHC(O)NHNR$^{2A}$R$^{2B}$, unsubstituted alkyl, unsubstituted heteroalkyl, unsubstituted cycloalkyl, unsubstituted heterocycloalkyl, unsubstituted aryl, or unsubstituted heteroaryl.

In embodiments, R$^3$ is hydrogen, halogen, —N$_3$, —CF$_3$, —CCl$_3$, —CBr$_3$, —CI$_3$, —CN, —CHO, —OR$^{3A}$, —NR$^{3A}$R$^{3B}$, —COOR$^{3A}$, —C(O)NR$^{3A}$R$^{3B}$, —NO$_2$, —SR$^{3A}$, —S(O)$_{n3}$R$^{3A}$, —S(O)$_{n3}$OR$^{3A}$, —S(O)$_{n3}$NR$^{3A}$R$^{3B}$, —NHNR$^{3A}$R$^{3B}$, —ONR$^{3A}$R$^{3B}$, —NHC(O)NHNR$^{3A}$R$^{3B}$, unsubstituted alkyl, unsubstituted heteroalkyl, unsubstituted cycloalkyl, unsubstituted heterocycloalkyl, unsubstituted aryl, or unsubstituted heteroaryl.

In embodiments, R$^4$ is hydrogen, halogen, —N$_3$, —CF$_3$, —CCl$_3$, —CBr$_3$, —CI$_3$, —CN, —CHO, —OR$^{4A}$, —NR$^{4A}$R$^{4B}$, —COOR$^{4A}$, —C(O)NR$^{4A}$R$^{4B}$, —NO$_2$, —SR$^{4A}$, —S(O)$_{n4}$R$^{4A}$, —S(O)$_{n4}$OR$^{4A}$, —S(O)$_{n4}$NR$^{4A}$R$^{4B}$, —NHNR$^{4A}$R$^{4B}$, —ONR$^{4A}$R$^{4B}$, —NHC(O)NHNR$^{4A}$R$^{4B}$, unsubstituted alkyl, unsubstituted heteroalkyl, unsubstituted cycloalkyl, unsubstituted heterocycloalkyl, unsubstituted aryl, or unsubstituted heteroaryl.

In embodiments, R$^5$ is hydrogen, halogen, —N$_3$, —CF$_3$, —CCl$_3$, —CBr$_3$, —CI$_3$, —CN, —CHO, —OR$^{5A}$, —NR$^{5A}$R$^{5B}$, —COOR$^{5A}$, —C(O)NR$^{5A}$R$^{5B}$, —NO$_2$, —SR$^{5A}$, —S(O)$_{n5}$R$^{5A}$, —S(O)$_{n5}$OR$^{5A}$, —S(O)$_{n5}$NR$^{5A}$R$^{5B}$, —NHNR$^{5A}$R$^{5B}$, —ONR$^{5A}$R$^{5B}$, —NHC(O)NHNR$^{5A}$R$^{5B}$, unsubstituted alkyl, unsubstituted heteroalkyl, unsubstituted cycloalkyl, unsubstituted heterocycloalkyl, unsubstituted aryl, or unsubstituted heteroaryl, wherein R$^4$ and R$^5$ are optionally joined together to form a unsubstituted heterocycloalkyl, or unsubstituted heteroaryl.

In embodiments, R$^6$ is —CF$_3$, substituted or unsubstituted cyclopropyl, or substituted or unsubstituted cyclobutyl.

In embodiments, R$^7$ is independently hydrogen, halogen, —N$_3$, —CF$_3$, —CCl$_3$, —CBr$_3$, —CI$_3$, —CN, —CHO, —OR$^{7A}$, —NR$^{7A}$R$^{7B}$, —COOR$^{7A}$, —C(O)NR$^{7A}$R$^{7B}$, —NO$_2$, —SR$^{7A}$, —S(O)$_{n7}$R$^{7A}$, —S(O)$_{n7}$OR$^{7A}$, —S(O)$_{n7}$NR$^{7A}$R$^{7B}$, —NHNR$^{7A}$R$^{7B}$, —ONR$^{7A}$R$^{7B}$, —NHC(O)NHNR$^{7A}$R$^{7B}$, unsubstituted alkyl, unsubstituted heteroalkyl, unsubstituted cycloalkyl, unsubstituted heterocycloalkyl, unsubstituted aryl, or unsubstituted heteroaryl.

In embodiments, R$^{1A}$, R$^{1B}$, R$^{2A}$, R$^{2B}$, R$^{3A}$, R$^{3B}$, R$^{4A}$, R$^{4B}$, R$^{5A}$, R$^{5B}$, R$^{7A}$, R$^{7B}$, R$^{8A}$, R$^{8B}$, R$^{9A}$, R$^{9B}$, R$^{10A}$ or R$^{10B}$ are independently hydrogen, unsubstituted alkyl, unsubstituted heteroalkyl, unsubstituted cycloalkyl, unsubstituted heterocycloalkyl, unsubstituted aryl, or unsubstituted heteroaryl.

In embodiments of the compound with structure of Formula (I)-(IV), R$^1$ is hydrogen, halogen, —N$_3$, —CF$_3$, —CCl$_3$, —CBr$_3$, —CI$_3$, —CN, —CHO, —OR$^{1A}$, —NR$^{1A}$R$^{1B}$, —COOR$^{1A}$, —C(O)NR$^{1A}$R$^{1B}$, —NO$_2$, —SR$^{1A}$, —S(O)$_{n1}$R$^{1A}$, —S(O)$_{n1}$OR$^{1A}$, —S(O)$_{n1}$NR$^{1A}$R$^{1B}$, —NHNR$^{1A}$R$^{1B}$, —ONR$^{1A}$R$^{1B}$, —NHC(O)NHNR$^{1A}$R$^{1B}$, substituted or unsubstituted alkyl, R$^{1.41}$-substituted or unsubstituted heteroalkyl, R$^{1.41}$-substituted or unsubstituted cycloalkyl, R$^{1.41}$-substituted or unsubstituted heterocycloalkyl, R$^{1.41}$-substituted or unsubstituted aryl, or R$^{1.41}$-substituted or unsubstituted heteroaryl. R$^{1.41}$ is independently halogen, —CN, —CF$_3$, —OH, —NH$_2$, —SO$_2$, —COOH, R$^{1.42}$-substituted or unsubstituted alkyl, R$^{1.42}$-substituted or unsubstituted heteroalkyl, R$^{1.42}$-substituted or unsubstituted cycloalkyl, R$^{1.42}$-substituted or unsubstituted heterocycloalkyl, R$^{1.42}$-substituted or unsubstituted aryl, or R$^{1.42}$-substituted or unsubstituted heteroaryl. R$^{1.42}$ is independently halogen, —CN, —CF$_3$, —OH, —NH$_2$, —SO$_2$, —COOH, R$^{1.43}$-substituted or unsubstituted alkyl, R$^{1.43}$-substituted or unsubstituted heteroalkyl, R$^{1.43}$-substituted or unsubstituted cycloalkyl, R$^{1.43}$-substituted or unsubstituted heterocycloalkyl, R$^{1.43}$-substituted or unsubstituted aryl, or R$^{1.43}$-substituted or unsubstituted heteroaryl. R$^{1.43}$ is independently halogen, —CN, —CF$_3$, —OH, —NH$_2$, —SO$_2$, —COOH, unsubstituted alkyl, unsubstituted heteroalkyl, unsubstituted cycloalkyl, unsubstituted heterocycloalkyl, unsubstituted aryl, or unsubstituted heteroaryl.

In embodiments, R$^2$ is hydrogen, halogen, —N$_3$, —CF$_3$, —CCl$_3$, —CBr$_3$, —CI$_3$, —CN, —CHO, —OR$^{2A}$, —NR$^{2A}$R$^{2B}$, —COOR$^{2A}$, —C(O)NR$^{2A}$R$^{2B}$, —NO$_2$, —SR$^{2A}$, —S(O)$_{n2}$R$^{2A}$, —S(O)$_{n2}$OR$^{2A}$, —S(O)$_{n2}$NR$^{2A}$R$^{2B}$, —NHNR$^{2A}$R$^{2B}$, —ONR$^{2A}$R$^{2B}$, —NHC(O)NHNR$^{2A}$R$^{2B}$, R$^{2.41}$-substituted or unsubstituted alkyl, R$^{2.41}$-substituted or unsubstituted heteroalkyl, R$^{2.41}$-substituted or unsubstituted cycloalkyl, R$^{2.41}$-substituted or unsubstituted heterocycloalkyl, R$^{2.41}$-substituted aryl, or R$^{2.41}$-substituted or unsubstituted heteroaryl. R$^{2.41}$ is independently halogen, —CN, —CF$_3$, —OH, —NH$_2$, —SO$_2$, —COOH, R$^{2.42}$-substituted or unsubstituted alkyl, R$^{2.42}$-substituted or unsubstituted heteroalkyl, R$^{2.42}$-substituted or unsubstituted cycloalkyl, substituted or unsubstituted heterocycloalkyl, R$^{2.42}$-substituted or unsubstituted aryl, or R$^{2.42}$-substituted or unsubstituted heteroaryl. R$^{2.42}$ is independently halogen, —CN, —CF$_3$, —OH, —NH$_2$, —SO$_2$, —COOH, R$^{2.41}$-substituted or unsubstituted alkyl, R$^{2.43}$-substituted or unsubstituted heteroalkyl, R$^{2.43}$-substituted or unsubstituted cycloalkyl, R$^{2.43}$-substituted or unsubstituted heterocycloalkyl, R$^{2.43}$-substituted or unsubstituted aryl, or R$^{2.43}$-substituted or unsubstituted heteroaryl. R$^{2.43}$ is independently halogen, —CN, —CF$_3$, —OH, —NH$_2$, —SO$_2$, —COOH, unsubstituted alkyl, unsubstituted heteroalkyl, unsubstituted cycloalkyl, unsubstituted heterocycloalkyl, unsubstituted aryl, or unsubstituted heteroaryl.

In embodiments, R$^3$ is hydrogen, halogen, —N$_3$, —CF$_3$, —CCl$_3$, —CBr$_3$, —CI$_3$, —CN, —CHO, —OR$^{3A}$, —NR$^{3A}$R$^{3B}$, —COOR$^{3A}$, —C(O)NR$^{3A}$R$^{3B}$, —NO$_2$, —SR$^{3A}$, —S(O)$_{n3}$R$^{3A}$, —S(O)$_{n3}$OR$^{3A}$, —S(O)$_{n3}$NR$^{3A}$R$^{3B}$, —NHNR$^{3A}$R$^{3B}$, —ONR$^{3A}$R$^{3B}$, —NHC(O)NHNR$^{3A}$R$^{3B}$, R$^{3A1}$-substituted or unsubstituted alkyl, R$^{3A1}$-substituted or unsubstituted heteroalkyl, R$^{3A1}$-substituted or unsubstituted cycloalkyl, R$^{3A1}$-substituted or unsubstituted heterocycloalkyl, R$^{3A1}$-substituted or unsubstituted aryl, or R$^{3A1}$-substituted or unsubstituted heteroaryl. R$^{3A1}$ is independently halogen, —CN, —CF$_3$, —OH, —NH$_2$, —SO$_2$, —COOH, R$^{3A2}$-substituted or unsubstituted alkyl, R$^{3A2}$-substituted or unsubstituted heteroalkyl, R$^{3A2}$-substituted or unsubstituted cycloalkyl, R$^{3A2}$-substituted or unsubstituted heterocycloalkyl, R$^{3A2}$-substituted or unsubstituted aryl, or R$^{3A2}$-substituted or unsubstituted heteroaryl. R$^{3A2}$ is independently halogen, —CN, —CF$_3$, —OH, —NH$_2$, —SO$_2$, —COOH, R$^{3A3}$-substituted or unsubstituted alkyl, R$^{3A3}$-substituted or unsubstituted heteroalkyl, R$^{3A3}$-substituted or unsubstituted cycloalkyl, R$^{3A3}$-substituted or unsubstituted heterocycloalkyl, R$^{3A3}$-substituted or unsubstituted aryl, or R$^{3A3}$-substituted or unsubstituted heteroaryl. R$^{3A3}$ is independently halogen, —CN, —CF$_3$, —OH, —NH$_2$, —SO$_2$, —COOH, unsubstituted alkyl, unsubstituted heteroalkyl, unsubstituted cycloalkyl, unsubstituted heterocycloalkyl, unsubstituted aryl, or unsubstituted heteroaryl.

In embodiments, R$^4$ is hydrogen, halogen, —N$_3$, —CF$_3$, —CCl$_3$, —CBr$_3$, —CI$_3$, —CN, —CHO, —OR$^{4A}$, —NR$^{4A}$R$^{4B}$, —COOR$^{4A}$, —C(O)NR$^{4A}$R$^{4B}$, —NO$_2$, —SR$^{4A}$, —S(O)$_{n4}$R$^{4A}$, —S(O)$_{n4}$OR$^{4A}$, —S(O)$_4$NR$^{4A}$R$^{4B}$, —NHNR$^{4A}$R$^{4B}$, —ONR$^{4A}$R$^{4B}$, —NHC(O)NHNR$^{4A}$R$^{4B}$, R$^{4A1}$-substituted or unsubstituted alkyl, R$^{4A1}$-substituted or unsubstituted heteroalkyl, R$^{4A1}$-substituted or unsubstituted cycloalkyl, R$^{4A1}$-substituted or unsubstituted heterocycloalkyl, R$^{4A1}$-substituted or unsubstituted aryl, or R$^{4A1}$-substituted or unsubstituted heteroaryl. R$^{4A1}$ is independently halogen, —CN, —CF$_3$, —OH, —NH$_2$, —SO$_2$, —COOH, R$^{4A1}$-substituted or unsubstituted alkyl, R$^{4A2}$-substituted or unsubstituted heteroalkyl, R$^{4A2}$-substituted or unsubstituted cycloalkyl, R$^{4A2}$-substituted or unsubstituted heterocycloalkyl, R$^{4A2}$-substituted or unsubstituted aryl, or R$^{4A2}$-substituted or unsubstituted heteroaryl. R$^{4A2}$ is independently halogen, —CN, —CF$_3$, —OH, —NH$_2$, —SO$_2$, —COOH, R$^{4A2}$-substituted or unsubstituted alkyl, R$^{4A3}$-substituted or unsubstituted heteroalkyl, R$^{4A3}$-substituted or unsubstituted cycloalkyl, R$^{4A3}$-substituted or unsubstituted heterocycloalkyl, R$^{4A3}$-substituted or unsubstituted aryl, or R$^{4A3}$-substituted or unsubstituted heteroaryl. R$^{4A3}$ is independently halogen, —CN, —CF$_3$, —OH, —NH$_2$, —SO$_2$, —COOH, unsubstituted alkyl, unsubstituted heteroalkyl, unsubstituted cycloalkyl, unsubstituted heterocycloalkyl, unsubstituted aryl, or unsubstituted heteroaryl.

In embodiments, R$^5$ is hydrogen, halogen, —N$_3$, —CF$_3$, —CCl$_3$, —CBr$_3$, —CI$_3$, —CN, —CHO, —OR$^{5A}$, —NR$^{5A}$R$^{5B}$, —COOR$^{5A}$, —C(O)NR$^{5A}$R$^{5B}$, —NO$_2$, —SR$^{5A}$, —S(O)$_{n5}$R$^{5A}$, —S(O)$_{n5}$OR$^{5A}$, —S(O)$_{n5}$NR$^{5A}$R$^{5B}$, —NHNR$^{5A}$R$^{5B}$, —ONR$^{5A}$R$^{5B}$, —NHC(O)NHNR$^{5A}$R$^{5B}$, R$^{5A1}$-substituted or unsubstituted alkyl, R$^{5A1}$-substituted or unsubstituted heteroalkyl, R$^{5A1}$-substituted or unsubstituted cycloalkyl, R$^{5A1}$-substituted or unsubstituted heterocycloalkyl, R$^{5A1}$-substituted or unsubstituted aryl, or R$^{5A1}$-substituted or unsubstituted heteroaryl, wherein R$^4$ and R$^5$ are optionally joined together to form a substituted or unsubstituted heterocycloalkyl, or substituted or unsubstituted heteroaryl. R$^{5A1}$ is independently halogen, —CN, —CF$_3$, —OH, —NH$_2$, —SO$_2$, —COOH, R$^{5A2}$-substituted or unsubstituted alkyl, R$^{5A2}$-substituted or unsubstituted heteroalkyl, R$^{5A2}$-substituted or unsubstituted cycloalkyl, R$^{5A2}$-substituted or unsubstituted heterocycloalkyl, R$^{5A2}$-substituted or unsubstituted aryl, or R$^{5A2}$-substituted or unsubstituted heteroaryl. R$^{5A2}$ is independently halogen, —CN, —CF$_3$, —OH, —NH$_2$, —SO$_2$, —COOH, R$^{5A3}$-substituted or unsubstituted alkyl, R$^{5A3}$-substituted or unsubstituted heteroalkyl, R$^{5A3}$-substituted or unsubstituted cycloalkyl, R$^{5A3}$-substituted or unsubstituted heterocycloalkyl, R$^{5A3}$-substituted or unsubstituted aryl, or R$^{5A3}$-substituted or unsubstituted heteroaryl. R$^{5A3}$ is independently halogen, —CN, —CF$_3$, —OH, —NH$_2$, —SO$_2$, —COOH, unsubstituted alkyl, unsubstituted heteroalkyl, unsubstituted cycloalkyl, unsubstituted heterocycloalkyl, unsubstituted aryl, or unsubstituted heteroaryl.

In embodiments, R$^6$ is —CF$_3$, R$^{6A1}$-substituted cyclopropyl, or R$^{6A1}$-substituted cyclobutyl. R$^{6A1}$ is independently halogen, —CN, —CF$_3$, —OH, —NH$_2$, —SO$_2$, —COOH, R$^{6A2}$-substituted or unsubstituted alkyl, R$^{6A2}$-substituted or unsubstituted heteroalkyl, R$^{6A2}$-substituted or unsubstituted cycloalkyl, R$^{6A2}$-substituted or unsubstituted heterocycloalkyl, R$^{6A2}$-substituted or unsubstituted aryl, or R$^{6A2}$-substituted or unsubstituted heteroaryl. R$^{6A2}$ is independently halogen, —CN, —CF$_3$, —OH, —NH$_2$, —SO$_2$, —COOH, R$^{6A3}$-substituted or unsubstituted alkyl, R$^{6A3}$-substituted or unsubstituted heteroalkyl, R$^{6A3}$-substituted or unsubstituted cycloalkyl, R$^{6A3}$-substituted or unsubstituted heterocycloalkyl, R$^{6A3}$-substituted or unsubstituted aryl, or R$^{6A3}$-substituted or unsubstituted heteroaryl. R$^{6A3}$ is independently halogen, —CN, —CF$_3$, —OH, —NH$_2$, —SO$_2$, —COOH, unsubstituted alkyl, unsubstituted heteroalkyl, unsubstituted cycloalkyl, unsubstituted heterocycloalkyl, unsubstituted aryl, or unsubstituted heteroaryl.

In embodiments, R$^7$ is independently hydrogen, halogen, —N$_3$, —CF$_3$, —CCl$_3$, —CBr$_3$, —CI$_3$, —CN, —CHO, —OR$^{7A}$, —NR$^{7A}$R$^{7B}$, —COOR$^{7A}$, —C(O)NR$^{7A}$R$^{7B}$, —NO$_2$, —SR$^{7A}$, —S(O)$_{n7}$R$^{7A}$, —S(O)$_{n7}$OR$^{7A}$, —S(O)$_{n7}$NR$^{7A}$R$^{7B}$, —NHNR$^{7A}$R$^{7B}$, —ONR$^{7A}$R$^{7B}$, —NHC(O)NHNR$^{7A}$R$^{7B}$, R$^{7A1}$-substituted or unsubstituted alkyl, R$^{7A1}$-substituted or unsubstituted heteroalkyl, R$^{7A1}$-substituted or unsubstituted cycloalkyl, R$^{7A1}$-substituted or unsubstituted heterocycloalkyl, R$^{7A1}$-substituted or unsubstituted aryl, or R$^{7A1}$-substituted or unsubstituted heteroaryl. R$^{7A1}$ is independently halogen, —CN, —CF$_3$, —OH, —NH$_2$, —SO$_2$, —COOH, R$^{7A2}$-substituted or unsubstituted alkyl, R$^{7A2}$-substituted or unsubstituted heteroalkyl, R$^{7A2}$-substituted or unsubstituted cycloalkyl, R$^{7A2}$-substituted or unsubstituted heterocycloalkyl, R$^{7A2}$-substituted or unsubstituted aryl, or R$^{7A2}$-substituted or unsubstituted heteroaryl. R$^{7A2}$ is independently halogen, —CN, —CF$_3$, —OH, —NH$_2$, —SO$_2$, —COOH, R$^{7A3}$-substituted or unsubstituted alkyl, R$^{7A3}$-substituted or unsubstituted heteroalkyl, R$^{7A3}$-substituted or unsubstituted cycloalkyl, R$^{7A3}$-substituted or unsubstituted heterocycloalkyl, R$^{7A3}$-substituted or unsubstituted aryl, or R$^{7A3}$-substituted or unsubstituted heteroaryl. R$^{7A3}$ is independently halogen, —CN, —CF$_3$, —OH, —NH$_2$, —SO$_2$, —COOH, unsubstituted alkyl, unsubstituted heteroalkyl, unsubstituted cycloalkyl, unsubstituted heterocycloalkyl, unsubstituted aryl, or unsubstituted heteroaryl.

In embodiments, R$^{1A}$, R$^{1B}$, R$^{2A}$, R$^{2B}$, R$^{3A}$, R$^{3B}$, R$^{4A}$, R$^{4B}$, R$^{5A}$, R$^{5B}$, R$^{7A}$, R$^{7B}$, R$^{8A}$, R$^{8B}$, R$^{9A}$, R$^{9B}$, R$^{10A}$ and R$^{10B}$ are independently hydrogen, R$^{11A1}$-substituted or unsubstituted alkyl, R$^{11A1}$-substituted or unsubstituted heteroalkyl, R$^{11A1}$-substituted or unsubstituted cycloalkyl, R$^{11A1}$-substituted or unsubstituted heterocycloalkyl, $R^{11.A1}$-substituted or unsubstituted aryl, or $R^{11.A1}$-substituted or unsubstituted heteroaryl. $R^{11.A1}$ is independently halogen, —CN, —CF$_3$, —OH, —NH$_2$, —SO$_2$, —COOH, unsubstituted alkyl, unsubstituted heteroalkyl, unsubstituted cycloalkyl, unsubstituted heterocycloalkyl, unsubstituted aryl, or unsubstituted heteroaryl.

In embodiments, one or more of $R^1$, $R^2$, $R^3$, $R^4$, $R^5$, $R^7$, $R^8$, $R^9$ or $R^{19}$ is independently a size-limited substituent or a lower substituent. In embodiments, $R^1$, $R^2$, $R^3$, $R^4$, $R^5$, $R^7$, $R^8$, $R^9$ or $R^{10}$ is independently substituted or unsubstituted $C_1$-$C_{10}$ (e.g., $C_1$-$C_6$) alkyl, substituted or unsubstituted 2 to 10 membered (e.g., 2 to 6 membered) heteroalkyl, substituted or unsubstituted $C_3$-$C_8$ (e.g., $C_5$-$C_7$) cycloalkyl, substituted or unsubstituted 3 to 8 membered (e.g., 3 to 6 membered) heterocycbalkyl, substituted or unsubstituted $C_5$-$C_{10}$ (e.g., $C_5$-$C_6$) aryl, or substituted or unsubstituted 5 to 8 membered (e.g., 5 to 6 membered) heteroaryl.

In embodiments, one or more of $R^{1.A1}$, $R^{1.A2}$, or $R^{1.A3}$ is independently a size-limited substituent or a lower substituent. In embodiments, $R^{1.A1}$ is independently $R^{1.A2}$-substituted or unsubstituted $C_1$-$C_{10}$ (e.g., $C_1$-$C_6$) alkyl, $R^{1.A2}$-substituted or unsubstituted 2 to 10 membered (e.g., 2 to 6 membered) heteroalkyl, $R^{1.A2}$-substituted or unsubstituted $C_3$-$C_8$ (e.g., $C_5$-$C_7$) cycloalkyl, $R^{1.A2}$-substituted or unsubstituted 3 to 8 membered (e.g., 3 to 6 membered) heterocycloalkyl, $R^{1.A2}$-substituted or unsubstituted $C_5$-$C_{10}$ (e.g., $C_5$-$C_6$) aryl, or $R^{1.A2}$-substituted or unsubstituted 5 to 8 membered (e.g., 5 to 6 membered) heteroaryl. In embodiments, $R^{1.A2}$ is independently $R^{1.A3}$-substituted or unsubstituted $C_1$-$C_{10}$ (e.g., $C_1$-$C_6$) alkyl, $R^{1.A3}$-substituted or unsubstituted 2 to 10 membered (e.g., 2 to 6 membered) heteroalkyl, $R^{1.A3}$-substituted or unsubstituted $C_3$-$C_8$ (e.g., $C_5$-$C_7$) cycloalkyl, $R^{1.A3}$-substituted or unsubstituted 3 to 8 membered (e.g., 3 to 6 membered) heterocycloalkyl, $R^{1.A3}$-substituted or unsubstituted $C_5$-$C_{10}$ (e.g., $C_5$-$C_6$) aryl, or $R^{1.A3}$-substituted or unsubstituted 5 to 8 membered (e.g., 5 to 6 membered) heteroaryl. In embodiments, $R^{1.A3}$ is independently unsubstituted $C_1$-$C_{10}$ (e.g., $C_1$-$C_6$) alkyl, unsubstituted 2 to 10 membered (e.g., 2 to 6 membered) heteroalkyl, unsubstituted $C_3$-$C_8$ (e.g., $C_5$-$C_7$) cycloalkyl, unsubstituted 3 to 8 membered (e.g., 3 to 6 membered) heterocycbalkyl, unsubstituted $C_5$-$C_{10}$ (e.g., $C_5$-$C_6$) aryl, or unsubstituted 5 to 8 membered (e.g., 5 to 6 membered) heteroaryl.

In embodiments, one or more of $R^{2.A1}$, $R^{2.A2}$, or $R^{2.A3}$ is independently a size-limited substituent or a lower substituent. In embodiments, $R^{2.A1}$ is independently $R^{2.A1}$-substituted or unsubstituted $C_1$-$C_{10}$ (e.g., $C_1$-$C_6$) alkyl, $R^{2.A1}$-substituted or unsubstituted 2 to 10 membered (e.g., 2 to 6 membered) heteroalkyl, $R^{2.A2}$-substituted or unsubstituted $C_3$-$C_6$ (e.g., $C_5$-$C_7$) cycloalkyl, $R^{2.A2}$-substituted or unsubstituted 3 to 8 membered (e.g., 3 to 6 membered) heterocycloalkyl, $R^{2.A2}$-substituted or unsubstituted $C_5$-$C_{10}$ (e.g., $C_5$-$C_6$) aryl, or $R^{2.A2}$-substituted or unsubstituted 5 to 8 membered (e.g., 5 to 6 membered) heteroaryl. In embodiments, $R^{2.A2}$ is independently $R^{2.A3}$-substituted or unsubstituted $C_1$-$C_{10}$ (e.g., $C_1$-$C_6$) alkyl, $R^{2.A3}$-substituted or unsubstituted 2 to 10 membered (e.g., 2 to 6 membered) heteroalkyl, $R^{2.A3}$-substituted or unsubstituted $C_3$-$C_8$ (e.g., $C_5$-$C_7$) cycloalkyl, $R^{2.A1}$-substituted or unsubstituted 3 to 8 membered (e.g., 3 to 6 membered) heterocycloalkyl, $R^{2.A3}$-substituted or unsubstituted $C_5$-$C_{10}$ (e.g., $C_5$-$C_6$) aryl, or $R^{2.A3}$-substituted or unsubstituted 5 to 8 membered (e.g., 5 to 6 membered) heteroaryl. In embodiments, $R^{2.A3}$ is independently unsubstituted (e.g., $C_1$-$C_6$) alkyl, unsubstituted 2 to 10 membered (e.g., 2 to 6 membered) heteroalkyl, unsubstituted $C_3$-$C_8$ (e.g. $C_5$-$C_7$) cycloalkyl, unsubstituted 3 to 8 membered (e.g., 3 to 6 membered) heterocycbalkyl, unsubstituted $C_5$-$C_{10}$ (e.g., $C_5$-$C_6$) aryl, or unsubstituted 5 to 8 membered (e.g., 5 to 6 membered) heteroaryl.

In embodiments, one or more of $R^{3.A1}$, $R^{3.A2}$, or $R^{3.A3}$ is a size-limited substituent or a lower substituent. In embodiments, $R^{3.A1}$ is independently $R^{3.A2}$-substituted or unsubstituted $C_1$-$C_{13}$ (e.g., $C_1$-$C_6$) alkyl, $R^{3.A2}$-substituted or unsubstituted 2 to 10 membered (e.g., 2 to 6 membered) heteroalkyl, $R^{3.A2}$-substituted or unsubstituted $C_3$-$C_8$ (e.g., $C_5$-$C_7$) cycloalkyl, $R^{3.A2}$-substituted or unsubstituted 3 to 8 membered (e.g., 3 to 6 membered) heterocycloalkyl, $R^{3.A2}$-substituted or unsubstituted $C_5$-$C_{10}$ (e.g., $C_5$-$C_6$) aryl, or $R^{3.A2}$-substituted or unsubstituted 5 to 8 membered (e.g., 5 to 6 membered) heteroaryl. In embodiments, $R^{3.A2}$ is independently $R^{3.A3}$-substituted or unsubstituted $C_1$-$C_{10}$ (e.g., $C_1$-$C_6$) alkyl, $R^{3.A3}$-substituted or unsubstituted 2 to 10 membered (e.g., 2 to 6 membered) heteroalkyl, $R^{3.A3}$-substituted or unsubstituted $C_3$-$C_8$ (e.g., $C_5$-$C_7$) cycloalkyl, $R^{3.A3}$-substituted or unsubstituted 3 to 8 membered (e.g., 3 to 6 membered) heterocycbalkyl, $R^{3.A3}$-substituted or unsubstituted $C_5$-$C_{10}$ (e.g., $C_5$-$C_6$) aryl, or $R^{3.A3}$-substituted or unsubstituted 5 to 8 membered (e.g., 5 to 6 membered) heteroaryl. In embodiments, $R^{3.A3}$ is independently unsubstituted $C_1$-$C_{10}$ (e.g., $C_1$-$C_6$) alkyl, unsubstituted 2 to 10 membered (e.g., 2 to 6 membered) heteroalkyl, unsubstituted $C_5$-$C_8$ (e.g., $C_5$-$C_7$) cycloalkyl, unsubstituted 3 to 8 membered (e.g., 3 to 6 membered) heterocycloalkyl, unsubstituted $C_5$-$C_{10}$ (e.g., $C_5$-$C_6$) aryl, or unsubstituted 5 to 8 membered (e.g., 5 to 6 membered) heteroaryl.

In embodiments, one or more of $R^{4.A1}$, $R^{4.A2}$, or $R^{4.A3}$ is independently a size-limited substituent or a lower substituent. In embodiments, $R^{4.A1}$ is independently $R^{4.A2}$-substituted or unsubstituted $C_1$-$C_{10}$ (e.g., $C_1$-$C_6$) alkyl, $R^{4.A2}$-substituted or unsubstituted 2 to 10 membered (e.g., 2 to 6 membered) heteroalkyl, $R^{4.A2}$-substituted or unsubstituted $C_3$-$C_8$ (e.g., $C_5$-$C_7$) cycloalkyl, $R^{4.A2}$-substituted or unsubstituted 3 to 8 membered (e.g., 3 to 6 membered) heterocycloalkyl, $R^{4.A2}$-substituted or unsubstituted (e.g., $C_5$-$C_6$) aryl, or $R^{4.A2}$-substituted or unsubstituted 5 to 8 membered (e.g., 5 to 6 membered) heteroaryl. In embodiments, $R^{4.A2}$ is independently $R^{4.A3}$-substituted or unsubstituted $C_1$-$C_{10}$ (e.g., $C_1$-$C_6$) alkyl, $R^{4.A3}$-substituted or unsubstituted 2 to 10 membered (e.g., 2 to 6 membered) heteroalkyl, $R^{4.A3}$-substituted or unsubstituted $C_3$-$C_8$ (e.g., $C_5$-$C_7$) cycloalkyl, $R^{4.A3}$-substituted or unsubstituted 3 to 8 membered (e.g., 3 to 6 membered) heterocycloalkyl, $R^{4.A3}$-substituted or unsubstituted $C_5$-$C_{10}$ (e.g., $C_5$-$C_6$) aryl, or $R^{4.A3}$-substituted or unsubstituted 5 to 8 membered (e.g., 5 to 6 membered) heteroaryl. In embodiments, $R^{4.A3}$ is independently unsubstituted $C_1$-$C_{10}$ (e.g., $C_1$-$C_6$) alkyl, unsubstituted 2 to 10 membered (e.g., 2 to 6 membered) heteroalkyl, unsubstituted $C_3$-$C_8$ (e.g., $C_5$-$C_7$) cycloalkyl, unsubstituted 3 to 8 membered (e.g., 3 to 6 membered) heterocycbalkyl, unsubstituted $C_5$-$C_{10}$ (e.g., $C_5$-$C_6$) aryl, or unsubstituted 5 to 8 membered (e.g., 5 to 6 membered) heteroaryl.

In embodiments, one or more of $R^{5.A1}$, $R^{5.A2}$, or $R^{5.A3}$ is independently a size-limited substituent or a lower substituent. In embodiments, $R^{5.A2}$ is independently $R^{5.A2}$-substituted or unsubstituted $C_1$-$C_{10}$ (e.g., $C_1$-$C_6$) alkyl, $R^{5.A2}$-substituted or unsubstituted 2 to 10 membered (e.g., 2 to 6 membered)

heteroalkyl, $R^{5A2}$-substituted or unsubstituted $C_3$-$C_8$ (e.g., $C_5$-$C_7$) cycloalkyl, $R^{5A2}$-substituted or unsubstituted 3 to 8 membered (e.g., 3 to 6 membered) heterocycloalkyl, $R^{5A2}$-substituted or unsubstituted $C_5$-$C_{10}$ (e.g., $C_5$-$C_6$) aryl, or $R^{5A2}$-substituted or unsubstituted 5 to 8 membered (e.g., 5 to 6 membered) heteroaryl. In embodiments, $R^{5A2}$ is independently $R^{5A3}$-substituted or unsubstituted $C_1$-$C_{10}$ (e.g., $C_1$-$C_6$) alkyl, $R^{5A3}$-substituted or unsubstituted 2 to 10 membered (e.g., 2 to 6 membered) heteroalkyl, $R^{5A3}$-substituted or unsubstituted $C_3$-$C_8$ (e.g., $C_5$-$C_7$) cycloalkyl, $R^{5A3}$-substituted or unsubstituted 3 to 8 membered (e.g., 3 to 6 membered) heterocycloalkyl, $R^{5A3}$-substituted or unsubstituted $C_5$-$C_{10}$ (e.g., $C_5$-$C_6$) aryl, or $R^{5A3}$-substituted or unsubstituted 5 to 8 membered (e.g., 5 to 6 membered) heteroaryl. In embodiments, $R^{5A3}$ is independently unsubstituted $C_1$-$C_{10}$ (e.g., $C_1$-$C_6$) alkyl, unsubstituted 2 to 10 membered (e.g., 2 to 6 membered) heteroalkyl, unsubstituted $C_3$-$C_8$ (e.g., $C_5$-$C_7$) cycloalkyl, unsubstituted 3 to 8 membered (e.g., 3 to 6 membered) heterocycloalkyl, unsubstituted $C_5$-$C_{10}$ (e.g., $C_5$-$C_6$) aryl, or unsubstituted 5 to 8 membered (e.g., 5 to 6 membered) heteroaryl.

In embodiments, one or more of $R^{6A1}$, $R^{6A2}$, or $R^{6A3}$ is independently a size-limited substituent or a lower substituent. In embodiments, $R^{6A1}$ is independently $R^{6A2}$-substituted or unsubstituted $C_1$-$C_{10}$ (e.g., $C_1$-$C_6$) alkyl, $R^{6A2}$-substituted or unsubstituted 2 to 10 membered (e.g., 2 to 6 membered) heteroalkyl, $R^{6A2}$-substituted or unsubstituted $C_3$-$C_8$ (e.g., $C_5$-$C_7$) cycloalkyl, $R^{6A2}$-substituted or unsubstituted 3 to 8 membered (e.g., 3 to 6 membered) heterocycloalkyl, $R^{6A2}$-substituted or unsubstituted $C_5$-$C_{10}$ (e.g., $C_5$-$C_6$) aryl, or $R^{6A2}$-substituted or unsubstituted 5 to 8 membered (e.g., 5 to 6 membered) heteroaryl. In embodiments, $R^{6A2}$ is independently $R^{6A3}$-substituted or unsubstituted $C_1$-$C_{10}$ (e.g., $C_1$-$C_6$) alkyl, $R^{6A3}$-substituted or unsubstituted 2 to 10 membered (e.g., 2 to 6 membered) heteroalkyl, $R^{6A3}$-substituted or unsubstituted $C_3$-$C_8$ (e.g., $C_5$-$C_7$) cycloalkyl, $R^{6A3}$-substituted or unsubstituted 3 to 8 membered (e.g., 3 to 6 membered) heterocycloalkyl, $R^{6A3}$-substituted or unsubstituted $C_5$-$C_{10}$ (e.g., $C_5$-$C_6$) aryl, or $R^{6A3}$-substituted or unsubstituted 5 to 8 membered (e.g., 5 to 6 membered) heteroaryl. In embodiments, $R^{6A3}$ is independently unsubstituted $C_1$-$C_{10}$ (e.g., $C_1$-$C_6$) alkyl, unsubstituted 2 to 10 membered (e.g., 2 to 6 membered) heteroalkyl, unsubstituted $C_3$-$C_8$ (e.g., $C_5$-$C_7$) cycloalkyl, unsubstituted 3 to 8 membered (e.g., 3 to 6 membered) heterocycbalkyl, unsubstituted $C_5$-$C_{10}$ (e.g., $C_5$-$C_6$) aryl, or unsubstituted 5 to 8 membered (e.g., 5 to 6 membered) heteroaryl.

In embodiments, one or more of $R^{7A1}$, $R^{7A2}$, or $R^{7A3}$ is independently a size-limited substituent or a lower substituent. In embodiments, $R^{7A1}$ is independently $R^{7A2}$-substituted or unsubstituted $C_1$-$C_{10}$ (e.g., $C_1$-$C_6$) alkyl, $R^{7A2}$-substituted or unsubstituted 2 to 10 membered (e.g., 2 to 6 membered) heteroalkyl, $R^{7A2}$-substituted or unsubstituted $C_3$-$C_8$ (e.g., $C_5$-$C_7$) cycloalkyl, $R^{7A2}$-substituted or unsubstituted 3 to 8 membered (e.g., 3 to 6 membered) heterocycloalkyl, $R^{7A2}$-substituted or unsubstituted $C_5$-$C_{10}$ (e.g., $C_5$-$C_6$) aryl, or $R^{7A2}$-substituted or unsubstituted 5 to 8 membered (e.g., 5 to 6 membered) heteroaryl. In embodiments, $R^{7A2}$ is independently $R^{7A3}$-substituted or unsubstituted $C_1$-$C_{10}$ (e.g., $C_1$-$C_6$) alkyl, $R^{7A3}$-substituted or unsubstituted 2 to 10 membered (e.g., 2 to 6 membered) heteroalkyl, $R^{7A3}$-substituted or unsubstituted $C_3$-$C_8$ (e.g., $C_5$-$C_7$) cycloalkyl, $R^{7A3}$-substituted or unsubstituted 3 to 8 membered (e.g., 3 to 6 membered) heterocycloalkyl, $R^{7A3}$-substituted or unsubstituted $C_5$-$C_{10}$ (e.g., $C_5$-$C_6$) aryl, or $R^{7A3}$-substituted or unsubstituted 5 to 8 membered (e.g., 5 to 6 membered) heteroaryl. In embodiments, $R^{7A3}$ is independently unsubstituted $C_1$-$C_{10}$ (e.g., $C_1$-$C_6$) alkyl, unsubstituted 2 to 10 membered (e.g., 2 to 6 membered) heteroalkyl, unsubstituted $C_3$-$C_8$ (e.g. $C_5$-$C_7$) cycloalkyl, unsubstituted 3 to 8 membered (e.g., 3 to 6 membered) heterocycbalkyl, unsubstituted $C_5$-$C_{10}$ (e.g., $C_5$-$C_6$) aryl, or unsubstituted 5 to 8 membered (e.g., 5 to 6 membered) heteroaryl.

In embodiments of any formula disclosed herein, one or more of $R^{1A}$, $R^{1B}$, $R^{2A}$, $R^{2B}$, $R^{3A}$, $R^{3B}$, $R^{4A}$, $R^{4B}$, $R^{5A}$, $R^{5B}$, $R^{7A}$, $R^{7B}$, $R^{8A}$, $R^{8B}$, $R^{9A}$, $R^{9B}$, $R^{10A}$ and $R^{10B}$ is independently a size-limited substituent or a lower substituent. In embodiments, $R^{1A}$, $R^{1B}$, $R^{2A}$, $R^{2B}$, $R^{3A}$, $R^{3B}$, $R^{4A}$, $R^{4B}$, $R^{5A}$, $R^{5B}$, $R^{7A}$, $R^{7B}$, $R^{8A}$, $R^{8B}$, $R^{9A}$, $R^{9B}$, $R^{10A}$ or $R^{10B}$ is independently $R^{11A1}$-substituted or unsubstituted $C_1$-$C_{10}$ (e.g., $C_1$-$C_6$) alkyl, $R^{11A1}$-substituted or unsubstituted 2 to 10 membered (e.g., 2 to 6 membered) heteroalkyl, $R^{11A1}$-substituted or unsubstituted $C_3$-$C_8$ (e.g., $C_5$-$C_7$) cycloalkyl, $R^{11A1}$-substituted or unsubstituted 3 to 8 membered (e.g., 3 to 6 membered) heterocycloalkyl, $R^{11A1}$-substituted or unsubstituted $C_5$-$C_{10}$ (e.g., $C_5$-$C_6$) aryl, or $R^{11A1}$-substituted or unsubstituted 5 to 8 membered (e.g., 5 to 6 membered) heteroaryl.

In embodiments, $R^{11A1}$ is independently a size-limited substituent or a lower substituent. In embodiments, $R^{11A1}$ is independently unsubstituted $C_1$-$C_{10}$ (e.g., $C_1$-$C_6$) alkyl, unsubstituted 2 to 10 membered (e.g., 2 to 6 membered) heteroalkyl, unsubstituted $C_3$-$C_5$ (e.g., $C_5$-$C_7$) cycloalkyl, unsubstituted 3 to 8 membered (e.g., 3 to 6 membered) heterocycloalkyl, unsubstituted $C_5$-$C_{10}$ (e.g., $C_5$-$C_6$) aryl, or unsubstituted 5 to 8 membered (e.g., 5 to 6 membered) heteroaryl.

In embodiments of the compounds of Formulae (I)-(IV), the compounds have the structure of one of Formulae (Ia)-(IVa) following.

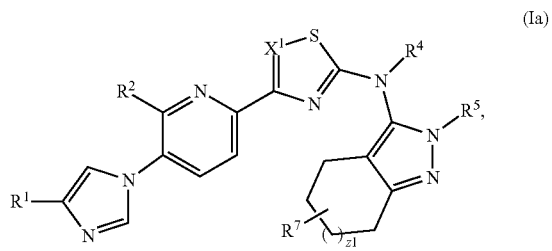

(Ia)

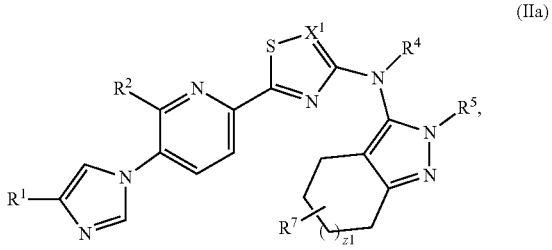

(IIa)

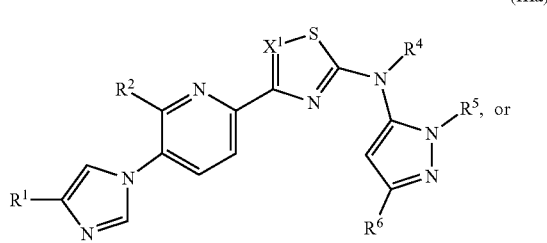

(IIIa)

(IVa)

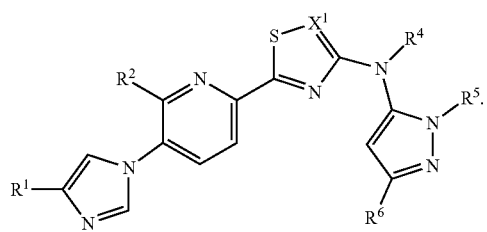

In embodiments of the compound of Formulae (I)-(II), z1 is 0, 1 or 2. In embodiments, z1 is 0. In embodiments, z1 is 1. In embodiments, z1 is 2.

In embodiments, z1 is 0, and the compounds of Formulae (I)-(II) have the structures following:

(Ib)

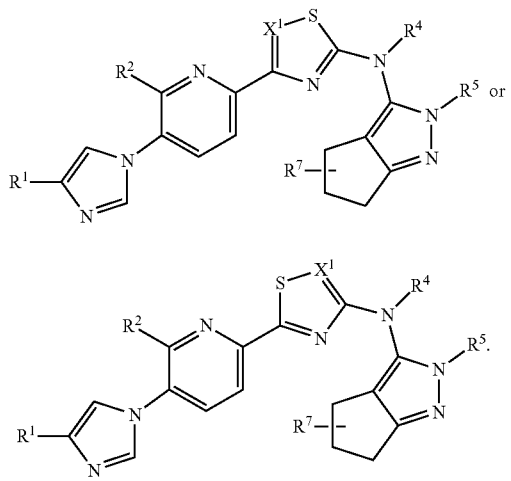

(IIb)

In embodiments, z1 is 1, and the compounds of Formulae (I)-(II) have the structures following:

(Ic)

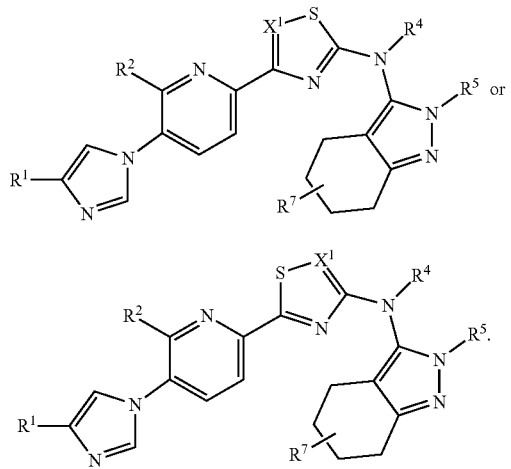

(IIc)

In embodiments, z1 is 2, and the compounds of Formulae (I)-(II) have the structures following:

(Id)

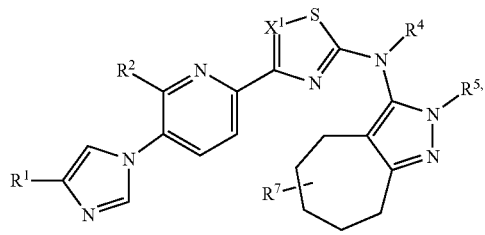

(IId)

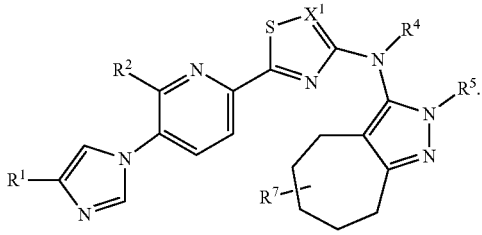

Further to the compounds with structure of any of Formulae (I)-(IV), and embodiments thereof, in embodiments $R^1$ is hydrogen, or substituted or unsubstituted alkyl. In embodiments, $R^1$ is unsubstituted alkyl. In embodiments, $R^1$ is substituted or unsubstituted $C_1$-$C_{10}$ (e.g., $C_1$-$C_6$) alkyl. In embodiments, $R^1$ is unsubstituted $C_1$-$C_6$ alkyl. In embodiments, $R^1$ is methyl, ethyl, n-propyl, isopropyl, butyl, tert-butyl, pentyl or hexyl. In embodiments, $R^1$ is methyl.

Further to the compounds with structure of any one of Formulae (I)-(IV), and embodiments thereof, in embodiments $R^2$ is hydrogen or —$OR^{2A}$. In embodiments, $R^2$ is hydrogen. In embodiments, $R^2$ is —$OR^{2A}$, and the compounds have a structure following:

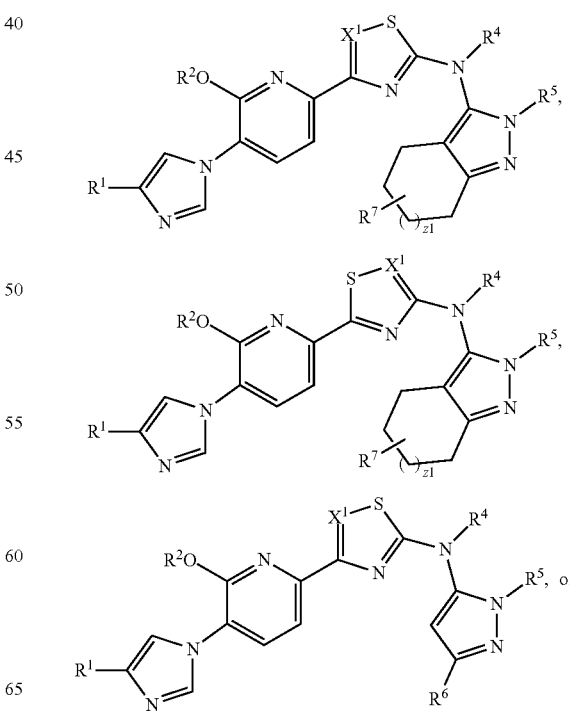

-continued

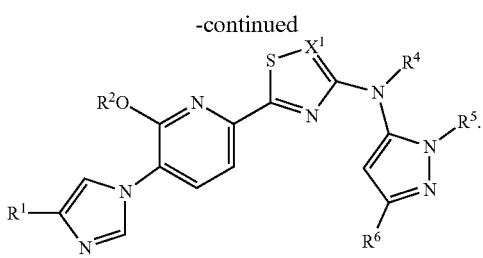

In embodiments wherein $R^2$ is —$OR^{2A}$, $R^{2A}$ is hydrogen, or substituted or unsubstituted alkyl. In embodiments, $R^{2A}$ is hydrogen. In embodiments, $R^{2A}$ is unsubstituted alkyl. In embodiments, $R^{2A}$ is unsubstituted $C_1$-$C_{10}$ (e.g., $C_1$-$C_6$) alkyl. In embodiments, e is methyl, ethyl, n-propyl, isopropyl, butyl, tert-butyl, pentyl or hexyl. In embodiments, $R^{2A}$ is methyl.

Further to the compounds with structure of any one of Formulae (I)-(IV), and embodiments thereof, in embodiments the compounds have a structure following:

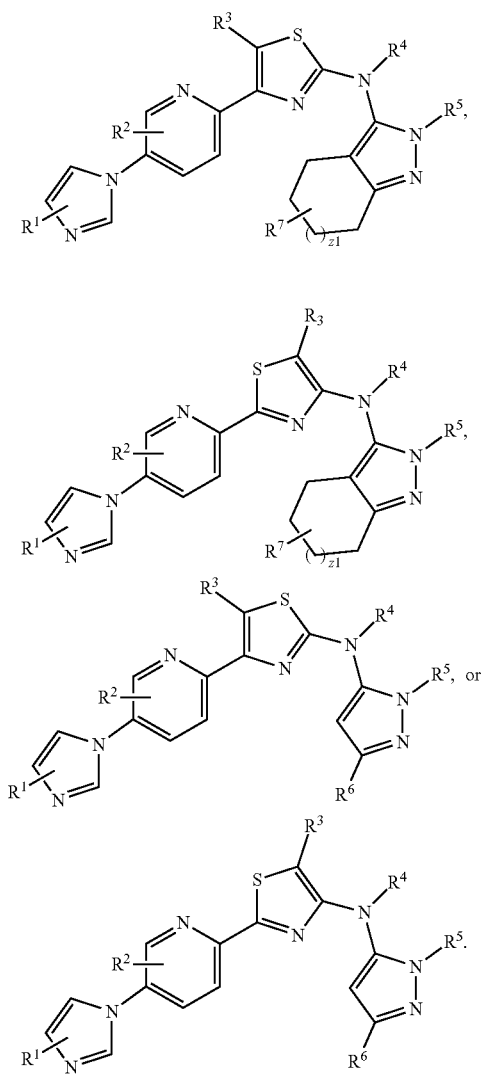

In embodiments, $R^3$ is hydrogen, halogen, —$CF_3$, —$CCl_3$, —$CBr_3$, —$Cl_3$, —CN, substituted or unsubstituted alkyl, substituted or unsubstituted heteroalkyl, substituted or unsubstituted cycloalkyl, or substituted or unsubstituted heterocycloalkyl. In embodiments, $R^3$ is hydrogen. In embodiments, $R^3$ is substituted or unsubstituted alkyl, substituted or unsubstituted heteroalkyl, substituted or unsubstituted cycloalkyl, or substituted or unsubstituted heterocycloalkyl.

In embodiments, $R^3$ is unsubstituted alkyl. In embodiments, $R^3$ is unsubstituted $C_1$-$C_{10}$ alkyl. In embodiments, $R^3$ is methyl, ethyl, n-propyl or isopropyl. In embodiments, $R^3$ is methyl.

In embodiments, $R^3$ is substituted alkyl. In embodiments, $R^3$ is substituted $C_1$-$C_{10}$ alkyl. In embodiments, $R^3$ is substituted $C_1$-$C_6$ alkyl. In embodiments, $R^3$ is substituted $C_1$-$C_3$ alkyl. In embodiments, $R^3$ is substituted methyl or substituted ethyl. In embodiments, $R^3$ is substituted methyl.

In embodiments, $R^3$ is $R^{3A1}$-substituted alkyl. In embodiments, $R^3$ is $R^{3A1}$-substituted $C_1$-$C_{10}$ alkyl, $R^{3A1}$-substituted $C_1$-$C_6$ alkyl or $R^{3A1}$-substituted $C_1$-$C_3$ alkyl. In embodiments, $R^3$ is $R^{3A1}$-substituted methyl or $R^{3A1}$-substituted ethyl. In embodiments, $R^3$ is $R^{3A1}$-substituted methyl.

In embodiments, $R^3$ is $R^{3A1}$-substituted alkyl, and $R^{3A1}$ is halogen. In embodiments, $R^3$ is $R^{3A1}$-substituted $C_1$-$C_{10}$ alkyl, and $R^{3A1}$ is halogen. In embodiments, $R^3$ is $R^{3A1}$-substituted $C_1$-$C_6$ alkyl, and $R^{3A1}$ is halogen. In embodiments, $R^3$ is $R^{3A1}$-substituted $C_1$-$C_3$ alkyl, and $R^{3A1}$ is halogen. In embodiments, $R^{3A1}$ is independently present at $R^3$ one or more times. In embodiments, $R^{3A1}$ is present at $R^3$ one time. In embodiments, $R^{3A1}$ is independently present at $R^3$ a plurality of times. In embodiments, $R^3$ is —$CH_2F$, —$CHF_2$, —$CH_2$—$CF_3$, —$CH_2$—$CHF_2$ or —$CH_2$—$CH_2F$. In embodiments, $R^{3A1}$ is —$CF^3$.

In embodiments, $R^3$ is $R^{3A1}$-substituted alkyl, and $R^{3A1}$ is —OH. In embodiments, $R^3$ is $R^{3A1}$-substituted $C_1$-$C_{10}$ alkyl, $R^{3A1}$-substituted $C_1$-$C_6$ alkyl or $R^{3A1}$-substituted $C_1$-$C_3$ alkyl, and $R^{3A1}$ is —OH. In embodiments, $R^{1A3}$ is independently present at $R^3$ one or more times. In embodiments, $R^{3A1}$ is present at $R^3$ one time. In embodiments, $R^3$ is —$CH_2OH$, —$(CH_2)_2OH$, —$(CH_2)_3OH$, or —$CH_2$—$C(CH_3)_2OH$.

In embodiments, $R^{3A1}$ is $R^{3A2}$-substituted or unsubstituted heterocycloalkyl. In embodiments, $R^{3A1}$ is unsubstituted heterocycloalkyl. In embodiments, $R^{3A1}$ is $R^{3A2}$-substituted heterocycloalkyl. In embodiments, $R^{3A1}$ is $R^{3A2}$-substituted or unsubstituted 3 to 8 membered heterocycloalkyl. In embodiments, $R^{3A1}$ is unsubstituted 3 to 8 membered heterocycloalkyl. In embodiments, $R^{3A1}$ is $R^{3A2}$-substituted unsubstituted 3 to 8 membered heterocycloalkyl. In embodiments, $R^{3A2}$ is halogen or unsubstituted $C_1$-$C_6$ alkyl. In embodiments, $R^{3A2}$ is halogen present one or more times. In embodiments, $R^{3A2}$ is unsubstituted $C_1$-$C_6$ alkyl. In embodiments, $R^{3A2}$ is unsubstituted methyl, ethyl, n-propyl or isopropyl.

In embodiments, $R^3$ is methyl substituted with 4-methylpiperazin-1-yl, or methyl substituted with 3,3-difluoropyrrolidin-1-yl.

In embodiments, $R^3$ is substituted or unsubstituted heteroalkyl. In embodiments, $R^3$ is unsubstituted heteroalkyl. In embodiments, $R^3$ is unsubstituted 2 to 10 membered heteroalkyl. In embodiments, $R^3$ is substituted heteroalkyl. In embodiments, $R^3$ is substituted 2 to 10 membered heteroalkyl.

In embodiments, $R^3$ is $R^{3A1}$-substituted heteroalkyl. In embodiments, $R^3$ is $R^{3A1}$-substituted 2 to 10 membered heteroalkyl. In embodiments, $R^3$ includes a nitrogen within the heteroalkyl chain. In embodiments, $R^3$ includes an oxygen within the heteroalkyl chain. In embodiments, $R^{3A1}$ is $R^{3A2}$-substituted or unsubstituted alkyl. In embodiments, $R^{3A1}$ is $R^{3A2}$-substituted $C_1$-$C_{13}$ alkyl. In embodiments, $R^{3A1}$ is unsubstituted $C_1$-$C_{10}$ alkyl. In embodiments, $R^{3A1}$ is unsubstituted $C_1$-$C_3$ alkyl. In embodiments, $R^{3A1}$ is unsubstituted methyl. In embodiments, $R^{3A1}$ is unsubstituted ethyl. In embodiments, $R^{3A1}$ is unsubstituted isopropyl. In embodiments, $R^{3A2}$ is unsubstituted alkyl. In embodiments, $R^{3A2}$ is unsubstituted $C_1$-$C_{10}$ alkyl. In embodiments, $R^{3A2}$ is unsubstituted $C_1$-$C_3$ alkyl.

In embodiments, $R^3$ is —$CH_2$—O—$CH_3$, —$(CH_2)_2$—O—$CH_3$, —$CH_2NHCH_3$, —$(CH_2)_2NHCH_3$, —$CH_2N(CH_3)_2$, or —$(CH_2)_2N(CH_3)_2$.

In embodiments, $R^3$ is substituted or unsubstituted cycloalkyl. In embodiments, $R^3$ is substituted cycloalkyl. In embodiments, $R^3$ is unsubstituted cycloalkyl. In embodiments, $R^3$ is substituted $C_3$-$C_8$ cycloalkyl. In embodiments, $R^3$ is unsubstituted $C_3$-$C_8$ cycloalkyl. In embodiments, $R^3$ is unsubstituted $C_3$-$C_6$ cycloalkyl. In embodiments, $R^3$ is unsubstituted cyclopropyl, unsubstituted cyclobutyl, unsubstituted cyclopentyl or unsubstituted cyclohexyl. In embodiments, $R^3$ is unsubstituted cyclopropyl. In embodiments, $R^3$ is unsubstituted cyclobutyl. In embodiments, $R^3$ is unsubstituted cyclopentyl. In embodiments, $R^3$ is unsubstituted cyclohexyl.

In embodiments, $R^3$ is $R^{3A1}$-substituted cycloalkyl. In embodiments, $R^3$ is $R^{3A1}$-substituted $C_3$-$C_6$ cycloalkyl. In embodiments, $R^{3A1}$ is independently halogen, —CN, —$CF_3$, —OH, —$NH_2$, —$SO_2$, —COOH, unsubstituted alkyl, unsubstituted heteroalkyl, unsubstituted cycloalkyl, unsubstituted heterocycloalkyl, unsubstituted aryl, or unsubstituted heteroaryl.

In embodiments, $R^3$ is substituted or unsubstituted heterocycloalkyl. In embodiments, $R^3$ is substituted heterocycloalkyl. In embodiments, $R^3$ is unsubstituted heterocycloalkyl. In embodiments, $R^3$ is substituted 3 to 6 membered heterocycloalkyl. In embodiments, $R^3$ is unsubstituted 3 to 6 membered heterocycloalkyl. In embodiments, $R^3$ includes a nitrogen within the substituted or unsubstituted heterocycloalkyl. In embodiments, $R^3$ includes an oxygen within the substituted or unsubstituted heterocycloalkyl.

In embodiments, $R^3$ is unsubstituted 3 to 6 membered heterocycloalkyl, and $R^3$ is oxiranyl, oxetanyl, tetrahydrofuranyl, or tetrahydro-2H-pyranyl.

In embodiments, $R^3$ is $R^{3A1}$-substituted heterocycloalkyl. In embodiments, $R^3$ is $R^{3A1}$-substituted 3 to 6 membered heterocycloalkyl. In embodiments, $R^{3A1}$ is independently halogen, —CN, —$CF_3$, —OH, —$NH_2$, —$SO_2$, —COOH, unsubstituted alkyl, unsubstituted heteroalkyl, unsubstituted cycloalkyl, unsubstituted heterocycloalkyl, unsubstituted aryl, or unsubstituted heteroaryl. In embodiments, $R^{3A1}$ is independently halogen. In embodiments, $R^{3A1}$ is independently unsubstituted alkyl. In embodiments, $R^{3A1}$ is independently unsubstituted $C_1$-$C_3$ alkyl.

Further to the compounds with structure of any one of Formulae (I)-(IV), and embodiments thereof, in embodiments $R^4$ is hydrogen, or substituted or unsubstituted alkyl. In embodiments, $R^4$ is hydrogen. In embodiments, $R^4$ is unsubstituted alkyl. In embodiments, $R^4$ is substituted alkyl. In embodiments, $R^4$ is unsubstituted $C_1$-$C_3$ alkyl. In embodiments, $R^4$ is substituted $C_1$-$C_3$ alkyl. In embodiments, $R^4$ is methyl, ethyl, n-propyl, or isopropyl.

Further to the compounds with structure of any one of Formulae (I)-(IV), and embodiments thereof, in embodiments $R^5$ is hydrogen, substituted or unsubstituted alkyl, substituted or unsubstituted heteroalkyl, substituted or unsubstituted cycloalkyl, or substituted or unsubstituted heterocycloalkyl.

In embodiments, $R^5$ is hydrogen.

In embodiments, $R^5$ is unsubstituted alkyl. In embodiments, $R^5$ is unsubstituted $C_1$-$C_{10}$ alkyl. In embodiments, $R^5$ is unsubstituted $C_1$-$C_6$ alkyl. In embodiments, $R^5$ is unsubstituted $C_1$-$C_3$ alkyl. In embodiments, $R^5$ is methyl, ethyl, n-propyl, or isopropyl.

In embodiments, $R^5$ is substituted alkyl. In embodiments, $R^5$ is substituted $C_1$-$C_{10}$ alkyl. In embodiments, $R^5$ is substituted $C_1$-$C_6$ alkyl. In embodiments, $R^5$ is substituted $C_1$-$C_3$ alkyl.

In embodiments, $R^5$ is $R^{5A1}$-substituted alkyl. In embodiments, $R^5$ is $R^{5A1}$-substituted $C_1$-$C_{10}$ alkyl. In embodiments, $R^5$ is $R^{5A1}$-substituted $C_1$-$C_6$ alkyl. In embodiments, $R^5$ is $R^{5A1}$-substituted $C_1$-$C_3$ alkyl.

In embodiments, $R^{5A1}$ is substituted or unsubstituted heterocycloalkyl. In embodiments, $R^{5A1}$ is substituted heterocycloalkyl. In embodiments, $R^{5A1}$ is unsubstituted heterocycloalkyl. In embodiments, $R^{5A1}$ is substituted 3 to 8 membered heterocycloalkyl. In embodiments, $R^{5A1}$ is unsubstituted 3 to 8 membered heterocycloalkyl. In embodiments, the unsubstituted 3 to 8 membered heterocycloalkyl is morpholinyl. In embodiments, $R^5$ is —$(CH_2)_2$-morpholinyl or —$CH_2CH(CH_3)$-morpholinyl.

In embodiments, $R^5$ is $R^{5A1}$-substituted alkyl, and $R^{5A1}$ is halogen. In embodiments, $R^5$ is $R^{5A1}$-substituted $C_1$-$C_{10}$ alkyl, and $R^{5A1}$ is halogen. In embodiments, $R^5$ is $R^{5A1}$-substituted $C_1$-$C_6$ alkyl, and $R^{5A1}$ is halogen. In embodiments, $R^5$ is $R^{5A1}$-substituted $C_1$-$C_3$ alkyl, and $R^{5A1}$ is halogen. In embodiments, $R^{5A1}$ is independently present at $R^5$ one or more times. In embodiments, $R^{5A1}$ is present at $R^5$ one time.

In embodiments, $R^{5A1}$ is independently present at $R^5$ a plurality of times. In embodiments, $R^{5A1}$ is fluorine. In embodiments, $R^5$ is —$CH_2F$, —$CHF_2$, —$CH_2$—$CF_3$, —$CH_2$—$CHF_2$ or —$CH_2$—$CH_2F$.

In embodiments, $R^{5A1}$ is —$CF^3$.

In embodiments, $R^5$ is $R^{5A1}$-substituted alkyl, and $R^{5A1}$ is —OH. In embodiments, $R^5$ is $R^{5A1}$-substituted $C_1$-$C_{10}$ alkyl, $R^{5A1}$-substituted $C_1$-$C_6$ alkyl or $R^{5A1}$-substituted $C_1$-$C_3$ alkyl, and $R^{5A1}$ is —OH. In embodiments, $R^{5A1}$ is independently present at $R^5$ one or more times. In embodiments, $R^{5A1}$ is present at $R^5$ one time. In embodiments, $R^5$ is —$CH_2OH$, —$(CH_2)_2OH$, —$(CH_2)_3OH$, or —$CH_2$—$C(CH_3)_2OH$.

In embodiments, $R^5$ is $R^{5A1}$-substituted alkyl, and $R^{5A1}$ is independently substituted or unsubstituted cycloalkyl. In embodiments, $R^{5A1}$ is independently substituted cycloalkyl. In embodiments, $R^{5A1}$ is independently unsubstituted cycloalkyl. In embodiments, $R^{5A1}$ is independently substituted or unsubstituted $C_3$-$C_8$ cycloalkyl. In embodiments, $R^{5A1}$ is independently substituted $C_3$-$C_8$ cycloalkyl. In embodiments, $R^{5A1}$ is independently unsubstituted $C_3$-$C_5$ cycloalkyl. In embodiments, $R^{5A1}$ is independently unsubstituted cyclopropyl. In embodiments, $R^{5A1}$ is independently substituted cyclopropyl. In embodiments, $R^5$ is —$(CH_2)$-cyclopropyl or —$(CH_2)_2$-cyclopropyl.

In embodiments, $R^5$ is substituted or unsubstituted heteroalkyl. In embodiments, $R^5$ is substituted heteroalkyl. In embodiments, $R^5$ is unsubstituted heteroalkyl. In embodiments, $R^5$ is substituted 2 to 8 membered heteroalkyl. In embodiments, $R^5$ is unsubstituted 2 to 8 membered heteroalkyl. In embodiments, $R^5$ is —$CH_2OCH_3$, or —$(CH_2)_2OCH_3$.

In embodiments, $R^5$ is substituted or unsubstituted cycloalkyl. In embodiments, $R^5$ is substituted cycloalkyl. In embodiments, is unsubstituted cycloalkyl. In embodiments, $R^5$ is substituted $C_3$-$C_5$ cycloalkyl. In embodiments, $R^5$ is unsubstituted $C_3$-$C_5$ cycloalkyl. In embodiments, $R^5$ is cyclopropyl, cyclobutyl, cyclopentyl, or cyclohexyl.

In embodiments, $R^5$ is substituted or unsubstituted heterocycloalkyl. In embodiments, $R^5$ is substituted heterocycloalkyl. In embodiments, $R^5$ is unsubstituted heterocycloalkyl. In embodiments, $R^5$ is substituted 3 to 8 membered heterocycloalkyl. In embodiments, $R^5$ is unsubstituted 3 to 8 membered heterocycloalkyl. In embodiments, $R^5$ is tetrahydro-2H-pyranyl.

Further to the compounds with structure of any one of Formulae (I)-(IV), and embodiments thereof, in embodiments $R^6$ is —$CF_3$.

Further to the compounds with structure of any one of Formulae (I)-(IV), and embodiments thereof, in embodiments $R^7$ is independently hydrogen, —$CF_3$, or substituted or unsubstituted alkyl. In embodiments $R^7$ is substituted alkyl. In embodiments $R^7$ is unsubstituted alkyl. In embodiments, $R^7$ is present once. In embodiments, $R^7$ is independently present a plurality of times. In embodiments, $R^7$ is independently present twice. In embodiments, $R^7$ is independently present thrice. In embodiments, $R^7$ is independently unsubstituted $C_1$-$C_{10}$ alkyl. In embodiments, $R^7$ is independently unsubstituted $C_1$-$C_6$ alkyl. In embodiments, $R^7$ is independently unsubstituted $C_1$-$C_5$ alkyl. In embodiments, $R^7$ is methyl, ethyl, n-propyl, isopropyl, isobutyl or pentyl.

Further to the compounds with structure of any one of Formulae (I)-(IV), and embodiments thereof, in embodiments $X^1$ is —$C(R^3)$, and $R^3$ and $R^7$ are hydrogen. In embodiments $X^1$ is $X^1$ is —$C(R^3)$, $R^3$ and $R^7$ are hydrogen, $R^1$ is unsubstituted alkyl, and $R^2$ is —$OR^{2A}$. In embodiments, $X^1$ is —$C(R^3)$, $R^3$ and $R^7$ are hydrogen, $R^1$ is unsubstituted $C_1$-$C_5$ alkyl, and $R^2$ is —$OR^{2A}$, wherein $R^{2A}$ is unsubstituted $C_1$-$C_5$ alkyl. In embodiments, the compounds have a structure following:

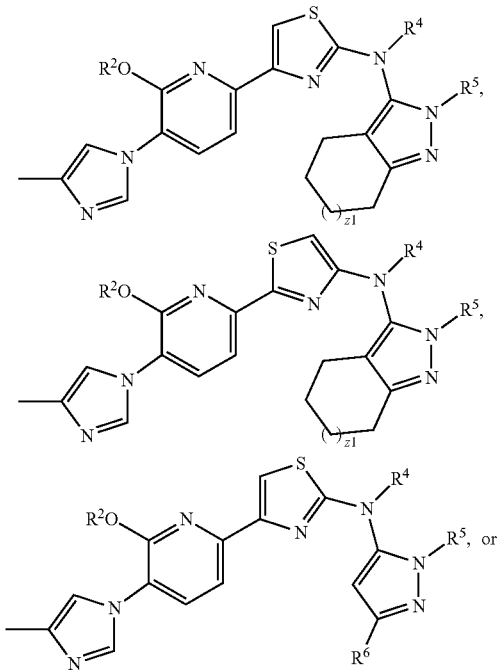

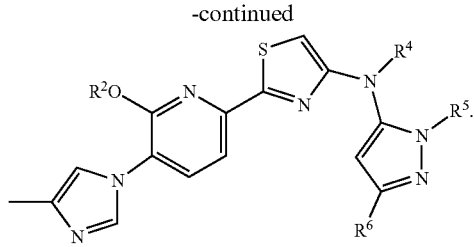

In embodiments, $X^1$ is $C(R^3)$, $R^3$ and $R^7$ are hydrogen, $R^1$ is methyl, and $R^2$ is —$OCH_3$.

Further to the compounds with structure of any one of Formulae (I)-(IV), and embodiments thereof, in embodiments $X^1$ is N. In embodiments, the compounds have a structure following:

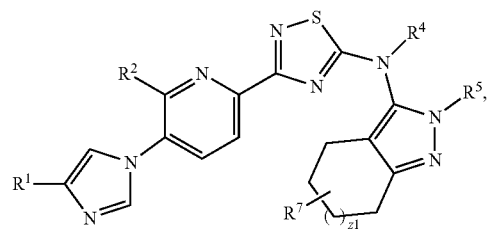

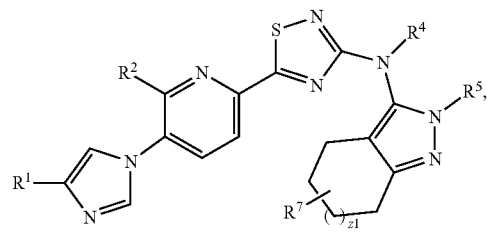

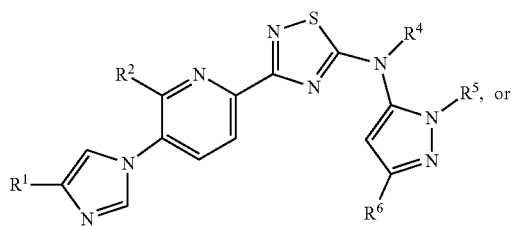

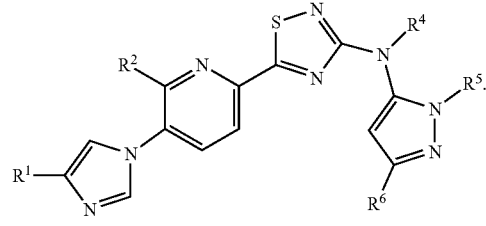

Further to the compounds with structure of any one of Formulae (III)-(IV), and embodiments thereof, in embodiments the compounds have a structure following:

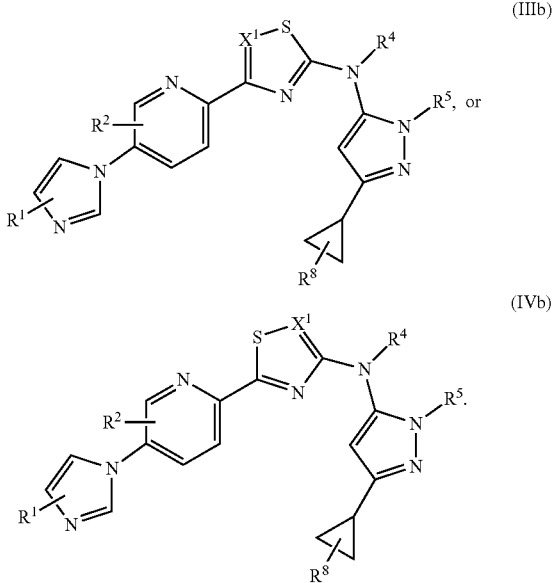

(IIIb)

(IVb)

Regarding Formulae (IIIb)-(IVb), $R^8$ is independently hydrogen, halogen, —$N_3$, —$CF_3$, —$CCl_3$, —$CBr_3$, —$CI_3$, —CN, —CHO, —$OR^{8A}$, —$NR^{8A}R^{8B}$, —$COOR^{8A}$, —C(O)$NR^{8A}R^{8B}$, —$NO_2$, —$SR^{8A}$, —$S(O)_{n8}R^{8A}$, —$S(O)_{n8}R^{8A}$, —$S(O)_{n8}NR^{8A}R^{8B}$, —$NHNR^{8A}R^{8B}$, —$ONR^{8A}R^{8B}$, —NHC(O)$NHNR^{8A}R^{8B}$, substituted or unsubstituted alkyl, substituted or unsubstituted heteroalkyl, substituted or unsubstituted cycloalkyl, substituted or unsubstituted heterocycloalkyl, substituted or unsubstituted aryl, or substituted or unsubstituted heteroaryl. $R^{8A}$ and $R^{8B}$ are independently hydrogen, substituted or unsubstituted alkyl, substituted or unsubstituted heteroalkyl, substituted or unsubstituted cycloalkyl, substituted or unsubstituted heterocycloalkyl, substituted or unsubstituted aryl, or substituted or unsubstituted heteroaryl. n8 is 1 or 2.

In embodiments, $R^8$ is independently hydrogen, halogen, —$N_3$, —$CF_3$, —$CCl_3$, —$CBr_3$, —CN, —CHO, —$OR^{8A}$, —$NR^{8A}R^{8B}$, —$COOR^{8A}$, —C(O)$NR^{8A}R^{8B}$, —$NO_2$, —$SR^{8A}$, —$S(O)_{n8}R^{8A}$, $S(O)_{n8}OR^{8A}$, —$S(O)_{n8}NR^{8A}R^{8B}$, —$NHNR^{8A}R^{8B}$, —$ONR^{8A}R^{8B}$, —NHC(O)$NHNR^{8A}R^{8B}$, $R^{8A1}$-substituted or unsubstituted alkyl, $R^{8A1}$-substituted or unsubstituted heteroalkyl, $R^{8A1}$-substituted or unsubstituted cycloalkyl, $R^{8A1}$-substituted or unsubstituted heterocycloalkyl, $R^{8A1}$-substituted or unsubstituted aryl, or $R^{8A1}$-substituted or unsubstituted heteroaryl. $R^{8A1}$ is independently halogen, —CN, —$CF_3$, —OH, —$NH_2$, —$SO_2$, —COOH, $R^{8A2}$-substituted or unsubstituted alkyl, $R^{8A2}$-substituted or =substituted heteroalkyl, $R^{8A2}$-substituted or unsubstituted cycloalkyl, $R^{8A2}$-substituted or an substituted heterocycloalkyl, $R^{8A2}$-substituted or unsubstituted aryl, or $R^{8A2}$-substituted or unsubstituted heteroaryl. $R^{8A2}$ is independently halogen, —CN, —$CF_3$, —OH, —$NH_2$, —$SO_2$, —COOH, $R^{8A3}$-substituted or unsubstituted alkyl, $R^{8A3}$-substituted or unsubstituted heteroalkyl, $R^{8A3}$-substituted or unsubstituted cycloalkyl, $R^{8A3}$-substituted or unsubstituted heterocycloalkyl, $R^{8A3}$-substituted or unsubstituted aryl, or $R^{8A3}$-substituted or unsubstituted heteroaryl. $R^{8A3}$ is independently halogen, —CN, —$CF_3$, —OH, —$NH_2$, —$SO_2$, —COOH, unsubstituted alkyl, unsubstituted heteroalkyl, unsubstituted cycloalkyl, unsubstituted heterocycloalkyl, unsubstituted aryl, or unsubstituted heteroaryl.

In embodiments, one or more of $R^{8A1}$, $R^{8A2}$, or $R^{8A3}$ is a size-limited substituent or a lower substituent. In embodiments, $R^{8A1}$ is independently $R^{8A2}$-substituted or unsubstituted $C_1$-$C_{10}$ (e.g., $C_1$-$C_5$) alkyl, $R^{8A2}$-substituted or unsubstituted 2 to 10 membered (e.g., 2 to 6 membered) heteroalkyl, $R^{8A2}$-substituted or unsubstituted $C_3$-$C_8$ (e.g., $C_5$-$C_7$) cycloalkyl, $R^{8A2}$-substituted or unsubstituted 3 to 8 membered (e.g., 3 to 6 membered) heterocycloalkyl, $R^{8A2}$-substituted or unsubstituted $C_5$-$C_{10}$ (e.g., $C_5$-$C_6$) aryl, or $R^{8A2}$-substituted or unsubstituted 5 to 8 membered (e.g., 5 to 6 membered) heteroaryl. In embodiments, $R^{8A2}$ is independently $R^{8A3}$-substituted or unsubstituted $C_1$-$C_{10}$ (e.g., $C_1$-$C_6$) alkyl, $R^{8A3}$-substituted or unsubstituted 2 to 10 membered (e.g., 2 to 6 membered) heteroalkyl, $R^{8A3}$-substituted or unsubstituted $C_3$-$C_8$ (e.g., $C_5$-$C_7$) cycloalkyl, $R^{8A3}$-substituted or unsubstituted 3 to 8 membered (e.g., 3 to 6 membered) heterocycloalkyl, $R^{8A3}$-substituted or unsubstituted $C_5$-$C_{10}$ (e.g., $C_5$-$C_6$) aryl, or $R^{8A3}$ substituted or unsubstituted 5 to 8 membered (e.g., 5 to 6 membered) heteroaryl. In embodiments, $R^{8A3}$ is independently unsubstituted $C_1$-$C_{10}$ (e.g., $C_1$-$C_6$) alkyl, unsubstituted 2 to 10 membered (e.g., 2 to 6 membered) heteroalkyl, unsubstituted $C_3$-$C_8$ (e.g., $C_5$-$C_7$) cycloalkyl, unsubstituted 3 to 8 membered (e.g., 3 to 6 membered) heterocycloalkyl, unsubstituted $C_5$-$C_{10}$ (e.g., $C_5$-$C_6$) aryl, or unsubstituted 5 to 8 membered (e.g., 5 to 6 membered) heteroaryl.

In embodiments, $R^8$ is independently unsubstituted alkyl, unsubstituted heteroalkyl, unsubstituted cycloalkyl, unsubstituted heterocycloalkyl, unsubstituted aryl, or unsubstituted heteroaryl.

In embodiments, $R^8$ is independently substituted alkyl, substituted heteroalkyl, substituted cycloalkyl, substituted heterocycloalkyl, substituted aryl, or substituted heteroaryl.

In embodiments, the compound of Formula (IIIb) has the structure following:

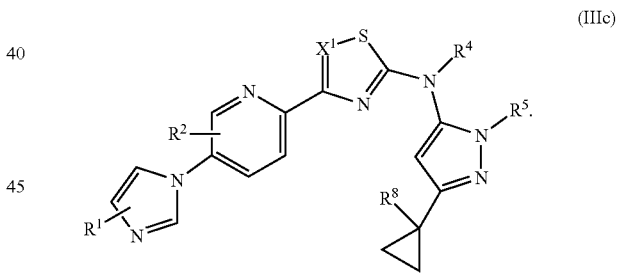

(IIIc)

In embodiments, the compound of Formula (IVb) has the structure following:

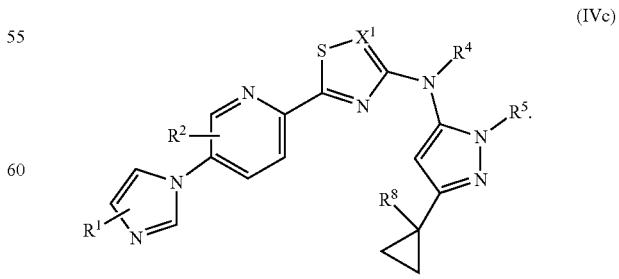

(IVc)

In embodiments, the compound of Formula (IIIc) has the structure following:

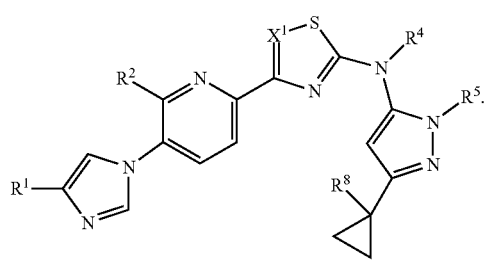
(IIId)

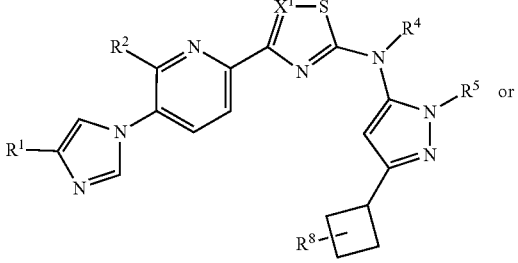
(IIIf)

In embodiments, the compound of Formula (IIIc) has the structure following:

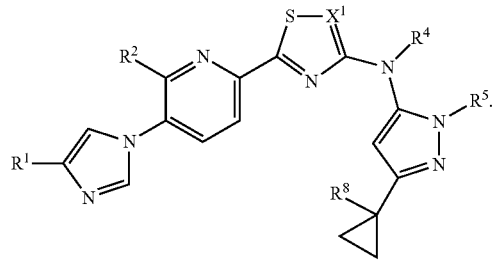
(IVd)

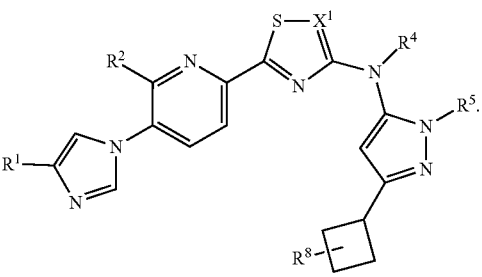
(IVf)

Further to the compounds with structure of any one of Formulae (III)-(IV), and embodiments thereof, in embodiments the compounds have a structure following:

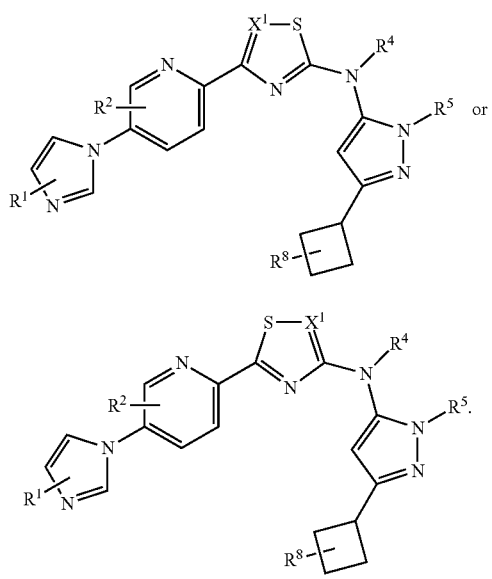
(IIIe)

(IVe)

Regarding Formulae (IIIe) and (IVe), $R^8$, $R^{8A}$, $R^{8B}$, n1, n2, n3, n4, n5, n7 and n8 are as disclosed for Formulae (IIIb)-(IVb).

In embodiments, the compounds of Formulae (IIIe)-(IVe) have the structure of Formulae (IIIf)-(IVf) following:

Further to the compounds with structure of any one of Formulae (IIIb), (IIIc), (IIId), (IIIe), (IIIf), (IVb), (IVc), (IVd), (IVe), or (IVf), and embodiments thereof, in embodiments $R^8$ is independently hydrogen, halogen, —$CF_3$, or substituted or unsubstituted alkyl. In embodiments, $R^8$ is independently hydrogen. In embodiments, $R^8$ is independently halogen. In embodiments, $R^8$ is independently fluoro. In embodiments, $R^8$ is independently —$CF_3$. In embodiments, $R^8$ is independently substituted or unsubstituted alkyl. In embodiments, $R^8$ is independently substituted alkyl. In embodiments, $R^8$ is independently unsubstituted alkyl. In embodiments, $R^8$ is independently substituted $C_1$-$C_6$ alkyl. In embodiments, $R^8$ is independently unsubstituted $C_1$-$C_6$ alkyl. In embodiments, $R^8$ is methyl, ethyl, n-propyl, isopropyl, isobutyl or pentyl. In embodiments, $R^8$ is methyl. In embodiments, $R^8$ is ethyl. In embodiments, $R^8$ is n-propyl. In embodiments, $R^8$ is isopropyl. In embodiments, $R^8$ is isobutyl. In embodiments, $R^8$ is pentyl.

Further to the compounds with structure of any one of Formulae (IIIb), (IIIc), (IIId), (IIIe), (IIIf), (IVb), (IVc), (IVd), (IVe), or (IVf), and embodiments thereof, in embodiments $X^1$ is $C(R^3)$, $R^3$ is hydrogen, $R^1$ is unsubstituted alkyl, $R^2$ is —$OR^{2A}$ and $R^8$ is unsubstituted alkyl. In embodiments, $X^1$ is $C(R^3)$, $R^3$ is hydrogen, $R^1$ is unsubstituted $C_1$-$C_5$ alkyl, $R^2$ is —$OR^{2A}$ and $R^8$ is unsubstituted $C_1$-$C_5$ alkyl, wherein $R^{2A}$ is unsubstituted $C_1$-$C_5$ alkyl. In embodiments, $X^1$ is $C(R^3)$, $R^3$ is hydrogen, R is methyl, $R^8$ is methyl and $R^2$ is —$OCH_3$.

Further to the compounds with structure of any one of Formulae (IIIb), (IIIc), (IIId), (IIIe), (IIIf), (IVb), (IVc), (IVd), (IVe), or (IVf), and embodiments thereof, in embodiments $X^1$ is N.

Further to the compounds with structure of any one of Formulae (I)-(IV), (IIIb), (IIIc), (IIId), (IIIe), (IIIf), (IVb), (IVc), (IVd), (IVe), or (IVf), and embodiments thereof, in embodiments $R^4$ and $R^5$ are combined to form ring Z having the formula:

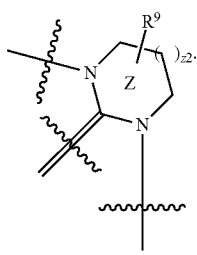

(Va)

Thus, in embodiments where R⁴ and R⁵ are combined to form ring Z, the compounds of Formulae (I)-(IV) and embodiments thereof have the respective structures:

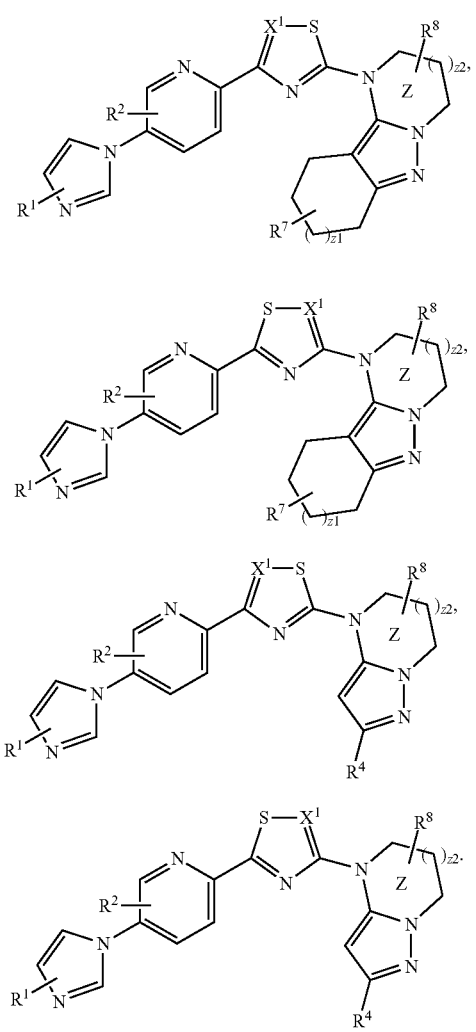

(IZ)

(IIZ)

(IIIZ) or (IVZ)

For Formula (Va) and embodiments thereof including Formulae (IZ)-(IVZ), z2 is 0, 1, or 2. $R^9$ is independently hydrogen, halogen, $-N_3$, $-CF_3$, $-CCl_3$, $-CBr_3$, $-CI_3$, $-CN$, $-CHO$, $-OR^{9A}$, $-NR^{9A}R^{9B}$, $-COOR^{9A}$, $-C(O)NR^{9A}R^{9B}$, $-NO_2$, $-SR^{9A}$, $-S(O)_{n9}R^{9A}$, $-S(O)_{n9}R^{9A}$, $-S(O)_{n9}NR^{9A}R^{9B}$, $-NHNR^{9A}R^{9B}$, $-ONR^{9A}R^{9B}$, $-NHC(O)NHNR^{9A}R^{9B}$, substituted or unsubstituted alkyl, substituted or unsubstituted heteroalkyl, substituted or unsubstituted cycloalkyl, substituted or unsubstituted heterocycloalkyl, substituted or unsubstituted aryl, or substituted or unsubstituted heteroaryl. $R^{9A}$ and $R^{9B}$ are independently hydrogen, substituted or unsubstituted alkyl, substituted or unsubstituted heteroalkyl, substituted or unsubstituted cycloalkyl, substituted or unsubstituted heterocycloalkyl, substituted or unsubstituted aryl, or substituted or unsubstituted heteroaryl. n9 is 1 or 2.

In embodiments, $R^9$ is independently hydrogen, halogen, $-N_3$, $-CF_3$, $-CCl_3$, $-CBr_3$, $-CI_3$, $-CN$, $-CHO$, $-OR^{9A}$, $-NR^{9A}R^{9B}$, $-COOR^{9A}$, $-C(O)NR^{9A}R^{9B}$, $-NO_2$, $-SR^{9A}$, $-S(O)_{n9}R^{9A}$, $-S(O)_{n9}R^{9A}$, $-S(O)_{n9}R^{9A}R^{9B}$, $-NHNR^{9A}R^{9B}$, $-ONR^{9A}R^{9B}$, $-NHC(O)NHNR^{9A}R^{9B}$, $R^{9A1}$-substituted or unsubstituted alkyl, $R^{9A1}$-substituted or unsubstituted heteroalkyl, $R^{9A1}$-substituted or unsubstituted cycloalkyl, $R^{9A1}$-substituted or unsubstituted heterocycloalkyl, $R^{9A1}$-substituted or unsubstituted aryl, or $R^{9A1}$-substituted or unsubstituted heteroaryl. $R^{9A1}$ is independently halogen, $-CN$, $-CF_3$, $-OH$, $-NH_2$, $-SO_2$, $-COOH$, $R^{9A2}$-substituted or unsubstituted alkyl, $R^{9A2}$-substituted or unsubstituted heteroalkyl, $R^{9A2}$-substituted or unsubstituted cycloalkyl, $R^{9A2}$-substituted or unsubstituted heterocycloalkyl, $R^{9A2}$-substituted or unsubstituted aryl, or $R^{9A2}$-substituted or unsubstituted heteroaryl. $R^{9A2}$ is independently halogen, $-CN$, $-CF_3$, $-OH$, $-NH_2$, $-SO_2$, $-COOH$, $R^{9A3}$-substituted or unsubstituted alkyl, $R^{9A3}$-substituted or unsubstituted heteroalkyl, $R^{9A3}$-substituted or unsubstituted cycloalkyl, $R^{9A3}$-substituted or unsubstituted heterocycloalkyl, $R^{9A3}$-substituted or unsubstituted aryl, or $R^{9A3}$-substituted or unsubstituted heteroaryl. $R^{9A3}$ is independently halogen, $-CN$, $-CF_3$, $-OH$, $-NH_2$, $-SO_2$, $-COOH$, unsubstituted alkyl, unsubstituted heteroalkyl, unsubstituted cycloalkyl, unsubstituted heterocycloalkyl, unsubstituted aryl, or unsubstituted heteroaryl.

In embodiments, one or more of $R^{9A1}$, $R^{9A2}$, or $R^{9A3}$ is independently a size-limited substituent or a lower substituent. In embodiments, $R^{9A1}$ is independently $R^{9A2}$-substituted or unsubstituted $C_1$-$C_{10}$ (e.g., $C_1$-$C_6$) alkyl, $R^{9A2}$-substituted or unsubstituted 2 to 10 membered (e.g., 2 to 6 membered) heteroalkyl, $R^{9A2}$-substituted or unsubstituted $C_3$-$C_8$ (e.g., $C_5$-$C_7$) cycloalkyl, $R^{9A2}$-substituted or unsubstituted 3 to 8 membered (e.g., 3 to 6 membered) heterocycloalkyl, $R^{9A2}$-substituted or unsubstituted $C_5$-$C_{10}$ (e.g., $C_5$-$C_6$) aryl, or $R^{9A2}$-substituted or unsubstituted 5 to 8 membered (e.g., 5 to 6 membered) heteroaryl. In embodiments, $R^{9A2}$ is independently $R^{9A2}$-substituted or unsubstituted $C_1$-$C_{10}$ (e.g., $C_1$-$C_6$) alkyl, $R^{9A3}$-substituted or unsubstituted 2 to 10 membered (e.g., 2 to 6 membered) heteroalkyl, $R^{9A3}$-substituted or unsubstituted $C_3$-$C_8$ (e.g., $C_5$-$C_7$) cycloalkyl, $R^{9A3}$-substituted or unsubstituted 3 to 8 membered (e.g., 3 to 6 membered) heterocycloalkyl, $R^{9A3}$-substituted or unsubstituted $C_5$-$C_{10}$ (e.g., $C_5$-$C_6$) aryl, or $R^{9A3}$-substituted or unsubstituted 5 to 8 membered (e.g., 5 to 6 membered) heteroaryl. In embodiments, $R^{9A3}$ is independently unsubstituted $C_1$-$C_{10}$ (e.g., $C_1$-$C_6$) alkyl, unsubstituted 2 to 10 membered (e.g., 2 to 6 membered) heteroalkyl, unsubstituted $C_3$-$C_8$ (e.g., $C_5$-$C_7$) cycloalkyl, unsubstituted 3 to 8 membered (e.g., 3 to 6 membered) heterocycloalkyl, unsubstituted $C_5$-$C_{10}$ (e.g., $C_5$-$C_6$) aryl, or unsubstituted 5 to 8 membered (e.g., 5 to 6 membered) heteroaryl.

In embodiments, $R^9$ is independently unsubstituted alkyl, unsubstituted heteroalkyl, unsubstituted cycloalkyl, unsubstituted heterocycloalkyl, unsubstituted aryl, or unsubstituted heteroaryl.

In embodiments, $R^9$ is independently substituted alkyl, substituted heteroalkyl, substituted cycloalkyl, substituted heterocycloalkyl, substituted aryl, or substituted heteroaryl.

Further to compounds having ring Z of Formula (Va), in embodiments the compound includes a plurality of independent: $R^9$ substituents. In embodiments, the compound includes one $R^9$ substituent. In embodiments, the compound includes two independent $R^9$ substituents. In embodiments, the compound includes three independent $R^9$ substituents.

Further to compounds of Formulae (I)-(IV) having ring Z of Formula (Va), in embodiments z2 is 0, 1 or 2. In embodiments, z2 is 0. In embodiments, z2 is 1. In embodiments, z2 is 2.

Further to compounds of Formulae (I)-(IV) having ring Z of Formula (Va), in embodiments $R^9$ is hydrogen, halogen, —$OR^{9A}$, —$NR^{9A}R^{9B}$, substituted or unsubstituted alkyl, substituted or unsubstituted cycloalkyl, or substituted or unsubstituted heterocycloalkyl. In embodiments, $R^9$ is hydrogen. In embodiments, $R^9$ is halogen. In embodiments, $R^9$ is fluoro. In embodiments, $R^9$ is —$OR^{9A}$. In embodiments, $R^9$ is —OH. In embodiments, $R^9$ is —$NR^{9A}R^{9B}$. In embodiments, $R^9$ is —$N(CH_3)_2$.

In embodiments, $R^9$ is substituted or unsubstituted alkyl. In embodiments, $R^9$ is unsubstituted $C_1$-$C_6$ alkyl. In embodiments, $R^9$ is methyl, ethyl, n-propyl, isopropyl, isobutyl or pentyl.

In embodiments, $R^9$ is substituted alkyl. In embodiments, $R^9$ is substituted $C_1$-$C_6$ alkyl. In embodiments, $R^9$ is $C_1$-$C_6$ alkyl substituted with —OH. In embodiments, $R^9$ is —$CH_2OH$ or —$C(CH_3)_2OH$.

Further to compounds of Formulae (I)-(IV) having ring Z of Formula (Va), in embodiments $R^9$ is substituted or unsubstituted cycloalkyl. In embodiments, $R^9$ is unsubstituted cycloalkyl. In embodiments, $R^5$ is substituted cycloalkyl. In embodiments, $R^9$ is unsubstituted $C_3$-$C_8$ cycloalkyl. In embodiments, $R^9$ is substituted $C_3$-$C_8$ cycloalkyl.

Further to compounds of Formulae (I)-(IV) having ring Z of Formula (Va), in embodiments $R^9$ is substituted or unsubstituted heterocycloalkyl. In embodiments, $R^9$ is unsubstituted heterocycloalkyl. In embodiments, $R^9$ is substituted heterocycloalkyl. In embodiments, $R^9$ is unsubstituted 3 to 8 membered heterocycloalkyl. In embodiments, $R^9$ is substituted 3 to 8 membered heterocycloalkyl.

In embodiments, $R^9$ is pyrrolidinyl-2,5-dione. In embodiments, $R^9$ is pyrrolidin-1-yl.

Further to compounds of Formulae (I)-(IV) having ring Z of Formula (Va), in embodiments $R^9$ is $X^1$ is $C(R^3)$, $R^3$ is hydrogen, $R^1$ is unsubstituted alkyl and $R^2$ is —$OR^{2A}$. In embodiments, $X^1$ is $C(R^3)$, $R^3$ is hydrogen, R is unsubstituted $C_1$-$C_5$ alkyl and $R^2$ is —$OR^{2A}$, wherein $R^{2A}$ is unsubstituted $C_1$-$C_5$ alkyl. In embodiments, $X^1$ is $C(R^3)$, $R^3$ is hydrogen, $R^1$ is methyl and $R^2$ is —$OCH_3$.

Further to the compounds with structure of any one of Formulae (I)-(IV), (IIIb), (IIIc), (IIId), (IIIe), (IVb), (IVc), (IVd), (IVe), or (IVf), and embodiments thereof, in embodiments $R^4$ and $R^5$ are combined to form ring Y having the formula:

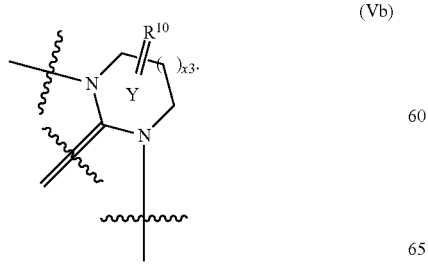

(Vb)

Thus, in embodiments where $R^4$ and $R^5$ are combined to form ring Y, the compounds of Formulae (I)-(IV) and embodiments thereof have the respective structures:

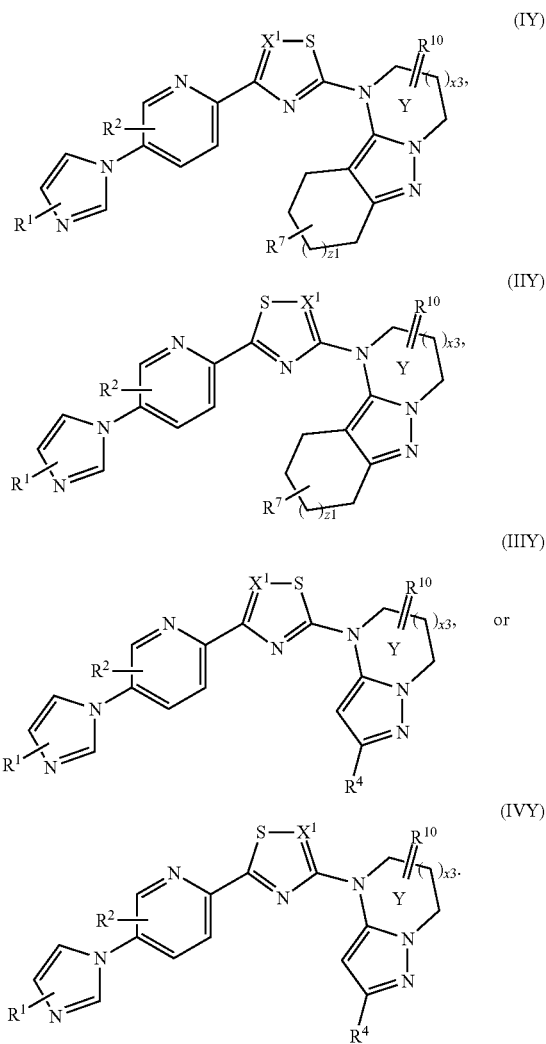

For Formula (Vb) and embodiments thereof including Formulae (IY)-(IVY), z3 is 0, 1, or 2. $R^{10}$ is =O, =S, =$CR^{10A}R^{10B}$, or =$NR^{10C}$. $R^{10A}$ an $R^{10B}$ are independently hydrogen, halogen, —$N_3$, —$CF_3$, —$CCl_3$, —$CBr_3$, —$CI_3$, —CN, —CHO, —$OR^{3A}$, —$NR^{3A}R^{3B}$, —$COOR^{3A}$, —$C(O)NR^{3A}R^{3B}$, —$NO_2$, —$SR^{3A}$, —$S(O)_{n3}R^{3A}$, —$S(O)_{n3}OR^{3A}$, —$S(O)_{n3}NR^{3A}R^{3B}$, —$NHNR^{3A}R^{3B}$, —$ONR^{3A}R^{3B}$, —NHC(O)NHNR^{3A}R^{3B}$, substituted or unsubstituted alkyl, substituted or unsubstituted heteroalkyl, substituted or unsubstituted cycloalkyl, substituted or unsubstituted heterocycloalkyl, substituted or unsubstituted aryl, or substituted or unsubstituted heteroaryl. $R^{10C}$ is hydrogen or —$OR^{10A}$.

In embodiments of compounds of Formulae (I)-(IV) having ring Y of Formula (Vb), z3 is 0. In embodiments, z3 is 1. In embodiments, z3 is 2.

In embodiments of compounds of Formulae (I)-(IV) having ring Y of Formula (Vb), $R^{10}$ is =$CR^{10A}R^{10B}$. In embodiments, $R^{10A}$ and $R^{10B}$ are hydrogen.

In embodiments of compounds of Formulae (I)-(IV) having ring Y of Formula (Vb), $R^{10}$ is =$NR^{10C}$. In embodiments, $R^{10C}$ is hydrogen. In embodiments, $R_{10A}$ is unsubstituted alkyl. In embodiments, $R_{10A}$ is unsubstituted $C_1$-$C_6$ alkyl. In embodiments, R=N—OH. In embodiments, $R^{10}$ is =NOCH$_3$.

III. Pharmaceutical Compositions

In another aspect, there is provided a pharmaceutical composition including a compound with structure of any one of Formulae (I)-(IV), (IIIb), (IIIc), (IIId), (IIIf), (IVb), (IVc), (IVd), (IVe), or (IVf), and embodiments thereof, in combination with a pharmaceutically acceptable excipient (e.g., carrier).

Pharmaceutical compositions provided herein include compositions wherein the active ingredient (e.g. compounds described herein, including embodiments or examples) is contained in a therapeutically effective amount, i.e., in an amount effective to achieve its intended purpose. The actual amount effective for a particular application will depend, inter alia, on the condition being treated. Determination of a therapeutically effective amount of a compound of the invention is well within the capabilities of those skilled in the art, especially in light of the detailed disclosure herein.

The dosage and frequency (single or multiple doses) administered to a mammal can vary depending upon a variety of factors, for example, whether the mammal suffers from another disease, and its route of administration; size, age, sex, health, body weight, body mass index, and diet of the recipient; nature and extent of symptoms of the disease being treated, kind of concurrent treatment, complications from the disease being treated or other health-related problems. Other therapeutic regimens or agents can be used in conjunction with the methods and compounds of Applicants' invention. Adjustment and manipulation of established dosages (e.g., frequency and duration) are well within the ability of those skilled in the art.

In embodiments, the pharmaceutical composition is formulated for administration once daily. In embodiments, the pharmaceutical composition is formulated for administration twice daily. In embodiments, the pharmaceutical composition is formulated for administration once weekly. In embodiments, the pharmaceutical composition is formulated for administration 1, 2, 3, 4, 5, 6, or 7 times weekly.

A. Formulations

The compounds disclosed herein can be prepared and administered in a wide variety of oral, parenteral, and topical dosage formulations. Thus, the compounds of the present invention can be administered by injection (e.g. intravenously, intramuscularly, intracutaneously, subcutaneously, intraduodenally, or intraperitoneally). Also, the compounds described herein can be administered by inhalation, for example, intranasally. Additionally, the compounds of the present invention can be administered transdermally or by ocular instillation. Multiple routes of administration (e.g., intramuscular, oral, transdermal, ocular instillation) are contemplated that can be used to administer the compounds disclosed herein. Accordingly, the present invention also provides pharmaceutical compositions which includes a pharmaceutically acceptable carrier or excipient and one or more compounds.

In one embodiment, the pharmaceutical composition includes a compound disclosed herein at a concentration in the range of about 0.01% to 1.00% (w/v). In one embodiment, the concentration of the compound is about 0.01%, 0.02%, 0.03%, 0.04%, 0.05%, 0.06%, 0.07%, 0.08%, 0.09%, 0.10%, 0.11%, 0.12%, 0.13%, 0.14%, 0.15%, 0.16%, 0.17%, 0.18%, 0.19%, 0.20%, 0.30%, 0.40%, 0.50%, 0.60%, 0.70%, 0.80%, 0.90%, or 1.00% (w/v), or even greater.

In one embodiment, the pharmaceutical composition includes one or more viscosity-enhancing agents, or thickening agents. Thickening agents are used for a variety of reasons, ranging from improving the form of the formulation for convenient administration to improving contact with an organ to improve bioavailability. The viscosity-enhancing agent may comprise a polymer containing hydrophilic groups such as monosaccharides, polysaccharides, ethylene oxide groups, hydroxyl groups, carboxylic acids or other charged functional groups. While not intending to limit the scope of the invention, some examples of useful viscosity-enhancing agents are sodium carboxymethylcellulose, hydroxypropyl methylcellulose, povidone, polyvinyl alcohol, and polyethylene glycol. In one embodiment, viscosity-enhancing agents are employed at a level between about 0.01% and about 2% (w/v).

In one embodiment, the pharmaceutical composition includes one or more tonicity agents useful to adjust the pharmaceutical composition to the desired isotonic range. Tonicity agents are well known in the art and some examples include glycerin, mannitol, sorbitol, sodium chloride, and other electrolytes. In one embodiment, the concentration of tonicity agent is in the range of about 0.1 to 2.00% (w/v). In one embodiment, the concentration of tonicity agent is in the range of about 1.15 to 1.30% (w/v). In one embodiment, the concentration of tonicity agent is about 0.10%, 0.20%, 0.30%, 0.40%, 0.50%, 0.60%, 0.70%, 0.80%, 0.90%, 1.00%, 1.10%, 1.20%, 1.30%, 1.40%, 1.50%, 1.60%, 1.70%, 1.80%, 1.90%, or 2.00%. In one embodiment, the concentration of tonicity agent is about 1.15%, 1.16%, 1.17%, 1.18%, 1.19%, 1.20%, 1.21%, 1.22%, 1.23%, 1.24%, 1.25%, 1.26%, 1.27%, 1.28%, 1.29%, or 1.30% (w/v).

In one embodiment, the pharmaceutical composition includes a solubilizer (e.g., surfactant or other appropriate co-solvent) in order to facilitate solubilization of one or more components of the pharmaceutical composition. Such solubilizers include Polysorbate 20, 60, and 80, Pluronic F-68, F-84, and P-103, cyclodextrin, hydroxy-beta-cyclodextrin, solutol, polyoxyethylene 40 stearate, and polyoxyl 35 castor oil. Such solubilizers can be employed at a level between about 0.01% and about 2% by weight. In one embodiment, the solubilizer is present in the range of about 0.01% to 0.20% (w/v). In one embodiment, the solubilizer is present at 0.01%, 0.02%, 0.03%, 0.04%, 0.05%, 0.06%, 0.07%, 0.08%, 0.09%, 0.10%, 0.11%, 0.12%, 0.13%, 0.14%, 0.15%, 0.16%, 0.17%, 0.18%, 0.19%, or 0.20% (w/v). In one embodiment, the solubilizer is polysorbate 80.

In embodiments, the pharmaceutical composition includes a preservative. In one embodiment, the preservative is benzalkonium chloride, chlorine dioxide, chlorobutanol, thimerosal, phenylmercuric acetate, or phenylmercuric nitrate. In one embodiment, the preservative is present at a concentration in the range of about 0.01% to 0.05% (w/v). In one embodiment, the preservative is present at a concentration in the range of about 0.015% to 0.025% (w/v). In one embodiment, the concentration of the preservative is about 0.015%, 0.016%, 0.017%, 0.018%, 0.019%, 0.020%, 0.021%, 0.022%, 0.023%, 0.024%, or 0.025% (w/v). In one embodiment, the preservative is benzalkonium chloride.

The compositions of the present invention may additionally include components to provide sustained release and/or comfort. Such components include high molecular weight, anionic mucomimetic polymers, gelling polysaccharides, and finely-divided drug carrier substrates. These components are discussed in greater detail in U.S. Pat. Nos. 4,911,920; 5,403,841; 5,212,162; and 4,861,760, the entire contents of each of which are incorporated herein by reference in their entirety and for all purposes.

B. Effective Dosages

Pharmaceutical compositions contemplated herein include compositions wherein the active ingredient is contained in an effective amount, i.e., in an amount effective to achieve its intended purpose. A "reduction" of a symptom or symptoms (and grammatical equivalents of this phrase) means decreasing of the severity or frequency of the symptom(s), or elimination of the symptom(s). The actual amount effective for a particular application will depend, inter alia, on the condition being treated. For example, when administered in methods to treat accumulation of $A\beta_{42}$ or $A\beta_{40}$, such compositions will contain amounts of active ingredients effective to achieve the desired result (e.g. decreasing the extent of $A\beta_{42}$ or $A\beta_{40}$ in a subject).

The dosage and frequency (single or multiple doses) of compounds administered can vary depending upon a variety of factors, including route of administration; size, age, sex, health, body weight, body mass index, and that of the recipient; nature and extent of symptoms of the disease being treated; presence of other diseases or other health-related problems; kind of concurrent treatment; and complications from any disease or treatment regimen. Other therapeutic regimens or agents can be used in conjunction with the methods and compounds of the invention.

For any compound described herein or combination thereof, the therapeutically effective amounts can be initially determined from cell culture assays. Target concentrations will be those concentrations of active compound(s) that are capable of decreasing accumulation of $A\beta_{42}$ or $A\beta_{40}$ as measured, for example, using methods known in the art.

Therapeutically effective amounts for use in humans may be determined from animal models. For example, a dose for humans can be formulated to achieve a concentration that has been found to be effective in animals.

Dosages may be varied depending upon the requirements of the subject and the compound being employed. The dose administered to a subject, in the context of the present invention, should be sufficient to effect a beneficial therapeutic response in the subject over time. The size of the dose also will be determined by the existence, nature, and extent of any adverse side effects. Generally, treatment is initiated with smaller dosages, which are less than the optimum dose of the compound. Thereafter, the dosage is increased by small increments until the optimum effect under circumstances is reached.

Dosage amounts and intervals can be adjusted individually to provide levels of the administered compounds effective for the particular clinical indication being treated. This will provide a therapeutic regimen that is commensurate with the severity of the individual's disease state.

Utilizing the teachings provided herein, an effective therapeutic treatment regimen can be planned that does not cause substantial toxicity and yet is entirely effective to treat the clinical symptoms demonstrated by the particular patient. This planning should involve the careful choice of active compound by considering factors such as compound potency, relative bioavailability, patient body weight, presence and severity of adverse side effects, preferred mode of administration, and the toxicity profile of the selected agent.

C. Toxicity

The ratio between toxicity and therapeutic effect for a particular compound is its therapeutic index and can be expressed as the ratio between $LD_{50}$ (the amount of compound lethal in 50% of the population) and $ED_{50}$ (the amount of compound effective in 50% of the population). Compounds that exhibit high therapeutic indices are preferred. Therapeutic index data obtained from cell culture assays and/or animal studies can be used in formulating a range of dosages for use in humans. The dosage of such compounds preferably lies within a range of plasma concentrations that include the $ED_{50}$ with little or no toxicity. The dosage may vary within this range depending upon the dosage form employed and the route of administration utilized. See, e.g. Fingl et al., In: THE PHARMACOLOGICAL BASIS OF THERAPEUTICS, Ch. 1, p. 1, 1975. The exact formulation, route of administration, and dosage can be chosen by the individual physician in view of the patient's condition and the particular method in which the compound is used.

IV. Methods of Use

In another aspect, there is provided use of a compound with structure of any one of Formulae (I)-(IV), (IIIb), (IIIc), (IIId), (IIIe), (IIIf), (IVb), (IVc), (IVd), (We), or (IVf), and embodiments thereof, for inhibiting production of $A\beta_{42}$ or $A\beta_{40}$ by a protease which proteolyzes an amyloid precursor protein (APP) or fragment thereof. In embodiments, the use is a method of inhibiting production of $A\beta_{42}$ or $A\beta_{40}$, the method including contacting a protease which proteolyzes an amyloid precursor protein (APP) or fragment thereof with an effective amount of a compound disclosed herein so as to inhibit production of $A\beta_{42}$ or $A\beta_{40}$. Methods for assaying $A\beta$ peptides are well known in the art.

In embodiments, the compound has no measurable effect on gamma-secretase-mediated processing of Notch-1 receptor or no adverse effect associated with any altered Notch-1 receptor signaling. Method for determining the effect on gamma-secretase-mediated processing of Notch-1 receptor, and on altered of Notch-1 receptor signaling are well known in the art.

In another aspect, there is provided use of a compound with structure of any one of Formulae (I)-(IV), (IIIb), (IIIc), (IIId), (IIIe), (IIIf), (IVb), (IVc), (IVd), (IVe), or (IVf), and embodiments thereof, for treating a disease or neurological disorder associated with elevated levels of specific fibrillogenic $A\beta$ peptides by inhibiting production of $A\beta_{42}$ or $A\beta_{40}$. In embodiments, the use is a method of treating a disease or neurological disorder associated with elevated levels of specific fibrillogenic $A\beta$ peptides by inhibiting production of $A\beta_{42}$ or $A\beta_{40}$, the method including administering to a subject in need thereof an effective amount of a compound with structure of any one of Formulae (I)-(IV), (IIIb), (IIIc), (IIId), (IIIe), (IIIf), (IVb), (IVc), (IVd), (IVe), or (IVf), and embodiments thereof.

In embodiments, the disease or neurological disorder is Alzheimer's disease (AD), Down Syndrome (DS), hemorrhagic stroke associated with cerebrovascular amyloidosis (HCHWA), cerebral amyloid angiopathy (CAA), idiophathic dilated cardiomyopathy, hereditary cerebral hemorrhage with amyloidosis, Dutch type (HCHWA-D), prion disorders, Creutzfeldt-Jakob disease (CJD), frontotemporal dementias (FTD), amyotropic lateral sclerosis (ALS), Huntington's disease (HD), Parkinson's disease (PD) and other neurodegenerative proteinopathies. In embodiments, the disease or neurological disorder is Alzheimer's disease (AD), Down Syndrome IDS), hemorrhagic stroke associated with cerebrovascular amyloidosis (HCHWA), cerebral amyloid angiopathy (CAA), idiophathic dilated cardiomyopathy, hereditary cerebral hemorrhage with amyloidosis, Dutch type (HCHWA-D), prion disorders, Creutzfeldt-Jakob disease (CJD), frontotemporal dementias (FTD), amyotropic lateral sclerosis (ALS), Huntington's disease (HD), Parkinson's disease (PD).

In embodiments, the disease or neurological disorder is Alzheimer's disease (AD).

Preferably, compounds of the present invention can be used in the treatment of neurological disorders, including but not limited to neurodegenerative conditions and other dementias or traumatic conditions. Exemplary neurological disorders may include diffuse Lewy body disease, Pick's disease, multisystem degeneration (Shy-Drager syndrome), motor neuron diseases including amyotrophic lateral sclerosis, degenerative ataxias, cortical basal degeneration, ALS-Parkinson's-Dementia complex of Guam, subacute sclerosing panencephalitis, Huntington's disease, synucleinopathies, primary progressive aphasia, striatonigral degeneration, Machado-Joseph disease/spinocerebellar ataxia type 3 and olivopontocerebellar degenerations, Gilles De La Tourette's disease, bulbar and pseudobulbar palsy, spinal and spinobulbar muscular atrophy (Kennedy's disease), primary lateral sclerosis, familial spastic paraplegia, Werdnig-Hoffmann disease, Kugelberg-Welander disease, Tay-Sach's disease, Sandhoff disease, familial spastic disease, Wohifart-Kugelberg-Welander disease, spastic paraparesis, progressive multSocal leukoencephalopathy, prion diseases (including Creutzfeldt-Jakob, Gerstmann-Straussler-Scheinker disease, Kuru and fatal familial insomnia), age-related dementia and other conditions with memory loss, such as vascular dementia, diffuse white matter disease (Binswanger's disease), dementia of endocrine or metabolic origin, dementia of head trauma and diffuse brain damage, dementia pugilistica and frontal lobe dementia, cerebral ischemia or infarction including embolic occlusion and thrombotic occlusion as well as intracranial hemorrhage of any type (including, but not limited to, epidural, subdural, subarachnoid and intracerebral), and intracranial and intravertebral lesions (including, but not limited to, contusion, penetration, shear, compression and laceration).

In embodiments, the compounds may be administered in combination, or sequentially, with another therapeutic agent. Such other therapeutic agents include those known for treatment, prevention, or amelioration of one or more symptoms of amyloidosis and neurodegenerative diseases and disorders. Such therapeutic agents include, but are not limited to, donepezil hydrochloride (ARICEPTS), rivastigmine tartrate (EXELON®), tacrine hydrochloride (COGNEX®) and galantamine hydrobromide (Reminyl).

V. Examples

The following examples are offered to illustrate, but not to limit the claimed invention.

General Chemistry Methods:

All reagents were of commercial quality and used without further purification unless indicated otherwise. Routine electrospray ionization mass spectra (ESI-MS) were recorded.

Screening Assays.

A variety of cell lines normally produce and secrete various Aβ peptide alloforms into the media upon culture in supportive media. Examples of cell lines routinely used to assess the ability of a compound to inhibit formation specific Aβ peptide alloforms such as $A\beta_{42}$, upon treatment of the cells with various concentrations of the compound for approximately 16 h followed by determining the concentration of the various Aβ peptide alloforms in the media both with and without treatment with the compound [(e.g., HEK-293, N2a delta E9/Swe, SHSY5Y and primary cerebral cortical neuronal cultures from embryonic day 18 (E18) embryos from timed pregnant WT Sprague-Dawley rats) (Netzer, W I et al., Gleevec inhibits β-amyloid production but not Notch cleavage. See e.g., *Proc. Natl. Acad. Sci. U.S.A.* 2003; 100:12444-12449.

The SH-SY5Y-APP human cell line was derived by transfecting a human neuroblastoma (SH-SY5Y) cell line with a plasmid expressing wild type human $APP_{751}$ cDNA and selecting for stable expression of human APP and human Aβ. In each case, the levels of $A\beta_{42}$ or $A\beta_{total}$ or $A\beta_{38}$ peptides secreted into the media of these cells were measured using either two-site monoclonal antibody (mAb)-based sandwich ELISA assays (described herein for $A\beta_{42}$ and $A\beta_{total}$) or in the case of $A\beta_{38}$ EC50's, using either the Meso Scale $A\beta_{38, 40, 42}$ triplex kit along with the Meso Scale Sector Imager 6000 according to the manufacturer's protocols. This SH-SY5Y-APP human cell line was used for all cell-based Aβ peptide immunochemical assays.

SH-SY5Y-APP cells were plated at 75,000 cells/well in 96-well tissue culture plates. After 16-18 h, the culture medium was replaced with fresh medium containing either compound or vehicle. Replicates of 3 wells per test concentration were used, with 10 concentrations at ½ log step intervals. Vehicle (0.12% DMSO) is included as a control.

A variety of animal models (e.g., male Hartley guinea pigs) including transgenic mouse models (e.g., Tg2576 or APP23) are used to assess the ability of a compound to affect the levels of specific Aβ peptide alloforms upon treatment of the animal using various routes of administration and various concentrations of the compound for various lengths of time and comparing the levels of specific Aβ peptide alloforms such as $A\beta_{42}$ and/or the level of occupancy of a given organ, such as the brain, by pathological lesions associated with specific Aβ peptide alloforms (e.g., Aβ deposits and/or Aβ plaques) and comparing to those effects achieved on animals treated with vehicle alone. See e.g., Lanz T A, et al., 2006, *J Pharmacol Exp Ther* 2006; 319: 924-933; Abramoswki D, et al., 2008, *J Pharmacol Exp Ther.* 327:411-424.

It has been shown that attenuation of $A\beta_{42}$ levels over an extended period of time dramatically reduces the number of neuritic plaques in Tg2576 transgenic mice (14). See e.g., Kounnas, M. Z. et al., 2010, Id. These data were generated following chronic treatment (7 months) with 50 mg/kg/day of an aminothiazole-bridged aromatic GSM or AGSM, similar in structure and function to the SGSMs that we have been optimizing and characterizing over the past two years. We have demonstrated that our SGSMs (bridged heterocycles) have dramatically improved physicochemical properties compared to the original bridged aromates, which should considerably facilitate both preclinical and clinical development of SGSMs. We have also recently shown that these SGSMs are also capable of statistically significant lowering of $A\beta_{42}$ levels in both plasma and brain of the Tg2576 AD transgenic mouse model.

Both the earlier reported AGSMs and the recently developed SGSMs have been shown to bind directly to the highly purified T-secretase enzyme complex. Recent studies have shown that FAD (i.e., familial Alzheimer's Disease) patients do indeed have increased fractional synthetic rates of $A\beta_{42}$ relative to $A\beta_{40}$ in their CNS when compared to non-carrier siblings, thus validating the clinical relevance of CNS $A\beta_{42}$ as a disease biomarker.

Example 1. Compounds and Biological Activities

Compounds disclosed herein were synthesized and assayed for biological activity (EC50) in a cell-based moderate throughput $A\beta_{42}$ ELISA that utilizes human SHSY5Y neuroblastoma cells stably overexpressing human APP695 wild-type, as known in the art. The results are tabulate in Table 1 following.

TABLE 1

Compounds, Biological Activities, and Mass Spectrometric results

| Cmpd No. | Structure | Aβ$_{42}$-IC$_{50}$, nM | ESI MS (M + H) |
|---|---|---|---|
| 003077 | 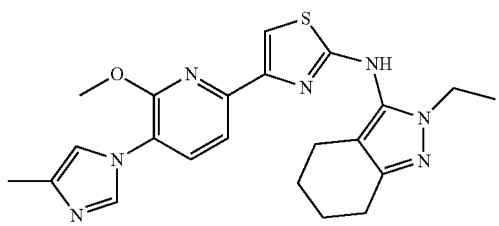 [SMILES: CCn1nc2c(c1Nc1nc(-c3ccc(-n4cnc(C)c4)c(OC)n3)cs1)CCCC2] | 56 | 436 |
| 003594 | 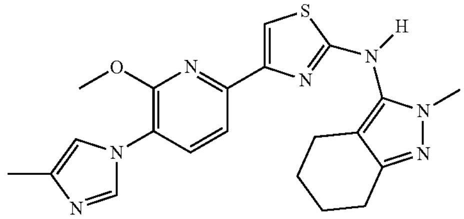 | | |
| 003625 | 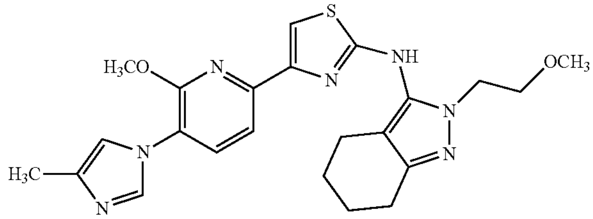 [SMILES: COCCn1nc2c(c1Nc1nc(-c3ccc(-n4cnc(C)c4)c(OC)n3)cs1)CCCC2] | | |
| 003697 | 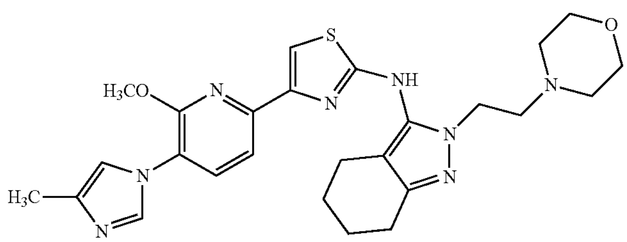 [SMILES: COc1nc(-c2csc(Nc3c4c(nn3CCN3CCOCC3)CCCC4)n2)ccc1-n1cnc(C)c1] | | |
| 003783 | 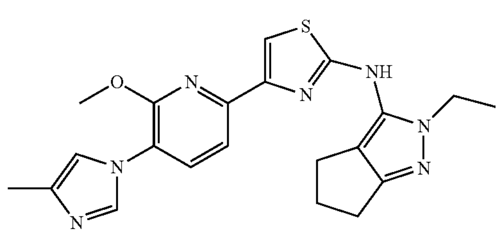 [SMILES: CCn1nc2c(c1Nc1nc(-c3ccc(-n4cnc(C)c4)c(OC)n3)cs1)CCC2] | 33 | 422 |
| 003838 | 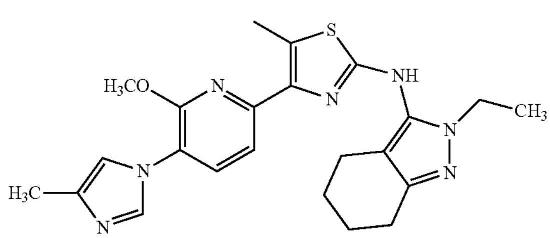 [SMILES: CCn1nc2c(c1Nc1nc(-c3ccc(-n4cnc(C)c4)c(OC)n3)c(C)s1)CCCC2] | | |

TABLE 1-continued

Compounds, Biological Activities, and Mass Spectrometric results

| Cmpd No. | Structure | Aβ₄₂-IC₅₀, nM | ESI MS (M + H) |
|---|---|---|---|
| 003929 | 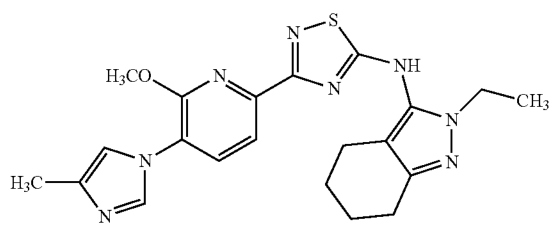 [SMILES: CCn1nc2c(c1Nc1nc(-c3ccc(-n4cnc(C)c4)c(OC)n3)ns1)CCCC2] | | |
| 004019 | 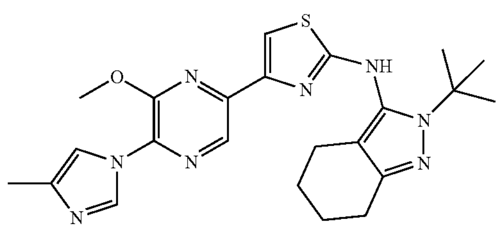 [SMILES: COc1nc(-c2csc(Nc3c4c(nn3C(C)(C)C)CCCC4)n2)cnc1-n1cnc(C)c1] | 71 | 464 |
| 004051 | 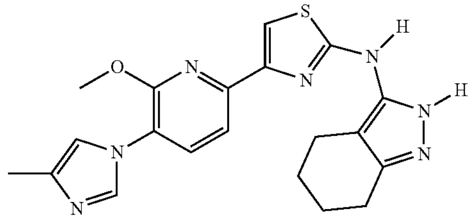 [SMILES: COc1nc(-c2csc(Nc3[nH]nc4c3CCCC4)n2)ccc1-n1cnc(C)c1] | | |
| 004102 | 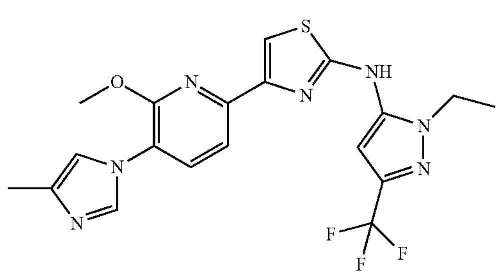 [SMILES: CCn1nc(C(F)(F)F)cc1Nc1nc(-c2ccc(-n3cnc(C)c3)c(OC)n2)cs1] | 57 | 450 |
| 004173 | 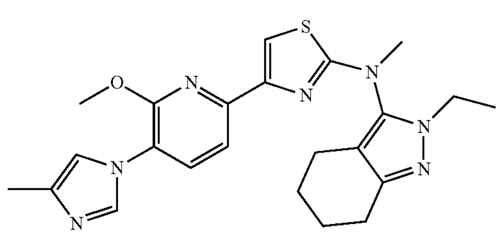 [SMILES: CCn1nc2c(c1N(C)c1nc(-c3ccc(-n4cnc(C)c4)c(OC)n3)cs1)CCCC2] | | |
| 004234 | 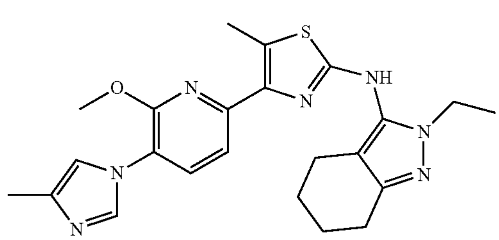 [SMILES: CCn1nc2c(c1Nc1nc(-c3ccc(-n4cnc(C)c4)c(OC)n3)c(C)s1)CCCC2] | 33 | 436 |

TABLE 1-continued
Compounds, Biological Activities, and Mass Spectrometric results
| Cmpd No. | Structure | Aβ42-IC50, nM | ESI MS (M + H) |
|---|---|---|---|
| 004269 | 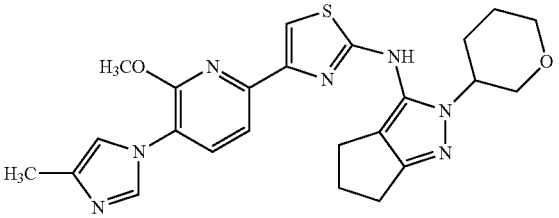 [SMILES: COc1nc(-c2csc(Nc3c4c(nn3C3CCCOC3)CCC4)n2)ccc1-n1cnc(C)c1] | | |
| 004346 | 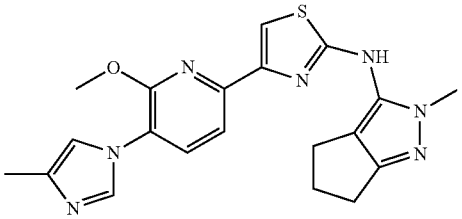 | 77 | 408 |
| 004365 | 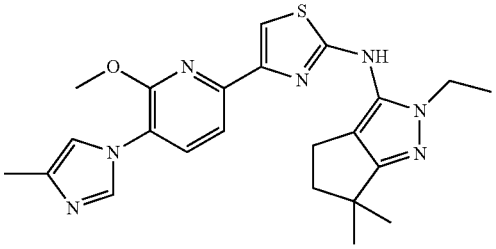 [SMILES: CCn1nc2c(c1Nc1nc(-c3ccc(-n4cnc(C)c4)c(OC)n3)cs1)CCC2(C)C] | 38 | 450 |
| 004476 | 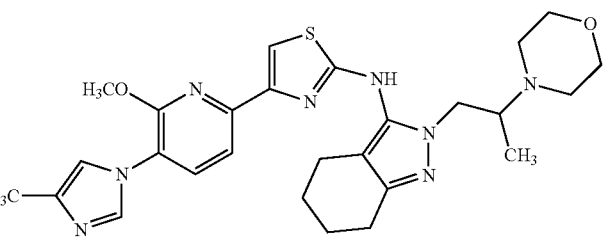 | | |
| 004721 | 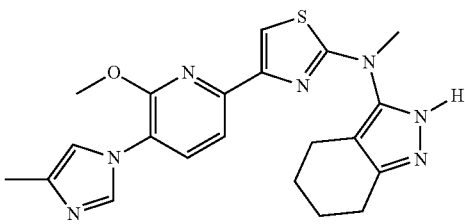 [SMILES: COc1nc(-c2csc(N(C)c3[nH]nc4c3CCCC4)n2)ccc1-n1cnc(C)c1] | | |
| 004723 | 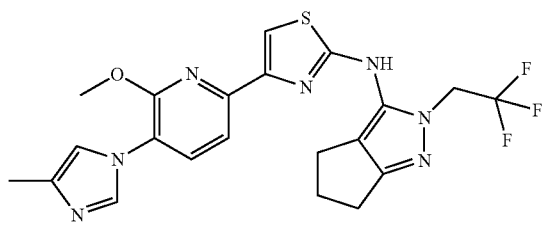 [SMILES: COc1nc(-c2csc(Nc3c4c(nn3CC(F)(F)F)CCC4)n2)ccc1-n1cnc(C)c1] | 35 | 476 |

TABLE 1-continued

Compounds, Biological Activities, and Mass Spectrometric results

| Cmpd No. | Structure | Aβ$_{42}$-IC$_{50}$, nM | ESI MS (M + H) |
|---|---|---|---|
| 13563 | 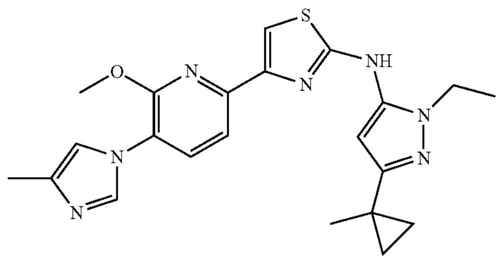 [SMILES: CCn1nc(C2(C)CC2)cc1Nc1nc(-c2ccc(-n3cnc(C)c3)c(OC)n2)cs1] | 24 | 436 |
| 13565 | 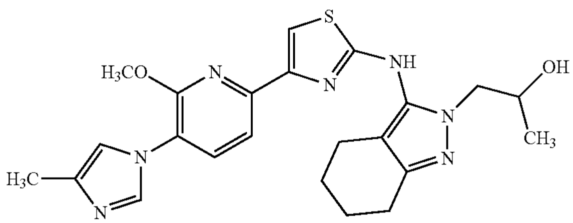 [SMILES: COc1nc(-c2csc(Nc3c4c(nn3CC(C)O)CCCC4)n2)ccc1-n1cnc(C)c1] | | |
| 13636 | 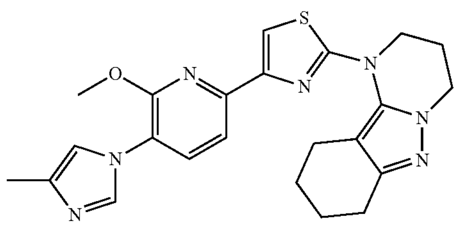 [SMILES: COc1nc(-c2csc(N3CCCn4nc5c(c43)CCCC5)n2)ccc1-n1cnc(C)c1] | 6 | 448 |
| 13674 | 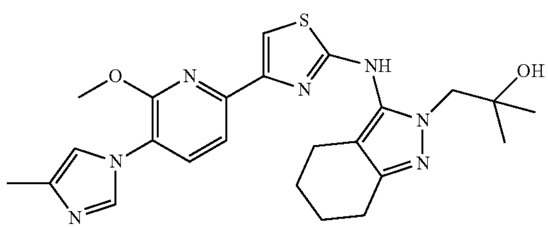 [SMILES: COc1nc(-c2csc(Nc3c4c(nn3CC(C)(C)O)CCCC4)n2)ccc1-n1cnc(C)c1] | 20 | 480 |
| 13680 | 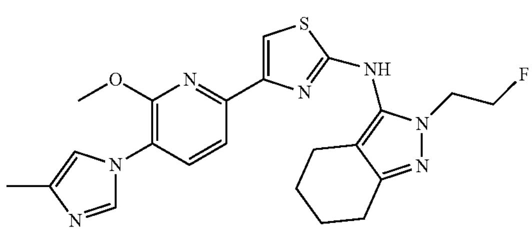 [SMILES: COc1nc(-c2csc(Nc3c4c(nn3CCF)CCCC4)n2)ccc1-n1cnc(C)c1] | 17 | 454 |
| 13765 | 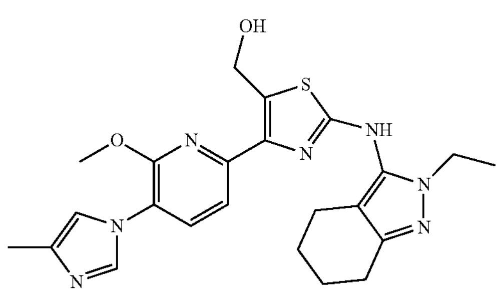 [SMILES: CCn1nc2c(c1Nc1nc(-c3ccc(-n4cnc(C)c4)c(OC)n3)c(CO)s1)CCCC2] | 35 | 466 |

TABLE 1-continued

Compounds, Biological Activities, and Mass Spectrometric results

| Cmpd No. | Structure | Aβ$_{42}$-IC$_{50}$, nM | ESI MS (M + H) |
|---|---|---|---|
| 13886 | 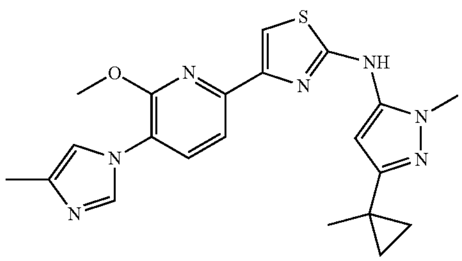 | 75 | 422 |
| 13887 | 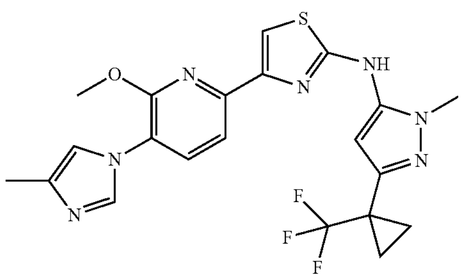 | 11 | 476 |
| 13921 | 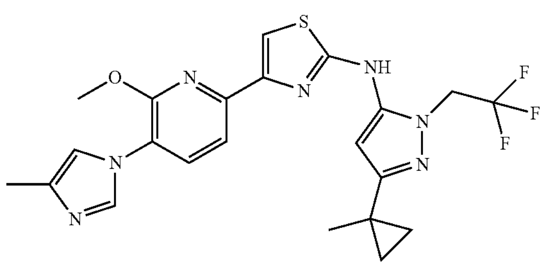 [SMILES: COc1nc(-c2csc(Nc3cc(C4(C)CC4)nn3CC(F)(F)F)n2)ccc1-n1cnc(C)c1] | 27 | 490 |
| 13922 | 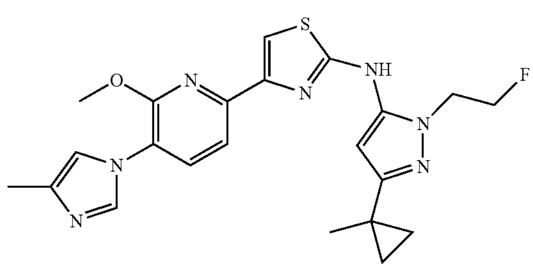 [SMILES: COc1nc(-c2csc(Nc3cc(C4(C)CC4)nn3CCF)n2)ccc1-n1cnc(C)c1] | 67 | 454 |
| 14034 | 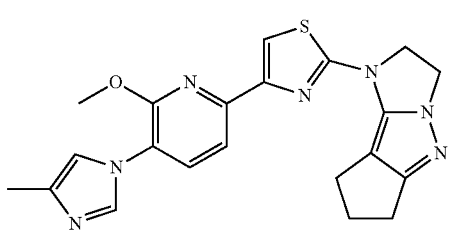 [SMILES: COc1nc(-c2csc(N3CCn4nc5c(c43)CCC5)n2)ccc1-n1cnc(C)c1] | | |
| 14035 | 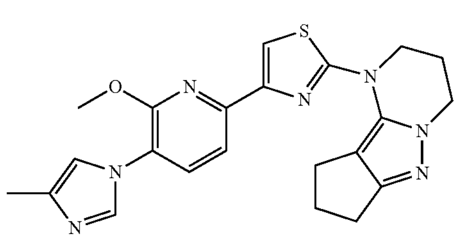 [SMILES: COc1nc(-c2csc(N3CCCn4nc5c(c43)CCC5)n2)ccc1-n1cnc(C)c1] | 19 | 434 |

TABLE 1-continued
Compounds, Biological Activities, and Mass Spectrometric results
| Cmpd No. | Structure | Aβ₄₂-IC₅₀, nM | ESI MS (M + H) |
|---|---|---|---|
| 14104 | 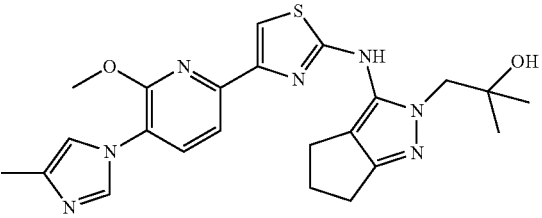 [SMILES: COc1nc(-c2csc(Nc3c4c(nn3CC(C)(C)O)CCC4)n2)ccc1-n1cnc(C)c1] | 39 | 466 |
| 14106 | 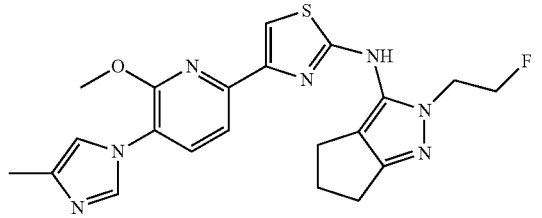 [SMILES: COc1nc(-c2csc(Nc3c4c(nn3CCF)CCC4)n2)ccc1-n1cnc(C)c1] | 64 | 440 |
| 14200 | 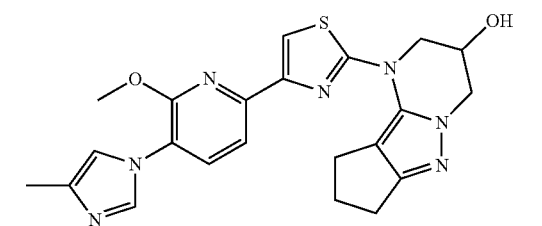 [SMILES: COc1nc(-c2csc(N3CC(O)Cn4nc5c(c43)CCC5)n2)ccc1-n1cnc(C)c1] | 44 | 450 |
| 14257 | 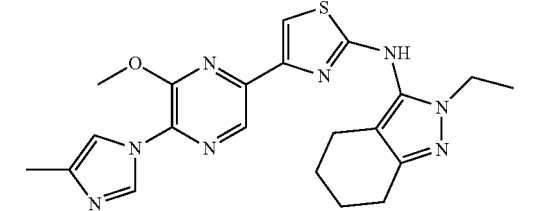 [SMILES: CCn1nc2c(c1Nc1nc(-c3cnc(-n4cnc(C)c4)c(OC)n3)cs1)CCCC2] | 89 | 437 |
| 14507 | 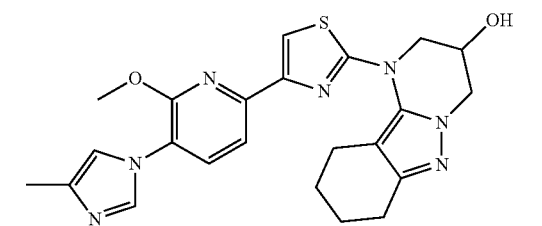 [SMILES: COc1nc(-c2csc(N3CC(O)Cn4nc5c(c43)CCCC5)n2)ccc1-n1cnc(C)c1] | 17 | 464 |
| 14508 | 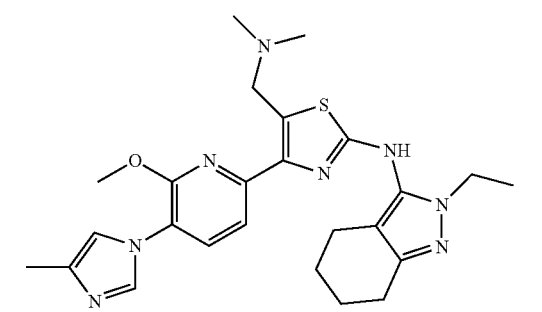 [SMILES: CCn1nc2c(c1Nc1nc(-c3ccc(-n4cnc(C)c4)c(OC)n3)c(CN(C)C)s1)CCCC2] | 85 | 493 |

TABLE 1-continued

Compounds, Biological Activities, and Mass Spectrometric results

| Cmpd No. | Structure | Aβ$_{42}$-IC$_{50}$, nM | ESI MS (M + H) |
|---|---|---|---|
| 14548 | 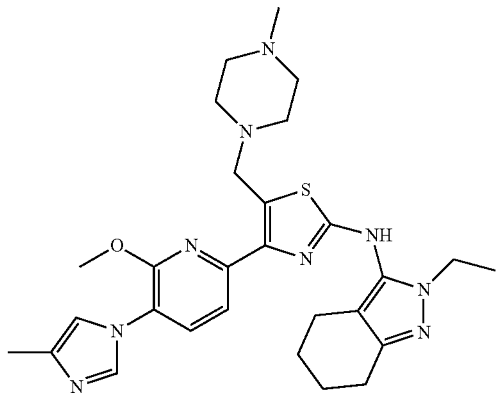 [SMILES: CCn1nc2c(c1Nc1nc(-c3ccc(-n4cnc(C)c4)c(OC)n3)c(CN3CCN(C)CC3)s1)CCCC2] | 98 | 548 |
| 14592 | 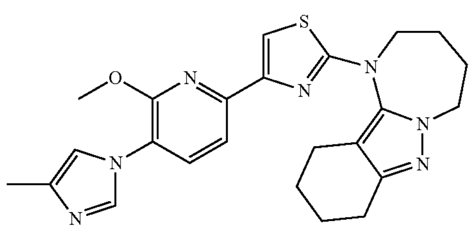 [SMILES: COc1nc(-c2csc(N3CCCCn4nc5c(c43)CCCC5)n2)ccc1-n1cnc(C)c1] | | |
| 14676 | 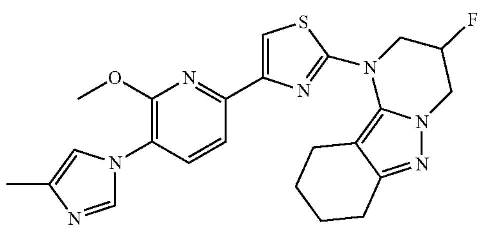 [SMILES: COc1nc(-c2csc(N3CC(F)Cn4nc5c(c43)CCCC5)n2)ccc1-n1cnc(C)c1] | 10 | 466 |
| 14780 | 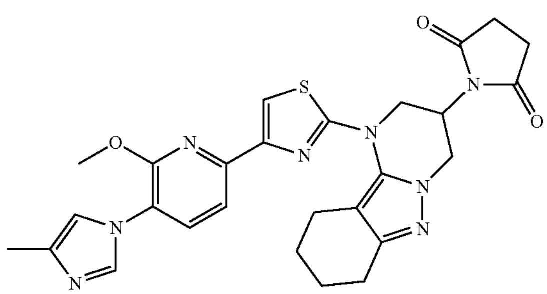 [SMILES: COc1nc(-c2csc(N3CC(N4C(=O)CCC4=O)Cn4nc5c(c43)CCCC5)n2)ccc1-n1cnc(C)c1] | 67 | 545 |
| 14789 A | 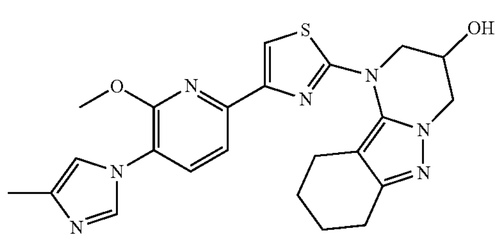 [SMILES: COc1nc(-c2csc(N3CC(O)Cn4nc5c(c43)CCCC5)n2)ccc1-n1cnc(C)c1] | 5 | 464 |

TABLE 1-continued

Compounds, Biological Activities, and Mass Spectrometric results

| Cmpd No. | Structure | Aβ$_{42}$-IC$_{50}$, nM | ESI MS (M + H) |
|---|---|---|---|
| 14789 B | 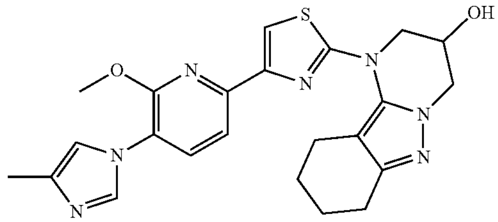 [SMILES: COc1nc(-c2csc(N3CC(O)Cn4nc5c(c43)CCCC5)n2)ccc1-n1cnc(C)c1] | 30 | 464 |
| 14839 | 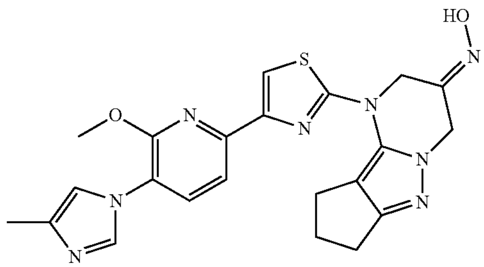 [SMILES: COc1nc(-c2csc(N3C/C(=N\O)Cn4nc5c(c43)CCC5)n2)ccc1-n1cnc(C)c1] | 57 | 463 |
| 14885 | 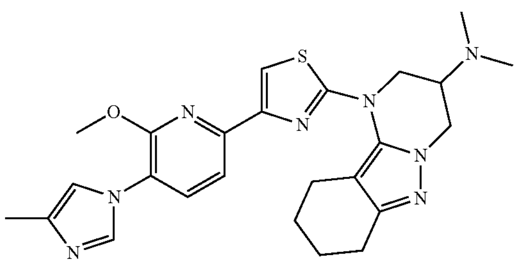 | 59 | 491 |
| 14945 | 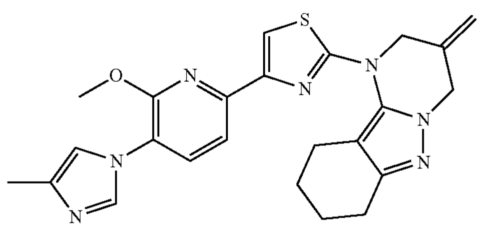 | 35 | 460 |
| 14946 | 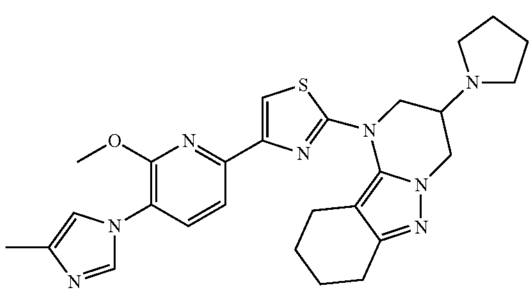 [SMILES: COc1nc(-c2csc(N3CC(N4CCCC4)Cn4nc5c(c43)CCCC5)n2)ccc1-n1cnc(C)c1] | 19 | 517 |
| 15001 | 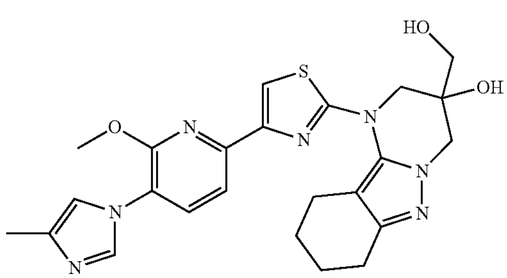 [SMILES: COc1nc(-c2csc(N3CC(O)(CO)Cn4nc5c(c43)CCCC5)n2)ccc1-n1cnc(C)c1] | 34 | 494 |

TABLE 1-continued
Compounds, Biological Activities, and Mass Spectrometric results
| Cmpd No. | Structure | Aβ$_{42}$-IC$_{50}$, nM | ESI MS (M + H) |
|---|---|---|---|
| 15002 | 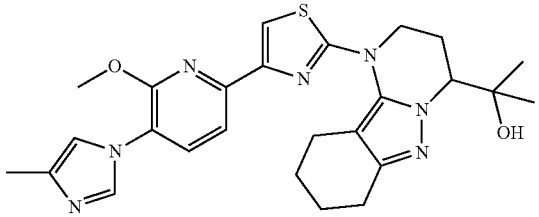 [SMILES: COc1nc(-c2csc(N3CCC(C(C)(C)O)n4nc5c(c43)CCCC5)n2)ccc1-n1cnc(C)c1] | 65 | 506 |
| 15003 | 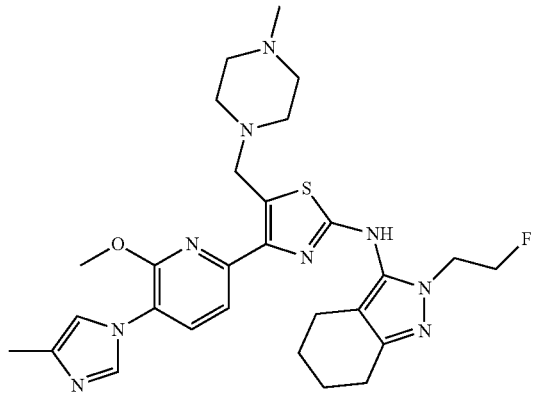 [SMILES: COc1nc(-c2nc(Nc3c4c(nn3CCF)CCCC4)sc2CN2CCN(C)CC2)ccc1-n1cnc(C)c1] | 50 | 566 |
| 15004 | 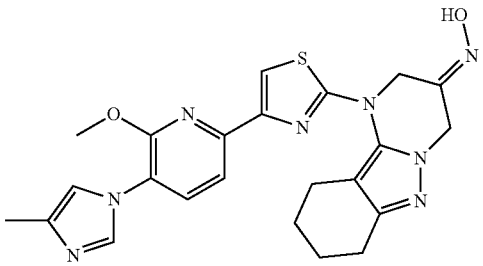 [SMILES: COc1nc(-c2csc(N3C/C(=N\O)Cn4nc5c(c43)CCCC5)n2)ccc1-n1cnc(C)c1] | 55 | 477 |
| 15188 | 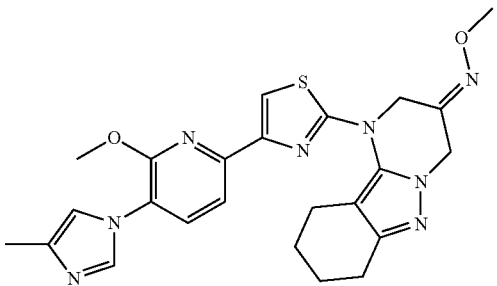 | 76 | 491 |

TABLE 1-continued

Compounds, Biological Activities, and Mass Spectrometric results

| Cmpd No. | Structure | Aβ$_{42}$-IC$_{50}$, nM | ESI MS (M + H) |
|---|---|---|---|
| 15473 | 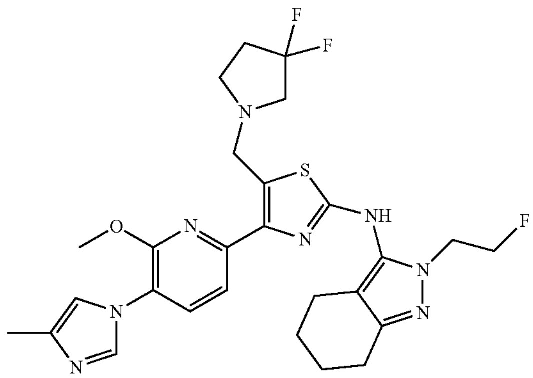 [SMILES: COc1nc(-c2nc(Nc3c4c(nn3CCF)CCCC4)sc2CN2CCC(F)(F)C2)ccc1-n1cnc(C)c1] | 99 | 573 |
| 15495 A | 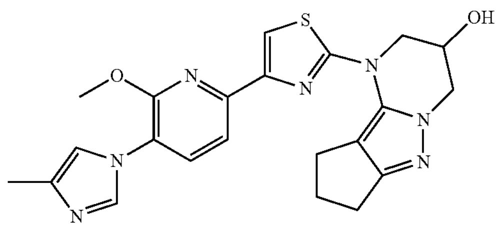 [SMILES: COc1nc(-c2csc(N3CC(O)Cn4nc5c(c43)CCC5)n2)ccc1-n1cnc(C)c1] | 53 | 450 |
| 15496 B | 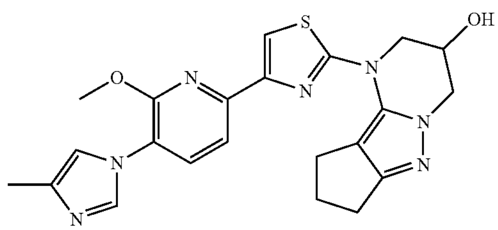 [SMILES: COc1nc(-c2csc(N3CC(O)Cn4nc5c(c43)CCC5)n2)ccc1-n1cnc(C)c1] | 33 | 450 |
| 14777 | 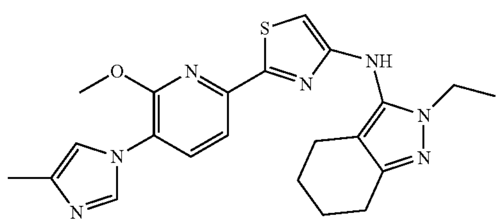 [SMILES: CCn1nc2c(c1Nc1csc(-c3ccc(-n4cnc(C)c4)c(OC)n3)n1)CCCC2] | 22 | 436 |
| 15587 | 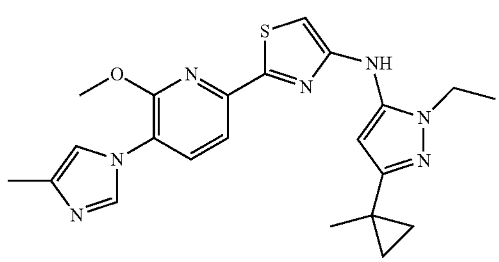 [SMILES: CCn1nc(C2(C)CC2)cc1Nc1csc(-c2ccc(-n3cnc(C)c3)c(OC)n2)n1] | 14 | 436 |
| 15635 | 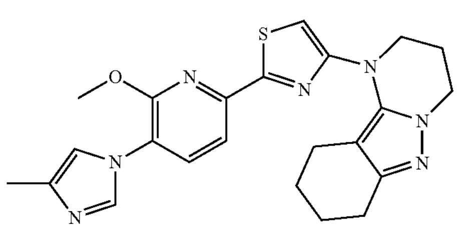 [SMILES: COc1nc(-c2nc(N3CCCn4nc5c(c43)CCCC5)cs2)ccc1-n1cnc(C)c1] | 7 | 448 |

TABLE 1-continued
Compounds, Biological Activities, and Mass Spectrometric results
| Cmpd No. | Structure | Aβ₄₂-IC₅₀, nM | ESI MS (M + H) |
|---|---|---|---|
| 15666 | 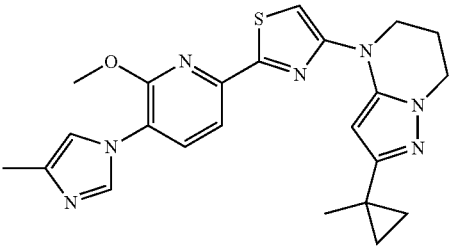 [SMILES: COc1nc(-c2nc(N3CCCn4nc(C5(C)CC5)cc43)cs2)ccc1-n1cnc(C)c1] | 18 | 448 |
| 15669 | 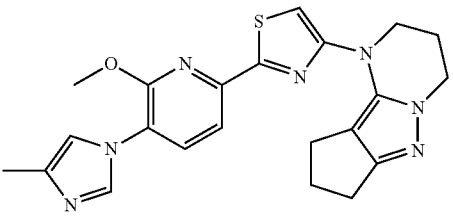 [SMILES: COc1nc(-c2nc(N3CCCn4nc5c(c43)CCC5)cs2)ccc1-n1cnc(C)c1] | 5 | 434 |
| 15670 | 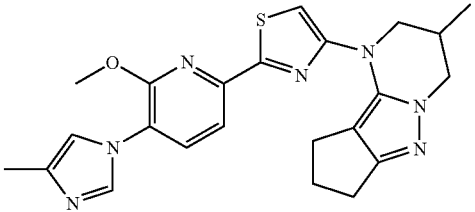 | 16 | 448 |
| 15717 | 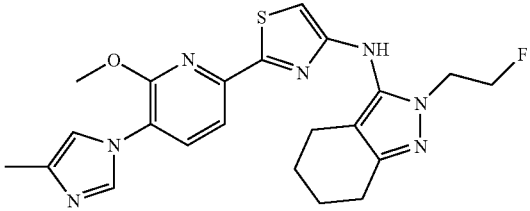 [SMILES: COc1nc(-c2nc(Nc3c4c(nn3CCF)CCCC4)cs2)ccc1-n1cnc(C)c1] | 48 | 454 |
| 15746 | 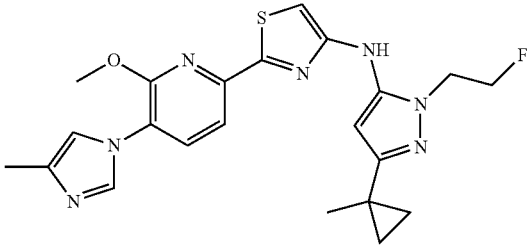 [SMILES: COc1nc(-c2nc(Nc3cc(C4(C)CC4)nn3CCF)cs2)ccc1-n1cnc(C)c1] | 56 | 454 |
| 15830 | 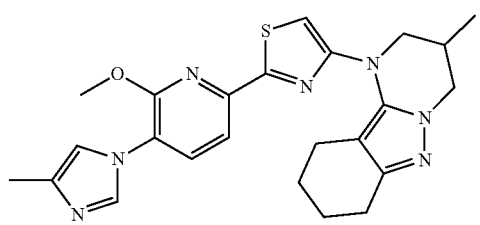 | 12 | 462 |

TABLE 1-continued

Compounds, Biological Activities, and Mass Spectrometric results

| Cmpd No. | Structure | $A\beta_{42}\text{-}IC_{50}$, nM | ESI MS (M + H) |
|---|---|---|---|
| 15868 | 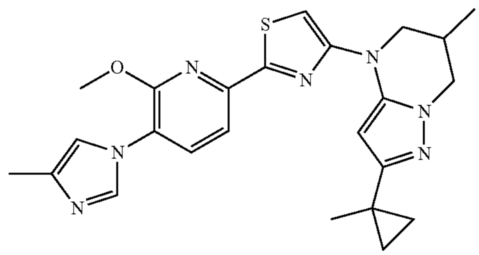 | 30 | 462 |
| 16211 | 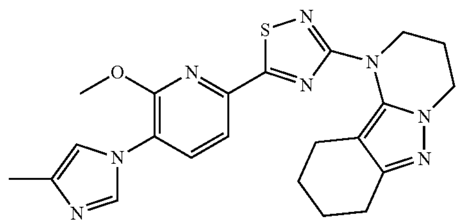 [SMILES: COc1nc(-c2nc(N3CCCn4nc5c(c43)CCCC5)ns2)ccc1-n1cnc(C)c1] | 41 | 449 |
| S20 | 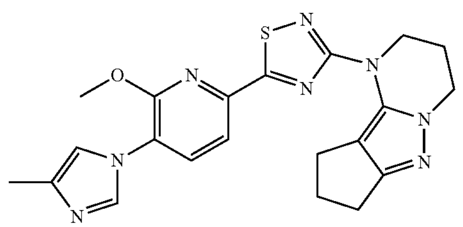 [SMILES: COc1nc(-c2nc(N3CCCn4nc5c(c43)CCC5)ns2)ccc1-n1cnc(C)c1] | | |
| S21 | 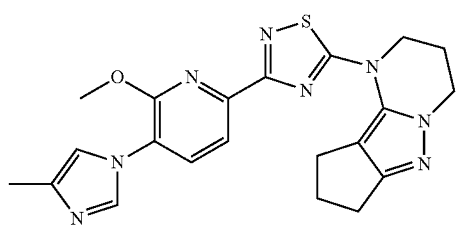 [SMILES: COc1nc(-c2nsc(N3CCCn4nc5c(c43)CCC5)n2)ccc1-n1cnc(C)c1] | | |

It is understood that the examples and embodiments described herein are for illustrative purposes only and that various modifications or changes in light thereof will be suggested to persons skilled in the art and are to be included within the spirit and purview of this application and scope of the appended claims. All publications, patents, and patent applications cited herein are hereby incorporated by reference in their entirety for all purposes.

VI. Embodiments

Embodiments P1-P12 follow:

Embodiment P1

An isolated soluble gamma secretase modulator (SGSM) or pharmaceutically acceptable salt or prodrug thereof, comprising lipophilic or hydrophilic group substitution(s) on aminothiazole "C" ring or pyrazole "D" ring of compound BPN-3077-AA-1,

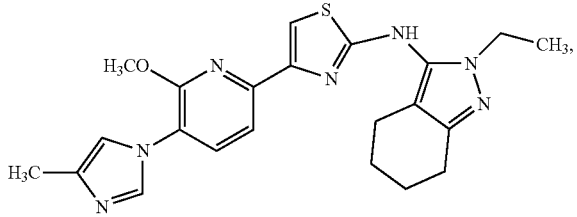 [SMILES: CCn1nc2c(c1Nc1nc(-c3ccc(-n4cnc(C)c4)c(OC)n3)cs1)CCCC2]

having the structure:

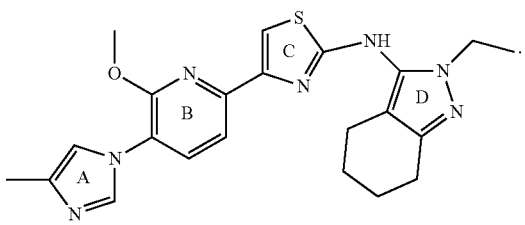

Embodiment P2

The isolated soluble gamma secretase modulator (SGSM) or pharmaceutically acceptable salt or prodrug thereof of Embodiment P1, wherein the substitution(s) increases kinetic solubility.

Embodiment P3

The isolated soluble gamma secretase modulator (SGSM) or pharmaceutically acceptable salt or prodrug thereof of Embodiment P1, wherein the increased kinetic solubility is an increase of at least 2-fold in phosphate buffered saline at pH 7.4.

Embodiment P4

The soluble gamma secretase modulator or pharmaceutically acceptable salt or prodrug thereof of Embodiment P1, wherein the soluble gamma secretase modulator or pharmaceutically acceptable salt or prodrug thereof has the chemical structure of:

a)

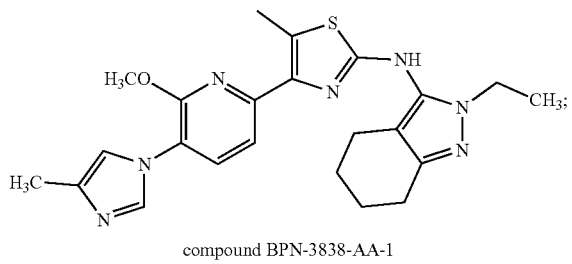

compound BPN-3838-AA-1 b)

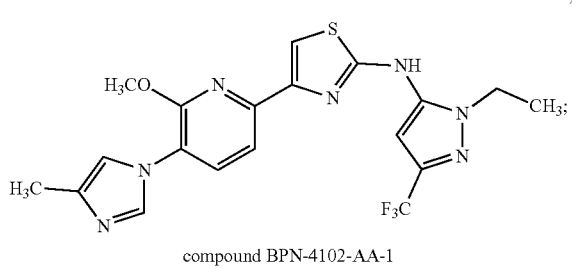

compound BPN-4102-AA-1 c)

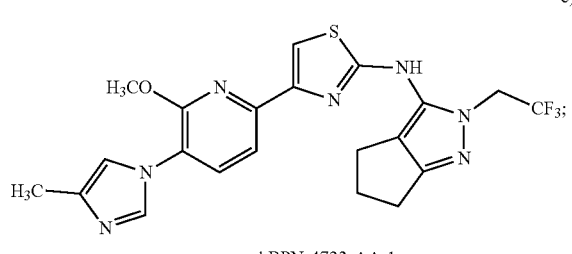

compound BPN-4723-AA-1 d)

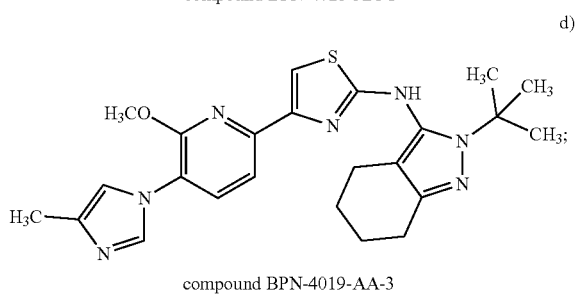

compound BPN-4019-AA-3

-continued e)

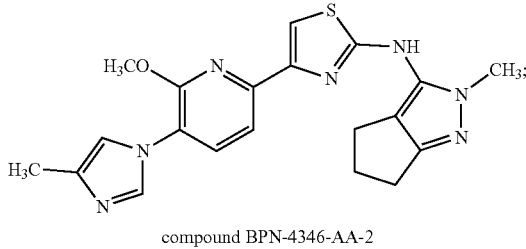

compound BPN-4346-AA-2 f)

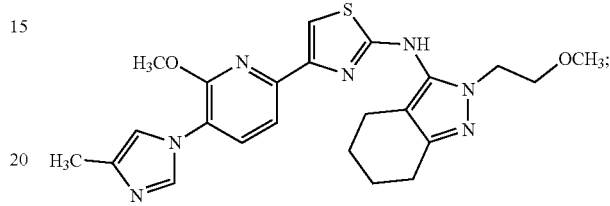

compound BPN-3625-AA-1 g)

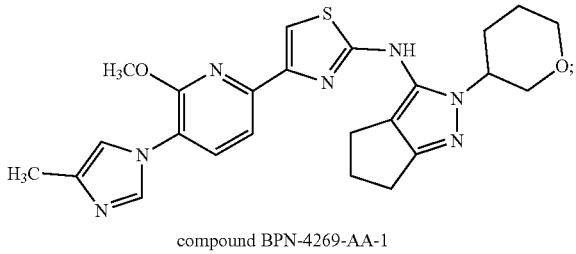

compound BPN-4269-AA-1 h)

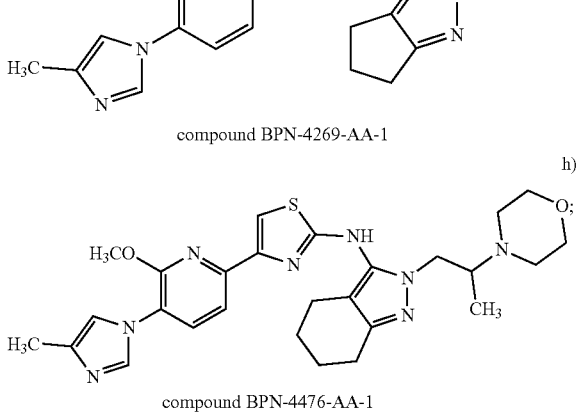

compound BPN-4476-AA-1 i)

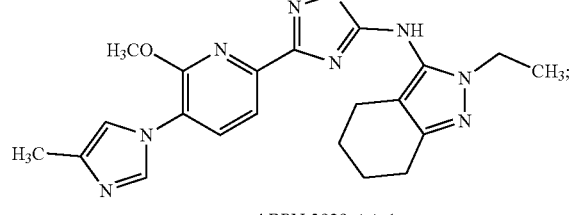

compound BPN-3929-AA-1 j)

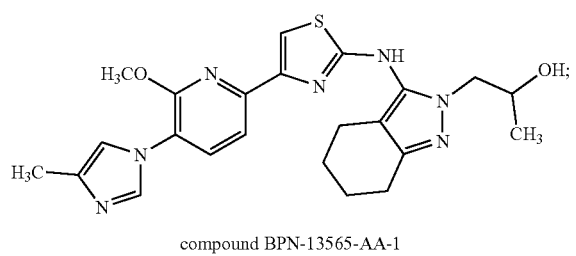

compound BPN-13565-AA-1

-continued

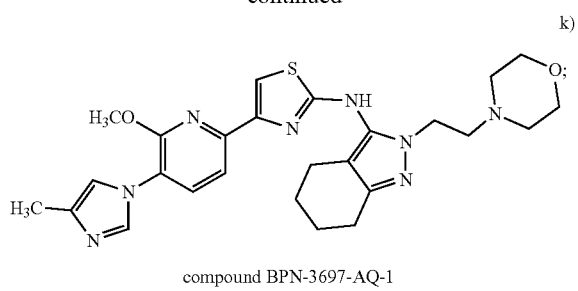
compound BPN-3697-AQ-1

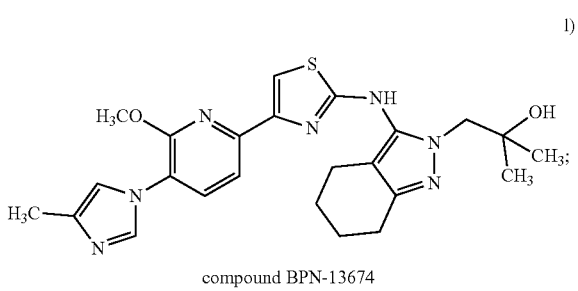
compound BPN-13674

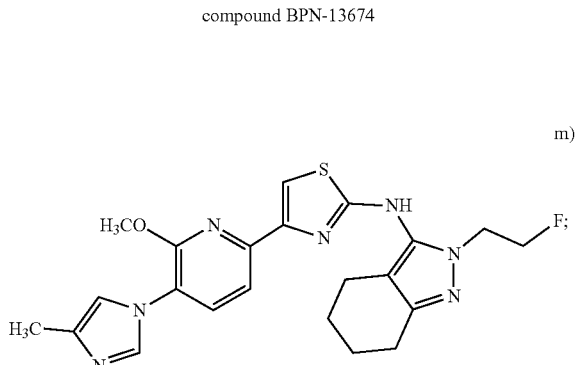
compound BPN-13680

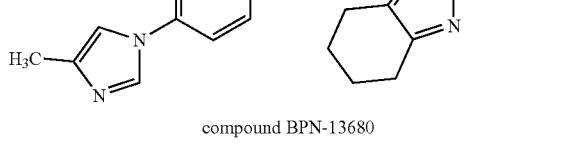
compound BPN-3783-AA-1

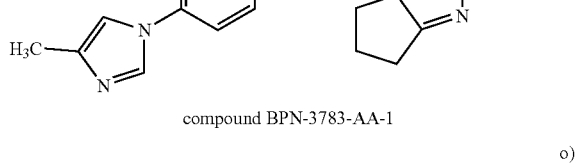
compound BPN-13563

-continued

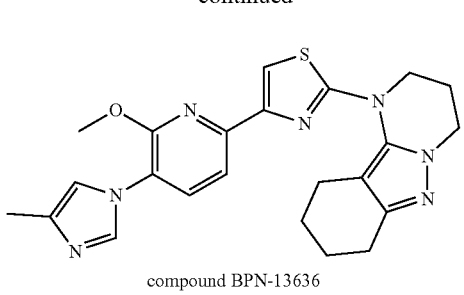
compound BPN-13636

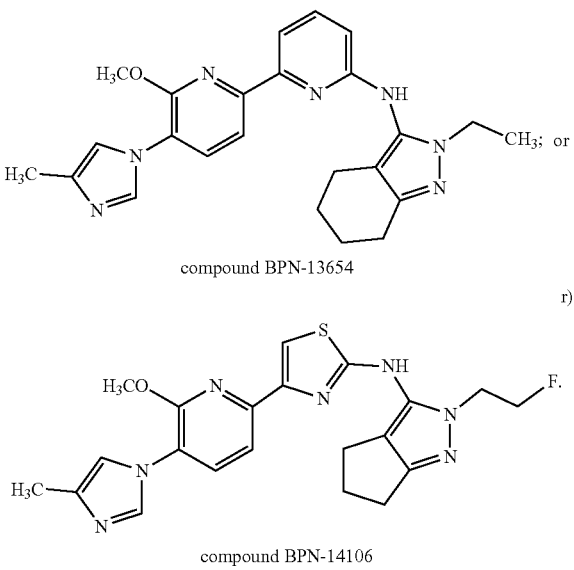

compound BPN-13654 compound BPN-14106

Embodiment P5

A soluble gamma secretase modulator or pharmaceutically acceptable salt or prodrug thereof, wherein the soluble gamma secretase modulator or pharmaceutically acceptable salt or prodrug thereof has the chemical structure of:

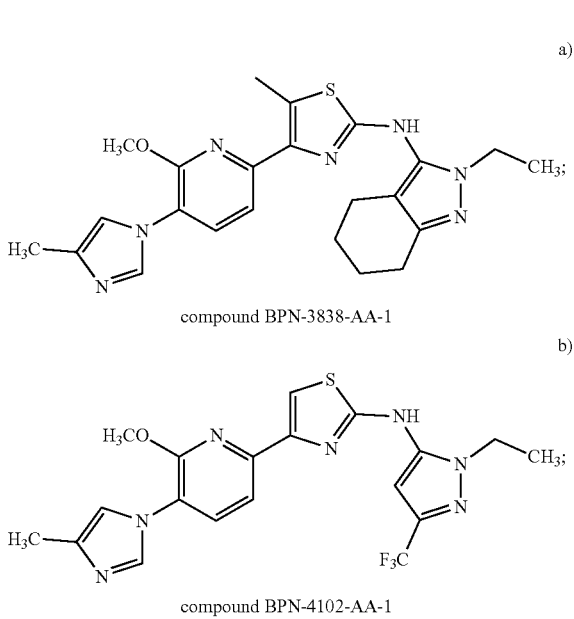

compound BPN-3838-AA-1 compound BPN-4102-AA-1

-continued
c)
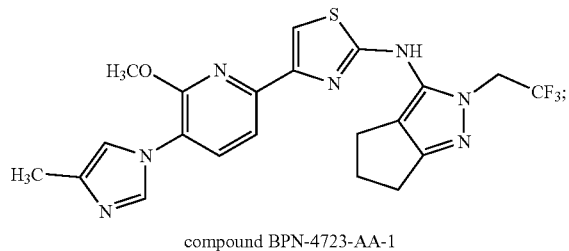
compound BPN-4723-AA-1
d)
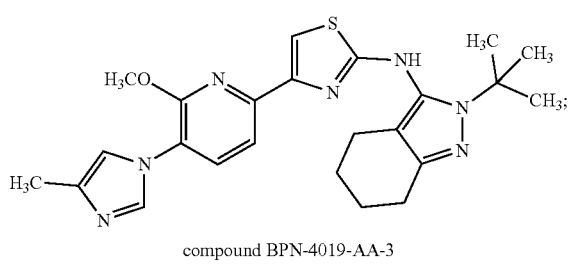
compound BPN-4019-AA-3
e)
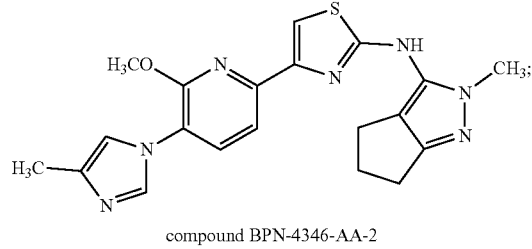
compound BPN-4346-AA-2
f)
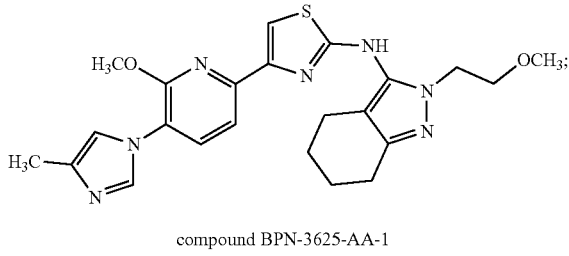
compound BPN-3625-AA-1
g)
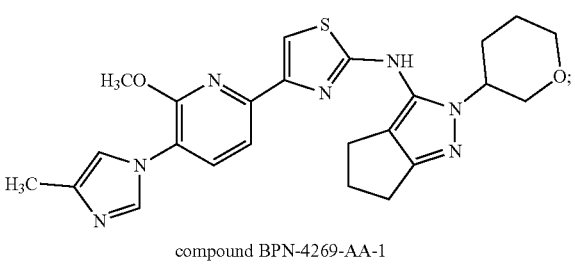
compound BPN-4269-AA-1
-continued
h)
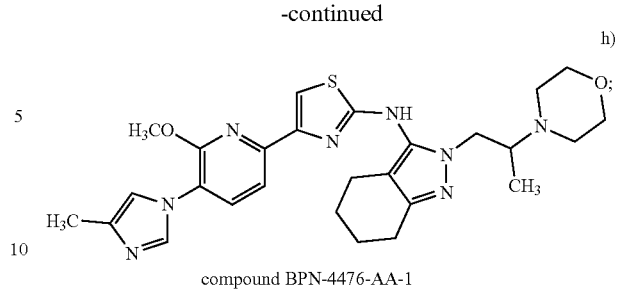
compound BPN-4476-AA-1
i)
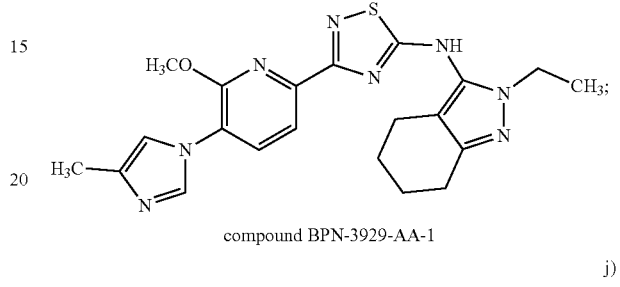
compound BPN-3929-AA-1
j)
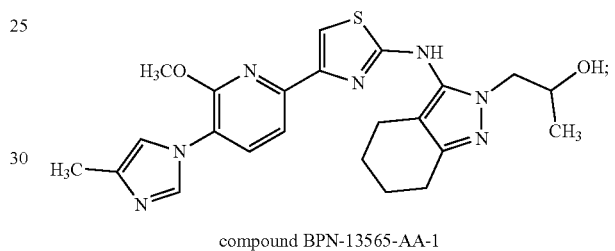
compound BPN-13565-AA-1
k)
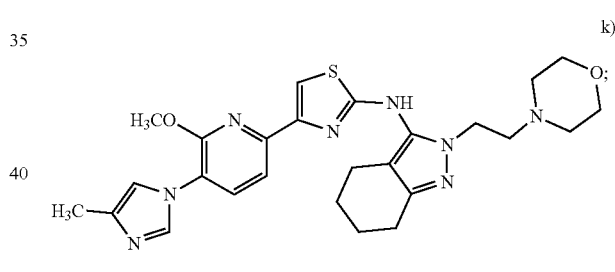
compound BPN-3697-AQ-1
l)
compound BPN-13674
m)
compound BPN-13680

-continued n)

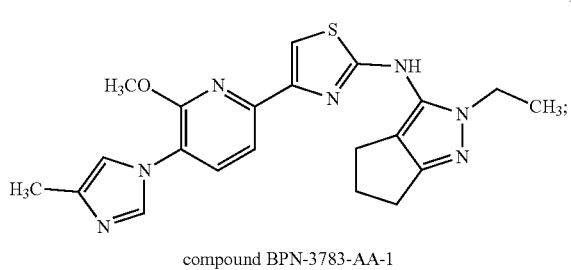

compound BPN-3783-AA-1 o)

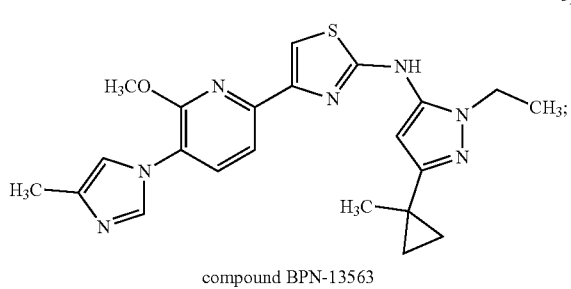

compound BPN-13563 p)

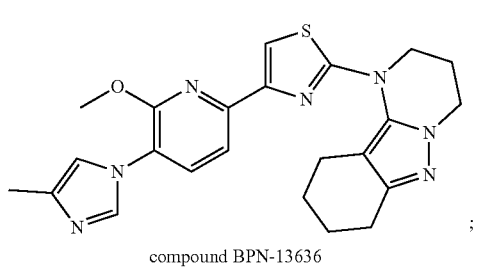

compound BPN-13636 q)

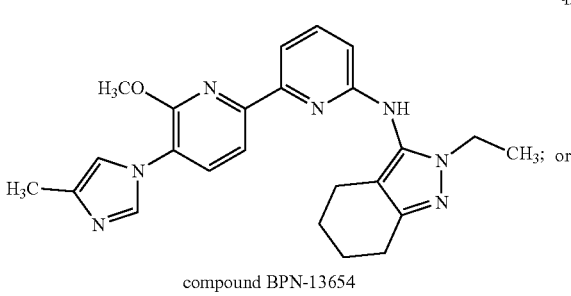

compound BPN-13654 r)

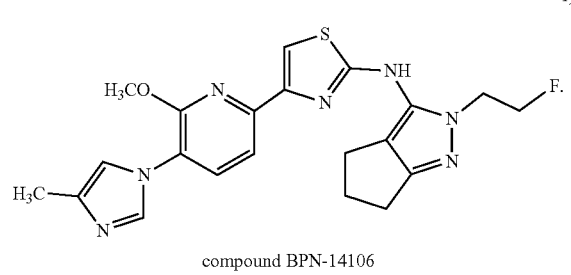

compound BPN-14106

Embodiment P6

A pharmaceutical composition comprising the compound of Embodiment P1 and a pharmaceutically acceptable carrier.

Embodiment P7

The pharmaceutical composition of Embodiment P6, wherein the composition is compressed into a tablet, minitablet or caplet or encapsulated in a capsule.

Embodiment P8

The pharmaceutical composition of Embodiment P7, wherein the tablet, minitablet, caplet or capsule is administered to a patient once or twice daily.

Embodiment P9

A method of inhibiting production of $A\beta_{42}$ or $A\beta_{40}$ comprising contacting a protease which proteolyzes an amyloid precursor protein (APP) or fragment thereof with an effective amount of a compound of Embodiment P1 so as to inhibit production of $A\beta_{42}$ or $A\beta_{40}$.

Embodiment P10

The method of Embodiment P9, wherein the compound of Embodiment P1 has no measurable effect on gamma-secretase-mediated processing of Notch-1 receptor or no adverse effect associated with any altered Notch-1 receptor signaling.

Embodiment P11

A method for treating a disease or neurological disorder associated with elevated levels of specific fibrillogenic Aβ peptides by inhibiting production of $A\beta_{42}$ or $A\beta_{40}$ by the method of Embodiment P9.

Embodiment P12

The method of Embodiment P11, wherein the disease is selected from a group consisting of but not limited to Alzheimer's disease, Down Syndrome (DS), hemorrhagic stroke associated with cerebrovascular amyloidosis (HCHWA), cerebral amyloid angiopathy (CAA), idiophathic dilated cardiomyopathy, hereditary cerebral hemorrhage with amyloidosis, Dutch type (HCHWA-D), prion disorders, Creutzfeldt-Jakob disease (CJD), frontotemporal dementias (FTD), amyolropic lateral sclerosis (ALS), Huntington's disease (HD), Parkinson's disease (PD) and other neurodegenerative proteinopathies.

Further embodiments 1-139 follow.

Embodiment 1

A compound having the formula:

(I)

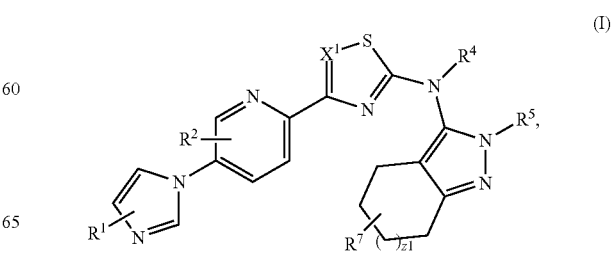

-continued

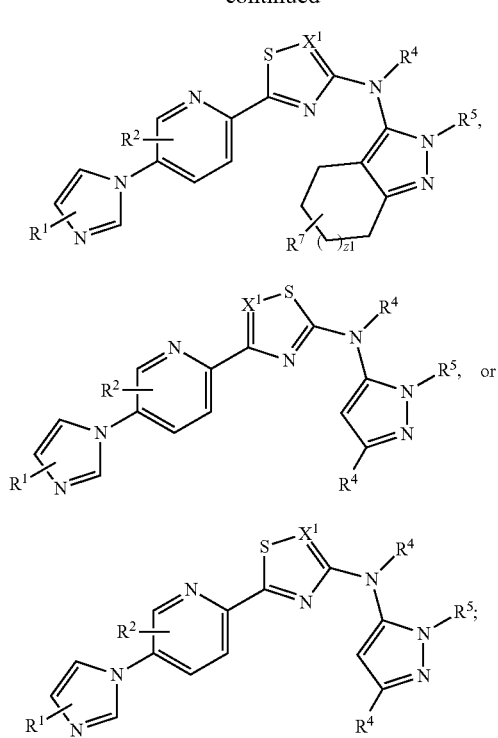

wherein, z1 is 0, 1 or 2; $X^1$ is $C(R^3)$ or N; $R^1$ is hydrogen, halogen, —$N_3$, —$CF_3$, —$CCl_3$, —$CBr_3$, —$CI_3$, —CN, —CHO, —$OR^{1A}$, —$NR^{1A}R^{1B}$, —$COOR^{1A}$, —$C(O)NR^{1A}R^{1B}$, —$NO_2$, —$SR^{1A}$, —$S(O)_{n1}OR^{1A}$, —$S(O)_{n1}NR^{1A}R^{1B}$, —$NHNR^{1A}R^{1B}$, —$ONR^{1A}R^{1B}$, —$NHC(O)NHNR^{1A}R^{1B}$, substituted or unsubstituted alkyl, substituted or unsubstituted heteroalkyl, substituted or unsubstituted cycloalkyl, substituted or unsubstituted heterocycloalkyl, substituted or unsubstituted aryl, or substituted or unsubstituted heteroaryl; $R^2$ is hydrogen, halogen, —$N_3$, —$CF_3$, —$CCl_3$, —$CBr_3$, —$CI_3$, —CN, —CHO, —$OR^{2A}$, —$NR^{2A}R^{2B}$, —$COOR^{2A}$, —$C(O)NR^{2A}R^{2B}$, —$NO_2$, —$SR^{2A}$, —$S(O)_{n2}R^{2A}$, —$S(O)_{n2}OR^{2A}$, —$S(O)_{n2}NR^{2A}R^{2B}$, —$NHNR^{2A}R^{2B}$, —$ONR^{2A}R^{2B}$, —$NHC(O)NHNR^{2A}R^{2B}$, substituted or unsubstituted alkyl, substituted or unsubstituted heteroalkyl, substituted or unsubstituted cycloalkyl, substituted or unsubstituted heterocycloalkyl, substituted or unsubstituted aryl, or substituted or unsubstituted heteroaryl; $R^3$ is hydrogen, halogen, —$N_3$, —$CF_3$, —$CCl_3$, —$CBr_3$, —$CI_3$, —CN, —CHO, —$OR^{3A}$, —$NR^{3A}R^{3B}$, —$COOR^{3A}$, —$C(O)NR^{3A}R^{3B}$, —$NO_2$, —$SR^{3A}$, —$S(O)_{n3}R^{3A}$, —$S(O)_{n3}OR^{3A}$, —$S(O)_{n3}NR^{3A}R^{3B}$, —$NHNR^{3A}R^{3B}$, —$ONR^{3A}R^{3B}$, —$NHC(O)NHNR^{3A}R^{3B}$, substituted or unsubstituted alkyl, substituted or unsubstituted heteroalkyl, substituted or unsubstituted cycloalkyl, substituted or unsubstituted heterocycloalkyl, substituted or unsubstituted aryl, or substituted or unsubstituted heteroaryl; $R^4$ is hydrogen, halogen, —$N_3$, —$CF_3$, —$CCl_3$, —$CBr_3$, —$CI_3$, —CN, —CHO, —$OR^{4A}$, —$NR^{4A}R^{4B}$, —$COOR^{4A}$, —$C(O)NR^{4A}R^{4B}$, —$NO_2$, —$SR^{4A}$, —$S(O)_{n4}R^{4A}$, —$S(O)_{n4}OR^{4A}$, —$S(O)_4NR^{4A}R^{4B}$, —$NHNR^{4A}R^{4B}$, —$ONR^{4A}R^{4B}$, —$NHC(O)NHNR^{4A}R^{4B}$, substituted or unsubstituted alkyl, substituted or unsubstituted heteroalkyl, substituted or unsubstituted cycloalkyl, substituted or unsubstituted heterocycloalkyl, substituted or unsubstituted aryl, or substituted or unsubstituted heteroaryl; $R^5$ is hydrogen, halogen, —$N_3$, —$CF_3$, —$CCl_3$, —$CBr_3$, —$CI_3$, —CN, —CHO, —$OR^{5A}$, —$NR^{5A}R^{5B}$, —$COOR^{5A}$, —$C(O)NR^{5A}R^{5B}$, —$NO_2$, —$SR^{5A}$, —$S(O)_{n5}R^{5A}$, —$S(O)_{n5}OR^{5A}$, —$S(O)_{n5}NR^{5A}R^{5B}$, —$NHNR^{5A}R^{5B}$, —$ONR^{5A}R^{5B}$, —$NHC(O)NHNR^{5A}R^{5B}$, substituted or unsubstituted alkyl, substituted or unsubstituted heteroalkyl, substituted or unsubstituted cycloalkyl, substituted or unsubstituted heterocycloalkyl, substituted or unsubstituted aryl, or substituted or unsubstituted heteroaryl, wherein $R^4$ and $R^5$ are optionally joined together to form a substituted or unsubstituted heterocycloalkyl or substituted or unsubstituted heteroaryl; $R^6$ is —$CF_3$, substituted or unsubstituted cyclopropyl, or substituted or unsubstituted cyclobutyl; $R^7$ is independently hydrogen, halogen, —$N_3$, —$CF_3$, —$CCl_3$, —$CBr_3$, —$CI_3$, —CN, —CHO, —$OR^{7A}$, —$NR^{7A}R^{7B}$, —$COOR^{7A}$, —$C(O)NR^{7A}R^{7B}$, —$NO_2$, —$SR^{7A}$, —$S(O)_{n7}R^{7A}$, —$S(O)_{n7}OR^{7A}$, —$S(O)_{n7}NR^{7A}R^{7B}$, —$NHNR^{7A}R^{7B}$, —$ONR^{7A}R^{7B}$, —$NHC(O)NHNR^{7A}R^{7B}$, substituted or unsubstituted alkyl, substituted or unsubstituted heteroalkyl, substituted or unsubstituted cycloalkyl, substituted or unsubstituted heterocycloalkyl, substituted or unsubstituted aryl, or substituted or unsubstituted heteroaryl; $R^{1A}$, $R^{1B}$, $R^{2A}$, $R^{2B}$, $R^{3A}$, $R^{3B}$, $R^{4A}$, $R^{4B}$, $R^{5A}$, $R^{5B}$, $R^{7A}$ and $R^{7B}$ are independently hydrogen, substituted or unsubstituted alkyl, substituted or unsubstituted heteroalkyl, substituted or unsubstituted cycloalkyl, substituted or unsubstituted heterocycloalkyl, substituted or unsubstituted aryl, or substituted or unsubstituted heteroaryl; and n1, n2, n3, n4, n5 and n7 are independently 1 or 2.

Embodiment 2

The compound of embodiment 1, wherein z1 is 0.

Embodiment 3

The compound of embodiment 1, wherein z1 is 1.

Embodiment 4

The compound of embodiment 1, wherein z1 is 2.

Embodiment 5

The compound of embodiment 1, having the formula:

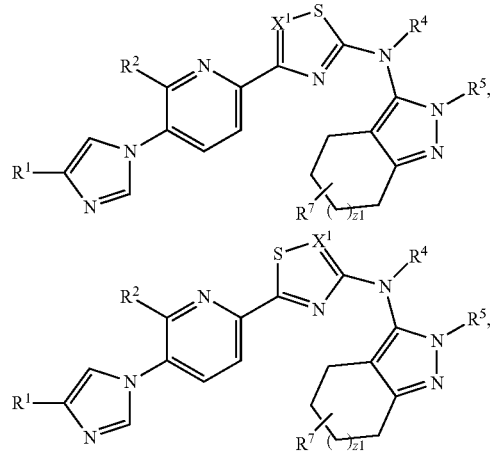

-continued

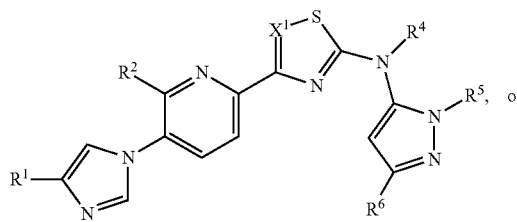

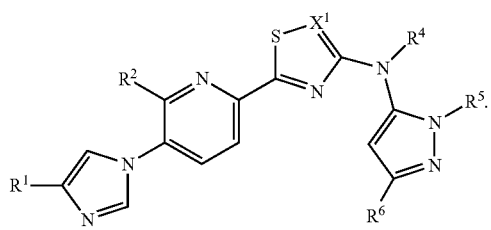

Embodiment 6

The compound of embodiment 1, having the formula:

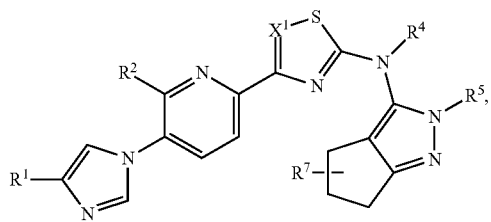

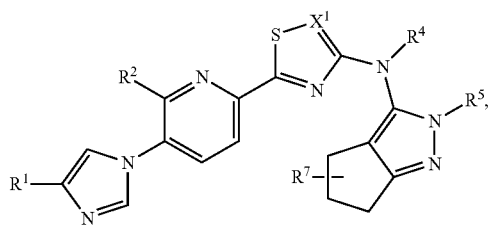

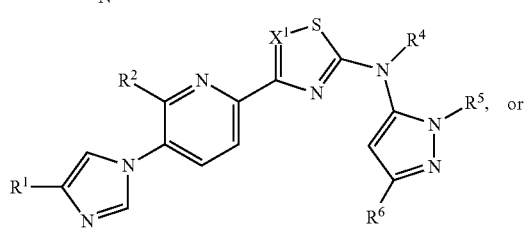

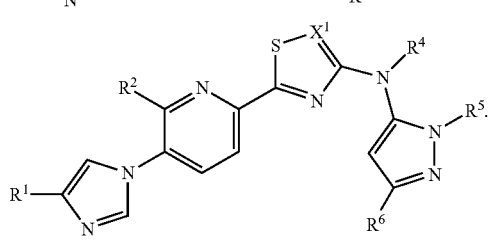

Embodiment 7

The compound of embodiment 1, having the formula:

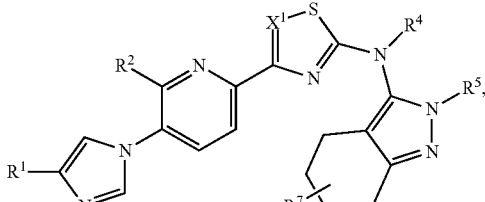

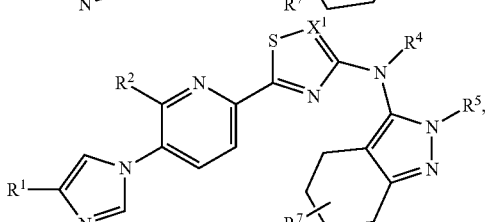

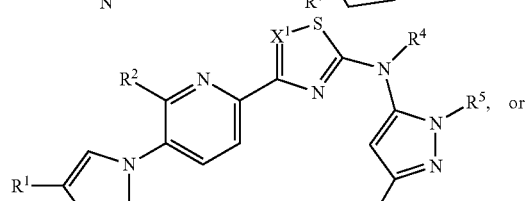

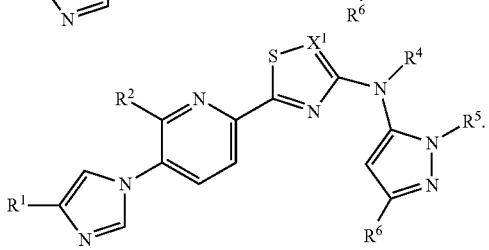

Embodiment 8

The compound of any one of embodiments 1 to 7 wherein $R^1$ is substituted or unsubstituted alkyl.

Embodiment 9

The compound of embodiment 8, wherein $R^1$ is unsubstituted alkyl.

Embodiment 10

The compound of embodiment 9, wherein $R^1$ is unsubstituted $C_1$-$C_6$ alkyl.

Embodiment 11

The compound of embodiment 10, wherein $R^1$ is methyl.

Embodiment 12

The compound of any one of embodiments 1 to 7, wherein $R^2$ is hydrogen or —$OR^{2A}$.

Embodiment 13

The compound of embodiment 12, wherein $R^{2.A}$ is hydrogen, or substituted or unsubstituted alkyl.

Embodiment 14

The compound of embodiment 13, wherein $R^{2.A}$ is unsubstituted alkyl.

Embodiment 15

The compound of embodiment 14, wherein $R^{2.A}$ is unsubstituted $C_1$-$C_6$ alkyl.

Embodiment 16

The compound of embodiment 15, wherein $R^{2.A}$ is methyl.

Embodiment 17

The compound of any one of embodiments 1 to 7 wherein $R^3$ is hydrogen, halogen, —$CF_3$, —$CCl_3$, —$CBr_3$, —$CI_3$, —CN, substituted or unsubstituted alkyl, substituted or unsubstituted heteroalkyl, substituted or unsubstituted cycloalkyl, or substituted or unsubstituted heterocycloalkyl.

Embodiment 18

The compound of embodiment 17, wherein $R^3$ is hydrogen.

Embodiment 19

The compound of embodiment 17, wherein $R^3$ is unsubstituted alkyl.

Embodiment 20

The compound of embodiment 19, wherein $R^3$ is unsubstituted $C_1$-$C_{10}$ alkyl

Embodiment 21

The compound of embodiment 20, wherein $R^3$ is methyl, ethyl, n-propyl or isopropyl.

Embodiment 22

The compound of embodiment 17, wherein $R^3$ is substituted alkyl.

Embodiment 23

The compound of embodiment 17, wherein $R^3$ is substituted $C_1$-$C_6$ alkyl.

Embodiment 24

The compound of embodiment 23, wherein $R^3$ is $R^{3.A1}$-substituted alkyl.

Embodiment 25

The compound of embodiment 24, wherein $R^{3.A1}$ is halogen.

Embodiment 26

The compound of embodiment 25, wherein $R^3$ is —$CH_2F$, —$CHF_2$, —$CH_2$—$CF_3$, —$CH_2$—$CHF_2$ or —$CH_2$—$CH_2F$.

Embodiment 27

The compound of embodiment 24, wherein $R^{3.A1}$ is —OH.

Embodiment 28

The compound of embodiment 27, wherein $R^3$ is —$CH_2OH$, —$(CH_2)_2OH$, —$(CH_2)_3OH$, or —$CH_2$—$C(CH_3)_2OH$.

Embodiment 29

The compound of embodiment 24, wherein $R^{3.A1}$ is $R^{3.A2}$-substituted or unsubstituted heterocycloalkyl.

Embodiment 30

The compound of embodiment 29, wherein $R^{3.A2}$ is halogen or unsubstituted $C_1$-$C_6$ alkyl.

Embodiment 31

The compound of embodiment 30, wherein $R^3$ is methyl substituted with 4-methylpiperazin-1-yl, or methyl substituted with 3,3-difluoropyrrolidin-1-yl.

Embodiment 32

The compound of embodiment 17, wherein $R^3$ is substituted or unsubstituted heteroalkyl.

Embodiment 33

The compound of embodiment 32, wherein $R^3$ is unsubstituted 2 to 10 membered heteroalkyl.

Embodiment 34

The compound of embodiment 32, wherein $R^3$ is substituted 2 to 10 membered heteroalkyl.

Embodiment 35

The compound of embodiment 34, wherein $R^3$ is $R^{3.A1}$-substituted 2 to 10 membered heteroalkyl.

Embodiment 36

The compound of embodiment 35, wherein $R^{3.A1}$ is unsubstituted $C_1$-$C_3$ alkyl.

Embodiment 37

The compound of embodiment 36, wherein $R^3$ is —$CH_2$—O—$CH_3$, —$(CH_2)_2$—O—$CH_3$, —$CH_2NHCH_3$, —$(CH_2)_2NHCH_3$, —$CH_2N(CH_3)_2$, or —$(CH_2)_2N(CH_3)_2$.

Embodiment 38

The compound of embodiment 17, wherein $R^3$ is substituted or unsubstituted cycloalkyl.

Embodiment 39

The compound of embodiment 38, wherein $R^3$ is unsubstituted $C_3$-$C_8$ cycloalkyl.

Embodiment 40

The compound of embodiment 39, wherein $R^3$ is cyclopropyl, cyclobutyl, cyclopentyl or cyclohexyl.

Embodiment 41

The compound of embodiment 38, wherein $R^3$ is substituted $C_3$-$C_8$ cycloalkyl.

Embodiment 42

The compound of embodiment 17, wherein $R^3$ is substituted or unsubstituted heterocycloalkyl.

Embodiment 43

The compound of embodiment 42, wherein $R^3$ is unsubstituted heterocycloalkyl.

Embodiment 44

The compound of embodiment 42, wherein $R^3$ is unsubstituted 3 to 6 membered heterocycloalkyl.

Embodiment 45

The compound of embodiment 44, wherein $R^3$ is oxiranyl, oxetanyl, tetrahydrofuranyl, or tetrahydro-2H-pyranyl.

Embodiment 46

The compound of any one of embodiments 1 to 7, wherein $R^4$ is hydrogen, or substituted or unsubstituted alkyl.

Embodiment 47

The compound of embodiment 46, wherein $R^4$ is hydrogen.

Embodiment 48

The compound of embodiment 46, wherein $R^4$ is unsubstituted alkyl.

Embodiment 49

The compound of embodiment 48, wherein $R^4$ is unsubstituted $C_1$-$C_3$ alkyl

Embodiment 50

The compound of embodiment 49, wherein $R^4$ is methyl, ethyl, n-propyl, or isopropyl.

Embodiment 51

The compound of embodiment 50, wherein $R^4$ is methyl.

Embodiment 52

The compound of any one of embodiments 1 to 7, wherein $R^5$ is hydrogen, substituted or unsubstituted alkyl, substituted or unsubstituted heteroalkyl, substituted or unsubstituted cycloalkyl, or substituted or unsubstituted heterocycloalkyl.

Embodiment 53

The compound of embodiment 52, wherein $R^5$ is hydrogen.

Embodiment 54

The compound of embodiment 52, wherein $R^5$ is unsubstituted alkyl.

Embodiment 55

The compound of embodiment 54, wherein $R^5$ is unsubstituted $C_1$-$C_3$ alkyl.

Embodiment 56

The compound of embodiment 55, wherein $R^5$ is methyl, ethyl, n-propyl, isopropyl, isobutyl or pentyl.

Embodiment 57

The compound of embodiment 52, wherein $R^5$ is substituted alkyl.

Embodiment 58

The compound of embodiment 57, wherein $R^5$ is substituted $C_1$-$C_{10}$ alkyl.

Embodiment 59

The compound of embodiment 57, wherein $R^5$ is $C_1$-$C_{10}$ alkyl substituted with unsubstituted heterocycloalkyl.

Embodiment 60

The compound of embodiment 59, wherein said unsubstituted heterocycloalkyl is morpholinyl.

Embodiment 61

The compound of embodiment 60, wherein $R^5$ is —$(CH_2)_2$-morpholinyl or —$CH_2CH(CH_3)$-morpholinyl.

Embodiment 62

The compound of embodiment 58, wherein $R^5$ is —$CH_2F$, —$CH_2CH_2F$, —$CH_2CF_3$, —$(CH_2)_2OH$, —$C(CH_3)_2OH$, —$CH_2CH(CH_3)OH$, or —$CH_2C(CH_3)_2OH$.

Embodiment 63

The compound of embodiment 58, wherein $R^5$ is $R^{5A1}$-substituted $C_1$-$C_{10}$ alkyl.

Embodiment 64

The compound of embodiment 63, wherein $R^{5A1}$ is substituted or unsubstituted cycloalkyl.

Embodiment 65

The compound of embodiment 64, wherein $R^5$ is —(CH$_2$)-cyclopropyl or —(CH$_2$)$_2$-cyclopropyl.

Embodiment 66

The compound of embodiment 52, wherein $R^5$ is substituted or unsubstituted heteroalkyl.

Embodiment 67

The compound of embodiment 66, wherein $R^5$ is unsubstituted 2 to 8 membered heteroalkyl.

Embodiment 68

The compound of embodiment 67, wherein $R^5$ is —CH$_2$OCH$_3$, or —(CH$_2$)$_2$OCH$_3$.

Embodiment 69

The compound of embodiment 52, wherein $R^5$ is substituted or unsubstituted cycloalkyl.

Embodiment 70

The compound of embodiment 69, wherein $R^5$ is unsubstituted C$_3$-C$_8$ cycloalkyl.

Embodiment 71

The compound of embodiment 70, wherein $R^5$ is cyclopropyl, cyclobutyl, cyclopentyl, or cyclohexyl.

Embodiment 72

The compound of embodiment 52, wherein $R^5$ is substituted or unsubstituted heterocycloalkyl.

Embodiment 73

The compound of embodiment 72, wherein $R^5$ is unsubstituted 3 to 8 membered heterocycloalkyl.

Embodiment 74

The compound of embodiment 73, wherein $R^5$ is tetrahydro-2H-pyranyl.

Embodiment 75

The compound of any one of embodiments 1 to 7, wherein $R^6$ is —CF$_3$.

Embodiment 76

The compound of any one of embodiments 1 to 7, wherein $R^7$ is independently hydrogen, —CF$_3$, or unsubstituted alkyl.

Embodiment 77

The compound of embodiment 76, said compound comprising a plurality of independent $R^7$ substituents.

Embodiment 78

The compound of embodiment 77, said compound comprising two independent $R^7$ substituents.

Embodiment 79

The compound of embodiment 76, wherein $R^7$ is independently unsubstituted alkyl.

Embodiment 80

The compound of embodiment 79, wherein $R^7$ is independently unsubstituted C$_1$-C$_5$ alkyl.

Embodiment 81

The compound of embodiment 80, wherein $R^7$ is independently methyl, ethyl, n-propyl, isopropyl, isobutyl or pentyl.

Embodiment 82

The compound of any one of embodiments 1 to 7, wherein $X^1$ is C(R$^3$), and R$^3$ and R$^7$ are hydrogen.

Embodiment 83

The compound of any one of embodiments 1 to 7, wherein $X^1$ is C(R$^3$), R$^3$ and R$^7$ are hydrogen, R$^1$ is unsubstituted alkyl, and R$^2$ is —OR$^{2A}$.

Embodiment 84

The compound of any one of embodiments 1 to 7, wherein $X^1$ is C(R$^3$), R$^3$ and R$^7$ are hydrogen, R$^1$ is unsubstituted C$_1$-C$_5$ alkyl, and R$^2$ is —OR$^{2A}$, wherein R$^{2A}$ is unsubstituted C$_1$-C$_5$ alkyl.

Embodiment 85

The compound of any one of embodiments 1 to 7, wherein $X^1$ is C(R$^3$), R$^3$ and R$^7$ are hydrogen, R$^1$ is methyl, and R$^2$ is —OCH$_3$.

Embodiment 86

The compound of any one of embodiments 1 to 7, wherein $X^1$ is N.

Embodiment 87

The compound of embodiment 1, having the formula:

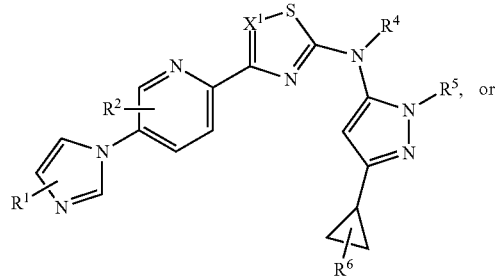

-continued

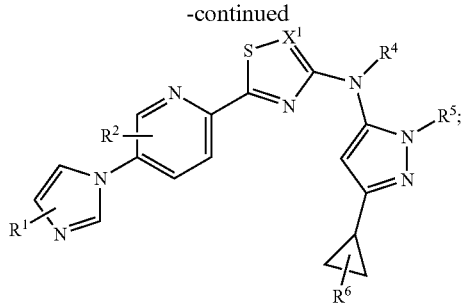

wherein, $R^8$ is independently hydrogen, halogen, —$N_3$, —$CF_3$, —$CCl_3$, —$CBr_3$, —CN, —CHO, —$OR^{8A}$, —$NR^{8A}R^{8B}$, —$COOR^{8A}$, —$C(O)NR^{8A}R^{8B}$, —$NO_2$, —$SR^{8A}$, —$S(O)_{n8}R^{8A}$, $S(O)_{n8}OR^{8A}$, —$S(O)_{n8}NR^{8A}R^{8B}$, —$NHNR^{8A}R^{8B}$, —$ONR^{8A}R^{8B}$, —$NHC(O)NHNR^{8A}R^{8B}$, substituted or unsubstituted alkyl, substituted or unsubstituted heteroalkyl, substituted or unsubstituted cycloalkyl, substituted or unsubstituted heterocycloalkyl, substituted or unsubstituted aryl, or substituted or unsubstituted heteroaryl; $R^{8A}$ and $R^{8B}$ are independently hydrogen, substituted or unsubstituted alkyl, substituted or unsubstituted heteroalkyl, substituted or unsubstituted cycloalkyl, substituted or unsubstituted heterocycloalkyl, substituted or unsubstituted aryl, or substituted or unsubstituted heteroaryl; and n8 is 1 or 2.

Embodiment 88

The compound of embodiment 87 having the formula:

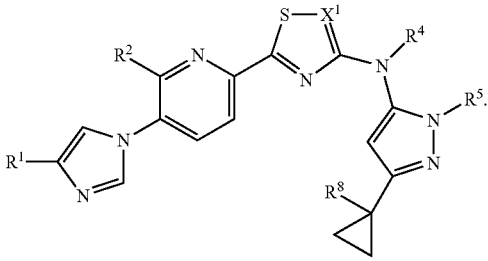

Embodiment 89

The compound of embodiment 88, having the formula:

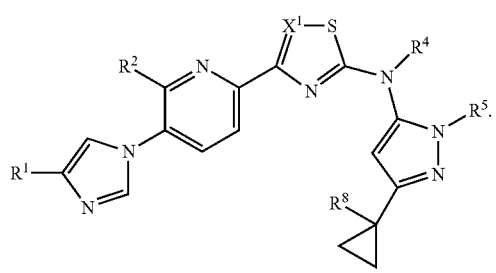

Embodiment 90

The compound of embodiment 88, having the formula:

Embodiment 91

The compound of embodiment 1, said compound having the formula:

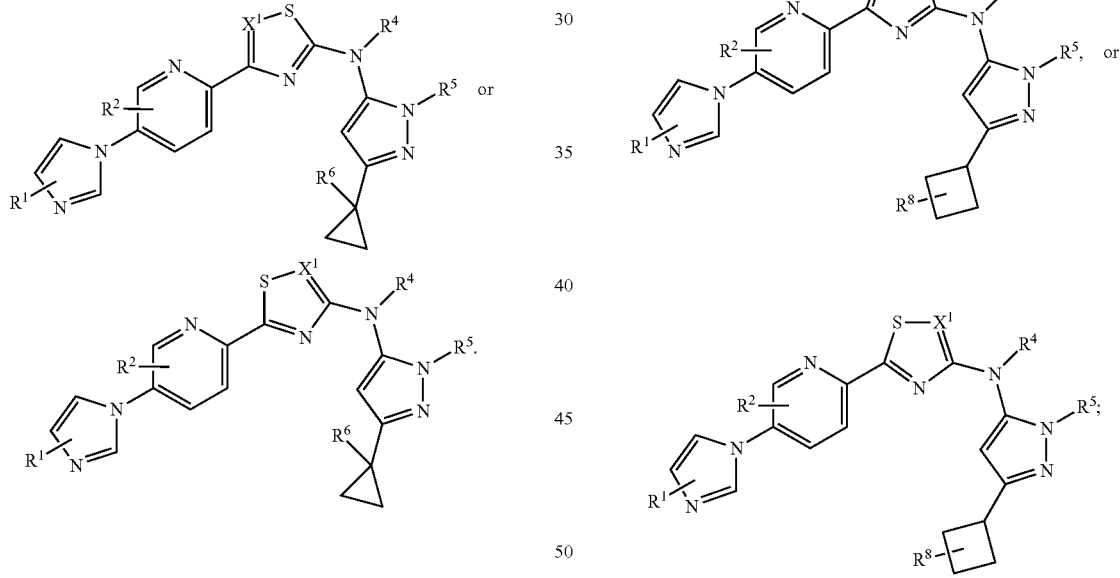

wherein, $R^8$ is independently hydrogen, halogen, —$N_3$, —$CF_3$, —$CCl_3$, —$CBr_3$, —CN, —CHO, —$OR^{8A}$, —$NR^{8A}R^{8B}$, —$COOR^{8A}$, —$C(O)NR^{8A}R^{8B}$, —$NO_2$, —$SR^{8A}$, —$S(O)_{n8}R^{8A}$, $S(O)_{n8}OR^{8A}$, —$S(O)_{n8}NR^{8A}R^{8B}$, —$NHNR^{8A}R^{8B}$, —$ONR^{8A}R^{8B}$, —$NHC(O)NHNR^{8A}R^{8B}$, substituted or unsubstituted alkyl, substituted or unsubstituted heteroalkyl, substituted or unsubstituted cycloalkyl, substituted or unsubstituted heterocycloalkyl, substituted or unsubstituted aryl, or substituted or unsubstituted heteroaryl; $R^{8A}$ and $R^{8B}$ are independently hydrogen, substituted or unsubstituted alkyl, substituted or unsubstituted heteroalkyl, substituted or unsubstituted cycloalkyl, substituted or unsubstituted heterocycloalkyl, substituted or unsubstituted aryl, or substituted or unsubstituted heteroaryl; and n8 is 1 or 2.

Embodiment 92

The compound of embodiment 91 having the formula:

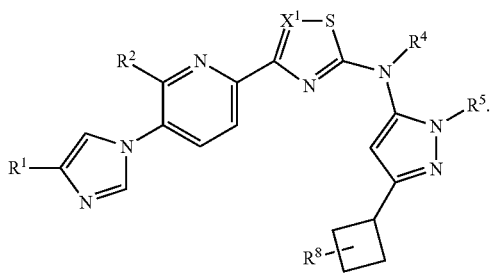

Embodiment 93

The compound of embodiment 91 having the formula:

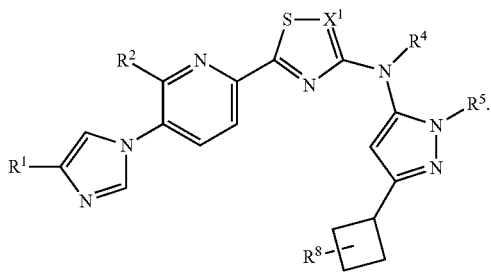

Embodiment 94

The compound of any one of embodiments 87 to 93, wherein $R^8$ is independently hydrogen, halogen, —$CF_3$, or substituted or unsubstituted alkyl.

Embodiment 95

The compound of embodiment 94, wherein $R^8$ is —$CF_3$.

Embodiment 96

The compound of embodiment 94, wherein $R^8$ is unsubstituted alkyl.

Embodiment 97

The compound of embodiment 94, wherein $R^8$ is unsubstituted $C_1$-$C_6$ alkyl.

Embodiment 98

The compound of embodiment 97, wherein $R^8$ is methyl, ethyl, n-propyl, isopropyl, isobutyl or pentyl.

Embodiment 99

The compound of embodiment 98, wherein $R^8$ is methyl.

Embodiment 100

The compound of any one of embodiments 87 to 93, wherein $X^1$ is $C(R^3)$, $R^3$ is hydrogen, $R^1$ is unsubstituted alkyl, $R^2$ is —$OR^{2A}$ and $R^8$ is unsubstituted alkyl.

Embodiment 101

The compound of any one of embodiments 87 to 93, wherein $X^1$ is $C(R^3)$, $R^3$ is hydrogen, $R^1$ is unsubstituted $C_1$-$C_5$ alkyl, $R^2$ is —$OR^{2A}$ and $R^8$ is unsubstituted $C_1$-$C_5$ alkyl, wherein $R^{2A}$ is unsubstituted $C_1$-$C_5$ alkyl.

Embodiment 102

The compound of any one of embodiments 87 to 93, wherein $X^1$ is $C(R^3)$, $R^3$ is hydrogen, $R^1$ is methyl, $R^8$ is methyl and $R^2$ is —$OCH_3$.

Embodiment 103

The compound of any one of embodiments 87 to 93, wherein $X^1$ is N.

Embodiment 104

The compound of any one of embodiments 1 to 7 or embodiments 87 to 93, wherein $R^4$ and $R^5$ are combined to form a ring Z having the formula:

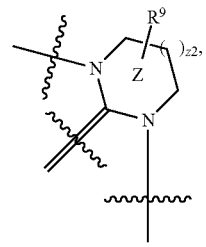

wherein z2 is 0, 1, or 2; $R^9$ is independently hydrogen, halogen, —$N_3$, —$CF_3$, —$CCl_3$, —$CBr_3$, —$CI_3$, —CN, —CHO, —$OR^{9A}$, —$NR^{9A}R^{9B}$, —$COOR^{9A}$, —$C(O)NR^{9A}R^{9B}$, —$NO_2$, —$SR^{9A}$, —$S(O)_{n9}R^{9A}$, —$S(O)_{n9}OR^{9A}$, —$S(O)_{n9}NR^{9A}R^{9B}$, —$NHNR^{9A}R^{9B}$, —$ONR^{9A}R^{9B}$, —NHC(O)$NHNR^{9A}R^{9B}$, substituted or unsubstituted alkyl, substituted or unsubstituted heteroalkyl, substituted or unsubstituted cycloalkyl, substituted or unsubstituted heterocycloalkyl, substituted or unsubstituted aryl, or substituted or unsubstituted heteroaryl; $R^{9A}$ and $R^{9B}$ are independently hydrogen, substituted or unsubstituted alkyl, substituted or unsubstituted heteroalkyl, substituted or unsubstituted cycloalkyl, substituted or unsubstituted heterocycloalkyl, substituted or unsubstituted aryl, or substituted or unsubstituted heteroaryl; and n9 is 1 or 2.

Embodiment 105

The compound of embodiment 104, said compound comprising a plurality of independent $R^9$ substituents.

Embodiment 106

The compound of embodiment 104, wherein z2 is 0.

Embodiment 107

The compound of embodiment 104, wherein z2 is 1.

Embodiment 108

The compound of embodiment 104, wherein z2 is 2.

Embodiment 109

The compound of embodiment 104, wherein $R^9$ is hydrogen, halogen, $-OR^{9A}$, $-NR^{9A}R^{9B}$, substituted or unsubstituted alkyl, substituted or unsubstituted cycloalkyl, or substituted or unsubstituted heterocycloalkyl.

Embodiment 110

The compound of embodiment 109, wherein $R^9$ is hydrogen.

Embodiment 111

The compound of embodiment 109, wherein $R^9$ is halogen.

Embodiment 112

The compound of embodiment 109, wherein $R^9$ is fluoro.

Embodiment 113

The compound of embodiment 109, wherein $R^9$ is —OH.

Embodiment 114

The compound of embodiment 109, wherein $R^9$ is $-N(CH_3)_2$.

Embodiment 115

The compound of embodiment 109, wherein $R^9$ is unsubstituted alkyl.

Embodiment 116

The compound of embodiment 115, wherein $R^9$ is methyl, ethyl, n-propyl, isopropyl, isobutyl or pentyl.

Embodiment 117

The compound of embodiment 109, wherein $R^9$ is substituted alkyl.

Embodiment 118

The compound of embodiment 117, wherein $R^9$ is $-CH_2OH$, $-C(CH_3)_2OH$.

Embodiment 119

The compound of embodiment 109, wherein $R^9$ is substituted or unsubstituted cycloalkyl.

Embodiment 120

The compound of embodiment 109, wherein $R^9$ is substituted or unsubstituted heterocycloalkyl.

Embodiment 121

The compound of embodiment 120, wherein $R^9$ is pyrrolidinyl-2,5-dione.

Embodiment 122

The compound of embodiment 120, wherein $R^9$ is pyrrolidin-1-yl.

Embodiment 123

The compound of embodiment 104, wherein $X^1$ is $C(R^3)$, $R^3$ is hydrogen, $R^1$ is unsubstituted alkyl and $R^2$ is $-OR^{2A}$.

Embodiment 124

The compound of embodiment 104, wherein $X^1$ is $C(R^3)$, $R^3$ is hydrogen, $R^1$ is unsubstituted $C_1$-$C_5$ alkyl and $R^2$ is $-OR^{2A}$, wherein $R^{2A}$ is unsubstituted $C_1$-$C_5$ alkyl.

Embodiment 125

The compound of one of embodiments 104 or 110, wherein $X^1$ is $C(R^3)$, $R^3$ is hydrogen, $R^1$ is methyl and $R^2$ is $-OCH_3$.

Embodiment 126

The compound of any one of embodiments 1 to 7 or embodiments 87 to 93, wherein $R^4$ and $R^5$ are combined to form a ring Y having the formula:

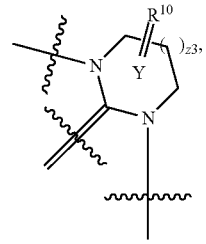

wherein z3 is 0, 1, or 2; $R^{10}$ is =O, =S, $=CR^{10A}R^{10B}$, or $=NR^{10C}$; $R^{10A}$ and $R^{10B}$ are independently hydrogen, halogen, $-N_3$, $-CF_3$, $-CCl_3$, $-CBr_3$, $-CI_3$, $-CN$, $-CHO$, $-OR^{3A}$, $-NR^{3A}R^{3B}$, $-COOR^{3A}$, $-C(O)NR^{3A}R^{3B}$, $-NO_2$, $-SR^{3A}$, $-S(O)_{n3}R^{3A}$, $-S(O)_{n3}OR^{3A}$, $-S(O)_{n3}NR^{3A}R^{3B}$, $-NHNR^{3A}R^{3B}$, $-ONR^{3A}R^{3B}$, $-NHC(O)NHNR^{3A}R^{3B}$, substituted or unsubstituted alkyl, substituted or unsubstituted heteroalkyl, substituted or unsubstituted cycloalkyl, substituted or unsubstituted heterocycloalkyl, substituted or unsubstituted aryl, or substituted or unsubstituted heteroaryl; and $R^{10C}$ is hydrogen, or $-OR^{3A}$.

Embodiment 127

The compound of embodiment 126, wherein z3 is 0.

Embodiment 128

The compound of embodiment 126, wherein z3 is 1.

Embodiment 129

The compound of embodiment 126, wherein z3 is 2.

97

Embodiment 130

The compound of embodiment 126, wherein $R^{10}$ is $=CR^{10A}R^{10B}$.

Embodiment 131

The compound of embodiment 130, wherein $R^{10}$ is $-CH_2$.

Embodiment 132

The compound of embodiment 126, wherein $R^{10}$ is $=NR^{10C}$.

Embodiment 133

The compound of embodiment 132, wherein $R^{10}$ is $=N-OH$ or $=NOCH_3$.

Embodiment 134

A pharmaceutical composition comprising a compound according to any one of embodiments 1 to 7 or embodiments 87 to 93 and a pharmaceutically acceptable carrier.

Embodiment 135

The pharmaceutical composition of embodiment 134, wherein said pharmaceutical composition is formulated for administration one or twice daily.

Embodiment 136

Use of a compound according to any one of embodiments 1 to 7 or embodiments 87 to 93 for inhibiting production of $A\beta_{42}$ or $A\beta_{40}$ by a protease which proteolyzes an amyloid precursor protein (APP) or fragment thereof.

Embodiment 137

The use of embodiment 136, wherein said compound has no measurable effect on gamma-secretase-mediated processing of Notch-1 receptor or no adverse effect associated with any altered Notch-1 receptor signaling.

Embodiment 138

Use of a compound according to any one of embodiments 1 to 7 or embodiments 87 to 93 for treating a disease or neurological disorder associated with elevated levels of specific fibrillogenic Aβ peptides by inhibiting production of $A\beta_{42}$ or $A\beta_{40}$.

Embodiment 139

The use of embodiment 138, wherein the disease or neurological disorder is Alzheimer's disease, Down Syndrome (DS), hemorrhagic stroke associated with cerebrovascular amyloidosis (HCHWA), cerebral amyloid angiopathy (CAA), idiopathic dilated cardiomyopathy, hereditary cerebral hemorrhage with amyloidosis, Dutch type (HCHWA-D), prion disorders, Creutzfeldt-Jakob disease (CJD), frontotemporal dementias (FTD), amyotrophic lateral sclerosis (ALS), Huntington's disease (HD), Parkinson's disease (PD) and other neurodegenerative proteinopathies.

98

What is claimed is:

1. A compound having the formula:

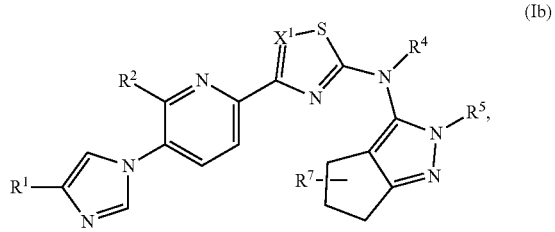

(Ib)

wherein, $X^1$ is $C(R^3)$ or N;

$R^1$ is hydrogen, halogen, $-N_3$, $-CF_3$, $-CCl_3$, $-CBr_3$, $-CI_3$, $-CN$, $-CHO$, $-OR^{1A}$, $-NR^{1A}R^{1B}$, $-COOR^{1A}$, $-C(O)NR^{1A}R^{1B}$, $-NO_2$, $-SR^{1A}$, $-S(O)_{n1}R^{1A}$, $-S(O)_{n1}OR^{1A}$, $-S(O)_{n1}NR^{1A}R^{1B}$, $-NHNR^{1A}R^{1B}$, $-ONR^{1A}R^{1B}$, $-NHC(O)NHNR^{1A}R^{1B}$, substituted or unsubstituted alkyl, substituted or unsubstituted heteroalkyl, substituted or unsubstituted cycloalkyl, substituted or unsubstituted heterocycloalkyl, substituted or unsubstituted aryl, or substituted or unsubstituted heteroaryl;

$R^2$ is hydrogen, halogen, $-N_3$, $-CF_3$, $-CCl_3$, $-CBr_3$, $-CI_3$, $-CN$, $-CHO$, $-OR^{2A}$, $-NR^{2A}R^{2B}$, $-COOR^{2A}$, $-C(O)NR^{2A}R^{2B}$, $-NO_2$, $-SR^{2A}$, $-S(O)_{n2}R^{2A}$, $-S(O)_{n2}OR^{2A}$, $-S(O)_{n2}NR^{2A}R^{2B}$, $-NHNR^{2A}R^{2B}$, $-ONR^{2A}R^{2B}$, $-NHC(O)NHNR^{2A}R^{2B}$, substituted or unsubstituted alkyl, substituted or unsubstituted heteroalkyl, substituted or unsubstituted cycloalkyl, substituted or unsubstituted heterocycloalkyl, substituted or unsubstituted aryl, or substituted or unsubstituted heteroaryl;

$R^3$ is hydrogen, halogen, $-N_3$, $-CF_3$, $-CCl_3$, $-CBr_3$, $-CI_3$, $-CN$, $-CHO$, $-OR^{3A}$, $-NR^{3A}R^{3B}$, $-COOR^{3A}$, $-C(O)NR^{3A}R^{3B}$, $-NO_2$, $-SR^{3A}$, $-S(O)_{n3}R^{3A}$, $-S(O)_{n3}OR^{3A}$, $-S(O)_{n3}NR^{3A}R^{3B}$, $-NHNR^{3A}R^{3B}$, $-ONR^{3A}R^{3B}$, $-NHC(O)NHNR^{3A}R^{3B}$, substituted or unsubstituted alkyl, substituted or unsubstituted heteroalkyl, substituted or unsubstituted cycloalkyl, substituted or unsubstituted heterocycloalkyl, substituted or unsubstituted aryl, or substituted or unsubstituted heteroaryl;

$R^4$ is hydrogen, halogen, $-N_3$, $-CF_3$, $-CCl_3$, $-CBr_3$, $-CI_3$, $-CN$, $-CHO$, $-OR^{4A}$, $-NR^{4A}R^{4B}$, $-COOR^{4A}$, $-C(O)NR^{4A}R^{4B}$, $-NO_2$, $-SR^{4A}$, $-S(O)_{n4}R^{4A}$, $-S(O)_{n4}OR^{4A}$, $-S(O)_{n4}NR^{4A}R^{4B}$, $-NHNR^{4A}R^{4B}$, $-ONR^{4A}R^{4B}$, $-NHC(O)NHNR^{4A}R^{4B}$, substituted or unsubstituted alkyl, substituted or unsubstituted heteroalkyl, substituted or unsubstituted cycloalkyl, substituted or unsubstituted heterocycloalkyl, substituted or unsubstituted aryl, or substituted or unsubstituted heteroaryl;

$R^5$ is hydrogen, halogen, $-N_3$, $-CF_3$, $-CCl_3$, $-CBr_3$, $-CI_3$, $-CN$, $-CHO$, $-OR^{5A}$, $-NR^{5A}R^{5B}$, $-COOR^{5A}$, $-C(O)NR^{5A}R^{5B}$, $-NO_2$, $-SR^{5A}$, $-S(O)_{n5}R^{5A}$, $-S(O)_{n5}OR^{5A}$, $-S(O)_{n5}NR^{5A}R^{5B}$, $-NHNR^{5A}R^{5B}$, $-ONR^{5A}R^{5B}$, $-NHC(O)NHNR^{5A}R^{5B}$, substituted or unsubstituted alkyl, substituted or unsubstituted heteroalkyl, substituted or unsubstituted cycloalkyl, substituted or unsubstituted heterocycloalkyl, substituted or unsubstituted aryl, or substituted or unsubstituted heteroaryl, wherein $R^4$ and R$^5$ are optionally joined together to form a substituted or unsubstituted heterocycloalkyl or substituted or unsubstituted heteroaryl;

R$^7$ is independently hydrogen, halogen, —N$_3$, —CF$_3$, —CCl$_3$, —CBr$_3$, —CI$_3$, —CN, —CHO, —OR$^{7A}$, —NR$^{7A}$R$^{7B}$, —COOR$^{7A}$, —C(O)NR$^{7A}$R$^{7B}$, —NO$_2$, —SR$^{7A}$, —S(O)$_{n7}$R$^{7A}$, —S(O)$_{n7}$OR$^{7A}$, —S(O)$_{n7}$NR$^{7A}$R$^{7B}$, —NHNR$^{7A}$R$^{7B}$, —ONR$^{7A}$R$^{7B}$, —NHC(O)NHNR$^{7A}$R$^{7B}$, substituted or unsubstituted alkyl, substituted or unsubstituted heteroalkyl, substituted or unsubstituted cycloalkyl, substituted or unsubstituted heterocycloalkyl, substituted or unsubstituted aryl, or substituted or unsubstituted heteroaryl;

R$^{1A}$, R$^{1B}$, R$^{2A}$, R$^{2B}$, R$^{3A}$, R$^{3B}$, R$^{4A}$, R$^{4B}$, R$^{5A}$, R$^{5B}$, R$^{7A}$ and R$^{7B}$ are independently hydrogen, substituted or unsubstituted alkyl, substituted or unsubstituted heteroalkyl, substituted or unsubstituted cycloalkyl, substituted or unsubstituted heterocycloalkyl, substituted or unsubstituted aryl, or substituted or unsubstituted heteroaryl; and n1, n2, n3, n4, n5 and n7 are independently 1 or 2.

2. The compound of claim 1, wherein R$^1$ is substituted or unsubstituted alkyl.

3. The compound of claim 1, wherein R$^1$ is methyl.

4. The compound of claim 1, wherein R$^2$ is hydrogen or —OR$^{2A}$.

5. The compound of claim 4, wherein R$^{2A}$ is selected from the group consisting of hydrogen and substituted or unsubstituted alkyl.

6. The compound of claim 4, wherein R$^{2A}$ is methyl.

7. The compound of claim 1, wherein R$^3$ is hydrogen, halogen, —CF$_3$, —CCl$_3$, —CBr$_3$, —CI$_3$, —CN, substituted or unsubstituted alkyl, substituted or unsubstituted heteroalkyl, substituted or unsubstituted cycloalkyl, or substituted or unsubstituted heterocycloalkyl.

8. The compound of claim 1, wherein R$^3$ is hydrogen.

9. The compound of claim 1, wherein R$^4$ is hydrogen, or substituted or unsubstituted alkyl.

10. The compound of claim 1, wherein R$^4$ is hydrogen.

11. The compound of claim 1, wherein R$^5$ is hydrogen, substituted or unsubstituted alkyl, substituted or unsubstituted heteroalkyl, substituted or unsubstituted cycloalkyl, or substituted or unsubstituted heterocycloalkyl, wherein R$^4$ and R$^5$ are optionally joined together to form a substituted or unsubstituted heterocycloalkyl.

12. The compound of claim 1, wherein R$^5$ is methyl, ethyl, n-propyl, isopropyl, isobutyl or pentyl.

13. The compound of claim 1, wherein R$^5$ is —CH$_2$F, —CH$_2$CH$_2$F, —CH$_2$CF$_3$, —(CH$_2$)$_2$OH, —C(CH$_3$)$_2$OH, —CH$_2$CH(CH$_3$)OH, or —CH$_2$C(CH$_3$)$_2$OH.

14. The compound of claim 1, wherein R$^7$ is independently hydrogen, —CF$_3$, or unsubstituted alkyl.

15. The compound of claim 1, wherein X$^1$ is C(R$^3$), R$^3$ and R$^7$ are hydrogen, R$^1$ is methyl, and R$^2$ is —OCH$_3$.

16. The compound of claim 1, wherein R$^4$ and R$^5$ are combined to form a ring Z having the formula:

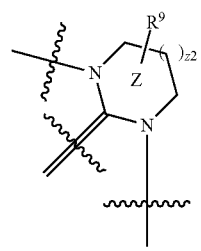

wherein z2 is 0, 1, or 2;

R$^9$ is independently hydrogen, halogen, —N$_3$, —CF$_3$, —CCl$_3$, —CBr$_3$, —CI$_3$, —CN, —CHO, —OR$^{9A}$, —NR$^{9A}$R$^{9B}$, —COOR$^{9A}$, —C(O)NR$^{9A}$R$^{9B}$, —NO$_2$, —SR$^{9A}$, —S(O)$_{n9}$R$^{9A}$, —S(O)$_{n9}$OR$^{9A}$, —S(O)ONR$^{9A}$R$^{9B}$, —NHNR$^{9A}$R$^{9B}$, —ONR$^{9A}$R$^{9B}$, —NHC(O)NHNR$^{9A}$R$^{9B}$, substituted or unsubstituted alkyl, substituted or unsubstituted heteroalkyl, substituted or unsubstituted cycloalkyl, substituted or unsubstituted heterocycloalkyl, substituted or unsubstituted aryl, or substituted or unsubstituted heteroaryl;

R$^{9A}$ and R$^{9B}$ are independently hydrogen, substituted or unsubstituted alkyl, substituted or unsubstituted heteroalkyl, substituted or unsubstituted cycloalkyl, substituted or unsubstituted heterocycloalkyl, substituted or unsubstituted aryl, or substituted or unsubstituted heteroaryl; and n9 is 1 or 2.

17. The compound of claim 16, wherein z2 is 0 or 1.

18. The compound of claim 16, wherein R$^9$ is hydrogen, halogen, —OR$^{9A}$, —NR$^{9A}$R$^{9B}$, substituted or unsubstituted alkyl, substituted or unsubstituted cycloalkyl, or substituted or unsubstituted heterocycloalkyl.

19. The compound of claim 16, wherein R$^9$ is hydrogen, fluoro, or —OH.

20. The compound of claim 16, wherein R$^9$ is methyl, ethyl, n-propyl, isopropyl, isobutyl or pentyl.

21. The compound of claim 16, wherein X$^1$ is C(R$^3$), R$^3$ is hydrogen, R$^1$ is methyl and R$^2$ is —OCH$_3$.

22. The compound of claim 1 selected from the group consisting of:

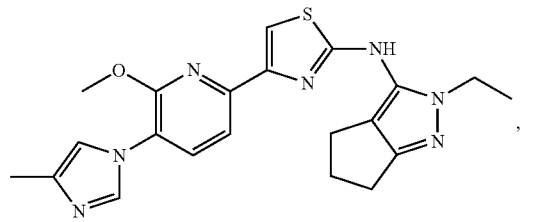

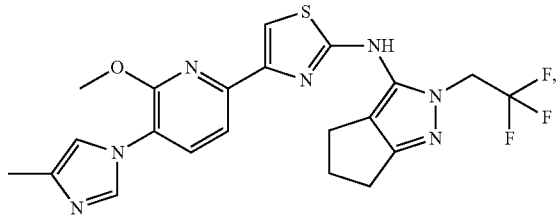

and

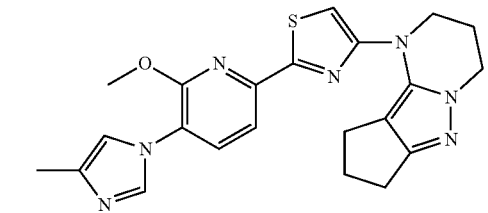

23. A method of treating Alzheimer's disease in a subject in need thereof, comprising inhibiting production of Aβ$_{42}$ or Aβ$_{40}$ in the subject by administering to the subject a compound having the formula:

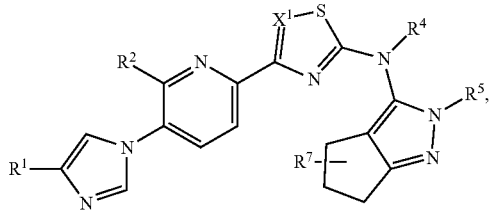

(Ib)

wherein,

X$^1$ is C(R$^3$) or N;

R$^1$ is hydrogen, halogen, —N$_3$, —CF$_3$, —CCl$_3$, —CBr$_3$, —CI$_3$, —CN, —CHO, —OR$^{1A}$, —NR$^{1A}$R$^{1B}$, —COOR$^{1A}$, —C(O)NR$^{1A}$R$^{1B}$, —NO$_2$, —SR$^{1A}$, —S(O)$_{n1}$R$^{1A}$, —S(O)$_{n1}$OR$^{1A}$, —S(O)$_{n1}$NR$^{1A}$R$^{1B}$, —NHNR$^{1A}$R$^{1B}$, —ONR$^{1A}$R$^{1B}$, —NHC(O)NHNR$^{1A}$R$^{1B}$, substituted or unsubstituted alkyl, substituted or unsubstituted heteroalkyl, substituted or unsubstituted cycloalkyl, substituted or unsubstituted heterocycloalkyl, substituted or unsubstituted aryl, or substituted or unsubstituted heteroaryl;

R$^2$ is hydrogen, halogen, —N$_3$, —CF$_3$, —CCl$_3$, —CBr$_3$, —CI$_3$, —CN, —CHO, —OR$^{2A}$, —NR$^{2A}$R$^{2B}$, —COOR$^{2A}$, —C(O)NR$^{2A}$R$^{2B}$, —NO$_2$, —SR$^{2A}$, —S(O)$_{n2}$R$^{2A}$, —S(O)$_{n2}$OR$^{2A}$, —S(O)$_{n2}$NR$^{2A}$R$^{2B}$, —NHNR$^{2A}$R$^{2B}$, —ONR$^{2A}$R$^{2B}$, —NHC(O)NHNR$^{2A}$R$^{2B}$, substituted or unsubstituted alkyl, substituted or unsubstituted heteroalkyl, substituted or unsubstituted cycloalkyl, substituted or unsubstituted heterocycloalkyl, substituted or unsubstituted aryl, or substituted or unsubstituted heteroaryl;

R$^3$ is hydrogen, halogen, —N$_3$, —CF$_3$, —CCl$_3$, —CBr$_3$, —CI$_3$, —CN, —CHO, —OR$^{3A}$, —NR$^{3A}$R$^{3B}$, —COOR$^{3A}$, —C(O)NR$^{3A}$R$^{3B}$, —NO$_2$, —SR$^{3A}$, —S(O)$_{n3}$R$^{3A}$, —S(O)$_{n3}$OR$^{3A}$, —S(O)$_{n3}$NR$^{3A}$R$^{3B}$, —NHNR$^{3A}$R$^{3B}$, —ONR$^{3A}$R$^{3B}$, —NHC(O)NHNR$^{3A}$R$^{3B}$, substituted or unsubstituted alkyl, substituted or unsubstituted heteroalkyl, substituted or unsubstituted cycloalkyl, substituted or unsubstituted heterocycloalkyl, substituted or unsubstituted aryl, or substituted or unsubstituted heteroaryl;

R$^4$ is hydrogen, halogen, —N$_3$, —CF$_3$, —CCl$_3$, —CBr$_3$, —CI$_3$, —CN, —CHO, —OR$^{4A}$, —NR$^{4A}$R$^{4B}$, —COOR$^{4A}$, —C(O)NR$^{4A}$R$^{4B}$, —NO$_2$, —SR$^{4A}$, —S(O)$_{n4}$R$^{4A}$, —S(O)$_{n4}$OR$^{4A}$, —S(O)$_{n4}$NR$^{4A}$R$^{4B}$, —NHNR$^{4A}$R$^{4B}$, —ONR$^{4A}$R$^{4B}$, —NHC(O)NHNR$^{4A}$R$^{4B}$, substituted or unsubstituted alkyl, substituted or unsubstituted heteroalkyl, substituted or unsubstituted cycloalkyl, substituted or unsubstituted heterocycloalkyl, substituted or unsubstituted aryl, or substituted or unsubstituted heteroaryl;

R$^5$ is hydrogen, halogen, —N$_3$, —CF$_3$, —CCl$_3$, —CBr$_3$, —CI$_3$, —CN, —CHO, —OR$^{5A}$, —NR$^{5A}$R$^{5B}$, —COOR$^{5A}$, —C(O)NR$^{5A}$R$^{5B}$, —NO$_2$, —SR$^{5A}$, —S(O)$_{n5}$R$^{5A}$, —S(O)$_{n5}$OR$^{5A}$, —S(O)$_{n5}$NR$^{5A}$R$^{5B}$, —NHNR$^{5A}$R$^{5B}$, —ONR$^{5A}$R$^{5B}$, —NHC(O)NHNR$^{5A}$R$^{5B}$, substituted or unsubstituted alkyl, substituted or unsubstituted heteroalkyl, substituted or unsubstituted cycloalkyl, substituted or unsubstituted heterocycloalkyl, substituted or unsubstituted aryl, or substituted or unsubstituted heteroaryl, wherein R$^4$ and R$^5$ are optionally joined together to form a substituted or unsubstituted heterocycloalkyl or substituted or unsubstituted heteroaryl;

R$^7$ is independently hydrogen, halogen, —N$_3$, —CF$_3$, —CCl$_3$, —CBr$_3$, —CI$_3$, —CN, —CHO, —OR$^{7A}$, —NR$^{7A}$R$^{7B}$, —COOR$^{7A}$, —C(O)NR$^{7A}$R$^{7B}$, —NO$_2$, —SR$^{7A}$, —S(O)$_{n7}$R$^{7A}$, —S(O)$_{n7}$OR$^{7A}$, —S(O)$_{n7}$NR$^{7A}$R$^{7B}$, —NHNR$^{7A}$R$^{7B}$, —ONR$^{7A}$R$^{7B}$, —NHC(O)NHNR$^{7A}$R$^{7B}$, substituted or unsubstituted alkyl, substituted or unsubstituted heteroalkyl, substituted or unsubstituted cycloalkyl, substituted or unsubstituted heterocycloalkyl, substituted or unsubstituted aryl, or substituted or unsubstituted heteroaryl;

R$^{1A}$, R$^{1B}$, R$^{2A}$, R$^{2B}$, R$^{3A}$, R$^{3B}$, R$^{4A}$, R$^{4B}$, R$^{5A}$, R$^{5B}$, R$^{7A}$ and R$^{7B}$ are independently hydrogen, substituted or unsubstituted alkyl, substituted or unsubstituted heteroalkyl, substituted or unsubstituted cycloalkyl, substituted or unsubstituted heterocycloalkyl, substituted or unsubstituted aryl, or substituted or unsubstituted heteroaryl; and n1, n2, n3, n4, n5 and n7 are independently 1 or 2.

\* \* \* \* \*

UNITED STATES PATENT AND TRADEMARK OFFICE
CERTIFICATE OF CORRECTION

| | |
|---|---|
| PATENT NO. | : 9,938,263 B2 |
| APPLICATION NO. | : 14/775483 |
| DATED | : April 10, 2018 |
| INVENTOR(S) | : Rudolph E. Tanzi et al. |

It is certified that error appears in the above-identified patent and that said Letters Patent is hereby corrected as shown below:

On the Title Page

In Column 2 (Abstract), Line 1, delete "inner" and insert -- inter --

In the Claims

In Column 100, Lines 6-7, In Claim 16, delete "—S(O)ONR$^{9A}$R$^{9B}$," and insert -- —S(O)$_{n9}$NR$^{9A}$R$^{9B}$, --

Signed and Sealed this
Nineteenth Day of June, 2018

Andrei Iancu
*Director of the United States Patent and Trademark Office*

UNITED STATES PATENT AND TRADEMARK OFFICE
CERTIFICATE OF CORRECTION

| | | |
|---|---|---|
| PATENT NO. | : 9,938,263 B2 | Page 1 of 1 |
| APPLICATION NO. | : 14/775483 | |
| DATED | : April 10, 2018 | |
| INVENTOR(S) | : Rudolph E. Tanzi et al. | |

It is certified that error appears in the above-identified patent and that said Letters Patent is hereby corrected as shown below:

In the Specification

In Column 1, Line 20, delete "1U01NS074501-1 awarded by NIH/NINDS." and insert -- NS074501 awarded by the National Institutes of Health. --

Signed and Sealed this
Eighth Day of August, 2023

Katherine Kelly Vidal
*Director of the United States Patent and Trademark Office*